US012616412B2

(12) United States Patent
García Quintanilla et al.

(10) Patent No.: US 12,616,412 B2
(45) Date of Patent: May 5, 2026

(54) METHOD FOR THE IDENTIFICATION OF CARDIAC FIBRILLATION DRIVERS AND/OR THE FOOTPRINT OF ROTATIONAL ACTIVATIONS USING SINGLE OPTICAL OR ELECTRICAL SIGNALS WITHOUT REQUIRING PANORAMIC SIMULTANEOUS ACQUISITION

(71) Applicants: CENTRO NACIONAL DE INVESTIGACIONES CARDIOVASCULARES CARLOS III (F.S.P.), Madrid (ES); FUNDACIÓN PARA LA INVESTIGACIÓN BIOMÉDICA DEL HOSPITAL CLÍNICO SAN CARLOS, Madrid (ES)

(72) Inventors: Jorge García Quintanilla, Madrid (ES); David Filgueiras Rama, Madrid (ES); Nicasio Pérez Castellano, Madrid (ES); Julián Pérez-Villacastín Domínguez, Madrid (ES)

(73) Assignees: CENTRO NACIONAL DE INVESTIGACIONES CARDIOVASCULARES CARLOS III (F.S.P.), Madrid (ES); FUNDACIÓN PARA LA INVESTIGACIÓN BIOMÉDICA DEL HOSPITAL CLÍNICO SAN CARLOS, Madrid (ES)

( * ) Notice: Subject to any disclaimer, the term of this patent is extended or adjusted under 35 U.S.C. 154(b) by 1361 days.

(21) Appl. No.: 17/284,195

(22) PCT Filed: Oct. 11, 2019

(86) PCT No.: PCT/EP2019/077610
§ 371 (c)(1),
(2) Date: Apr. 9, 2021

(87) PCT Pub. No.: WO2020/074712
PCT Pub. Date: Apr. 16, 2020

(65) Prior Publication Data

US 2021/0338137 A1 Nov. 4, 2021

(30) Foreign Application Priority Data

Oct. 11, 2018 (EP) .................................... 18382729

(51) Int. Cl.
*A61B 5/361* (2021.01)
*A61B 5/283* (2021.01)
(Continued)

(52) U.S. Cl.
CPC .............. *A61B 5/361* (2021.01); *A61B 5/283* (2021.01); *A61B 5/343* (2021.01); *A61B 5/367* (2021.01); *A61B 2034/2061* (2016.02)

(58) Field of Classification Search
CPC ......... A61B 5/361; A61B 5/283; A61B 5/367; A61B 5/343; A61B 2034/2061
See application file for complete search history.

(56) References Cited

U.S. PATENT DOCUMENTS 5,609,613 A 3/1997 Woodson et al.
9,427,166 B2 * 8/2016 Dubois .............. A61B 18/1492
(Continued)

OTHER PUBLICATIONS

Ng et al., "Iterative Method to Detect Atrial Activations and Measure Cycle Length From Electrograms During Atrial Fibrillation," *IEEE Transactions on Biomedical Engineering* 61(2):273-278, Feb. 2014.
(Continued)

*Primary Examiner* — Carl H Layno
*Assistant Examiner* — Maria Catherine Anthony
(74) *Attorney, Agent, or Firm* — Hayes Soloway, PC

(57) ABSTRACT

This invention relates to an ex vivo use of the instantaneous frequency modulation (iFM) signal of cardiac activations and to an ex vivo use of the instantaneous amplitude modulation (iAM) signal obtained from the sequence of amplitude excursions of said activations for detecting 'driver' or 'high-hierarchy' regions and/or the cardiac spots that display the footprint of rotational activations in the heart of a subject with cardiac fibrillation without requiring panoramic simultaneous acquisition.

17 Claims, 54 Drawing Sheets

(51) Int. Cl.

| | |
|---|---|
| ***A61B 5/343*** | (2021.01) |
| ***A61B 5/367*** | (2021.01) |
| *A61B 34/20* | (2016.01) |

(56) References Cited

U.S. PATENT DOCUMENTS

| | | | | |
|---|---|---|---|---|
| 2010/0274123 | A1 | 10/2010 | Voth | |
| 2012/0089038 | A1 | 4/2012 | Ryu et al. | |
| 2013/0080378 | A1* | 3/2013 | Huang .................... | G06F 17/18 706/54 |
| 2016/0166166 | A1* | 6/2016 | Bunch .................. | A61B 5/7264 600/518 |
| 2018/0355427 | A1 | 12/2018 | Martín Fernández et al. | |
| 2019/0112582 | A1 | 4/2019 | Redondo Moya et al. | |
| 2021/0186989 | A1 | 6/2021 | Sancho Madrid et al. | |

OTHER PUBLICATIONS

U.S. Appl. No. 17/122,962, filed Dec. 15, 2020.

* cited by examiner

Condition A (interval of drifting rotor):
increasing iFM(t) ≥ 4 cycles AND [(iAM(t) increases ≥ 25% for ≥ 3 cycles reaching ≥ 80%) OR (iAM(t) ≥ 80%)]

Condition B (interval of quasi-stationary/meandering rotor):
iFM(t) ≥ Percentile 70 AND iAM(t) ≥ 80 % for at least 2 cycles.

Parameters in this example:
Min. increasing iFM cycles: 4
Min. iAM excursion: 25%
Min. increasing iAM cycles: 3
iAM threshold: 80%
Min. iFM percentile: 70

*Condition A (interval of drifting rotor):*
*increasing iFM(t) ≥ 4 cycles <u>AND</u> [(iAM(t) increases ≥ 25% for ≥ 3 cycles reaching ≥ 80%) <u>OR</u> iAM(t) ≥ 80%]*

*Condition B (interval of quasi-stationary/meandering rotor):*
*iFM(t) ≥ Percentile 70 <u>AND</u> iAM(t) ≥ 80 % for at least 2 cycles.*

*<u>Parameters in this example:</u>*
*Min. increasing iFM cycles: 4*
*Min. iAM excursion: 25%*
*Min. increasing iAM cycles: 3*
*iAM threshold : 80%*
*Min. iFM percentile: 70*

***Condition A (interval of drifting rotor)*:***
*increasing iFM(t) ≥ 4 cycles <u>AND</u> [(iAM(t) increases ≥ 25% for ≥ 3 cycles reaching ≥ 85%) <u>OR</u> iAM(t) ≥ 85%]*

*Condition B (interval of quasi-stationary/meandering rotor):*
*iFM(t) ≥ Percentile 70 <u>AND</u> iAM(t) ≥ 85 % for at least 2 cycles.*

*<u>Parameters in this example:</u>*
*Min. increasing iFM cycles: 4*
*Min. iAM excursion: 25%*
*Min. increasing iAM cycles: 3*
*iAM threshold : 85%*
*Min. iFM percentile: 70*

** If iAM remained above the 85% threshold, rotational footprint would be still detected after the end of the increasing iFM cycles. That would account for approaching rotors (increasing iFM, decreasing iAM) that eventually remain in the area with little or not drifting at all (iAM above the threshold but no increasing iFM).*

METHOD FOR THE IDENTIFICATION OF CARDIAC FIBRILLATION DRIVERS AND/OR THE FOOTPRINT OF ROTATIONAL ACTIVATIONS USING SINGLE OPTICAL OR ELECTRICAL SIGNALS WITHOUT REQUIRING PANORAMIC SIMULTANEOUS ACQUISITION

TECHNICAL FIELD OF THE INVENTION

This invention relates generally to minimally invasive treatment of organs inside the body. More particularly, this invention relates to determination of ablation sites for ablation treatments applied to cardiac tissue.

BACKGROUND OF THE INVENTION

There is evidence of a progressive increase in overall burden of atrial fibrillation (AF), its incidence, prevalence, and associated mortality between 1990 and 2010. Only in Europe, the current prevalence of AF is 2%, twice as many as the last decade. Given that AF is associated with significant morbidity and mortality, this increasing number of individuals with AF will have major public health implications. Indeed, the average lifetime risk of AF has been recently reported as 37%. Pulmonary vein isolation (PVI) is still considered the cornerstone of catheter ablation for treating AF. However, radiofrequency-based ablation of AF during persistent stages (persistent AF: AF episodes lasting ≥7 days, PersAF) is challenging and associated with less favourable outcomes than paroxysmal AF (AF episodes lasting <7 days). The latter is a consequence of the fact that many more mechanisms and different atrial regions can play an important role in PersAF maintenance. To improve outcomes, ablation targeting the substrate that allegedly maintains PersAF was often added to PVI. The two most common techniques for substrate modification were the creation of linear lesions in the left atrium (LA) or targeting "complex fractionated atrial electrograms" (CFAEs). However, the STAR-AF II trial concluded that there was no incremental benefit of these two techniques in addition to PVI. In this context, new approaches such as the ablation of areas with spatiotemporal dispersion, or costly multielectrode (64-256) simultaneous panoramic acquisition systems (MESPAS, e.g. RhythmView™, Abbott/CardioInsight™, Medtronic) are being increasingly used in addition to the mandatory conventional electroanatomical mapping system to improve outcomes in PersAF. Such approaches aim at detecting and ablating alleged drivers (rotational or centrifugal) using propriety algorithms. These alleged drivers are ablated regardless their activation frequency dynamics which, for some, may be justified because previous attempts to guide ablation using dominant frequency (DF) yielded suboptimal results in PersAF. However, this might make these approaches potentially unspecific. In addition, sensitivity and specificity of the MESPAS used to detect rotational activations (rotors) and/or centrifugal activations (foci) are further limited by multiple technical aspects. Thus, current clinical outcomes obtained with those systems are controversial and a matter of debate. Moreover, the use of these propriety MESPAS and their own expendable materials considerably increases the cost of AF ablation procedures.

From the foregoing, it is clear that incorporating single-signal algorithms capable of detecting rotational activations (rotors) and/or cardiac fibrillation (preferably AF) 'high-hierarchy' driver regions into a standard electroanatomical mapping system without the need of costly simultaneous panoramic acquisition systems would significantly improve, simplify and make more cost-effective these patient-tailored, mechanistically-based ablation procedures for cardiac fibrillation (preferably AF, or PersAF).

Therefore, the algorithm does mark the pixel as 'rotational-footprint negative'. D. Comparison between the pixels actually crossed by a PS (PS map, 'gold standard') and the pixels detected by the single-signal algorithm as 'rotational-footprint positive' (iFM/iAM map). Note the extremely high similarity between them, resulting in >97% sensitivity and specificity values in this example. The size of a conventional 3.5 mm tip ablation catheter is shown for reference. The signals showed in A-C were taken from 'a', 'b', and 'c'.

Figure 3:
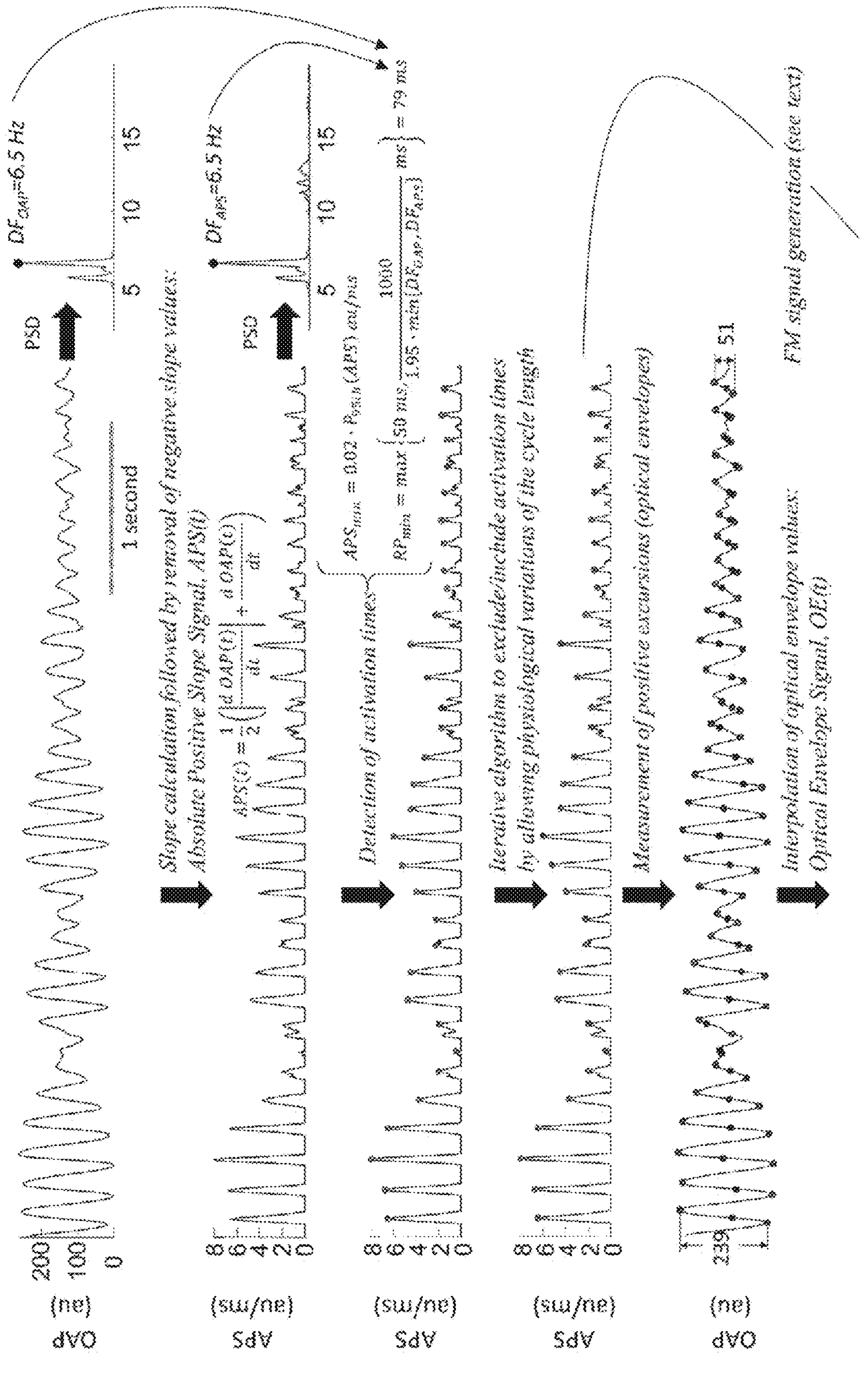
Figure 3:
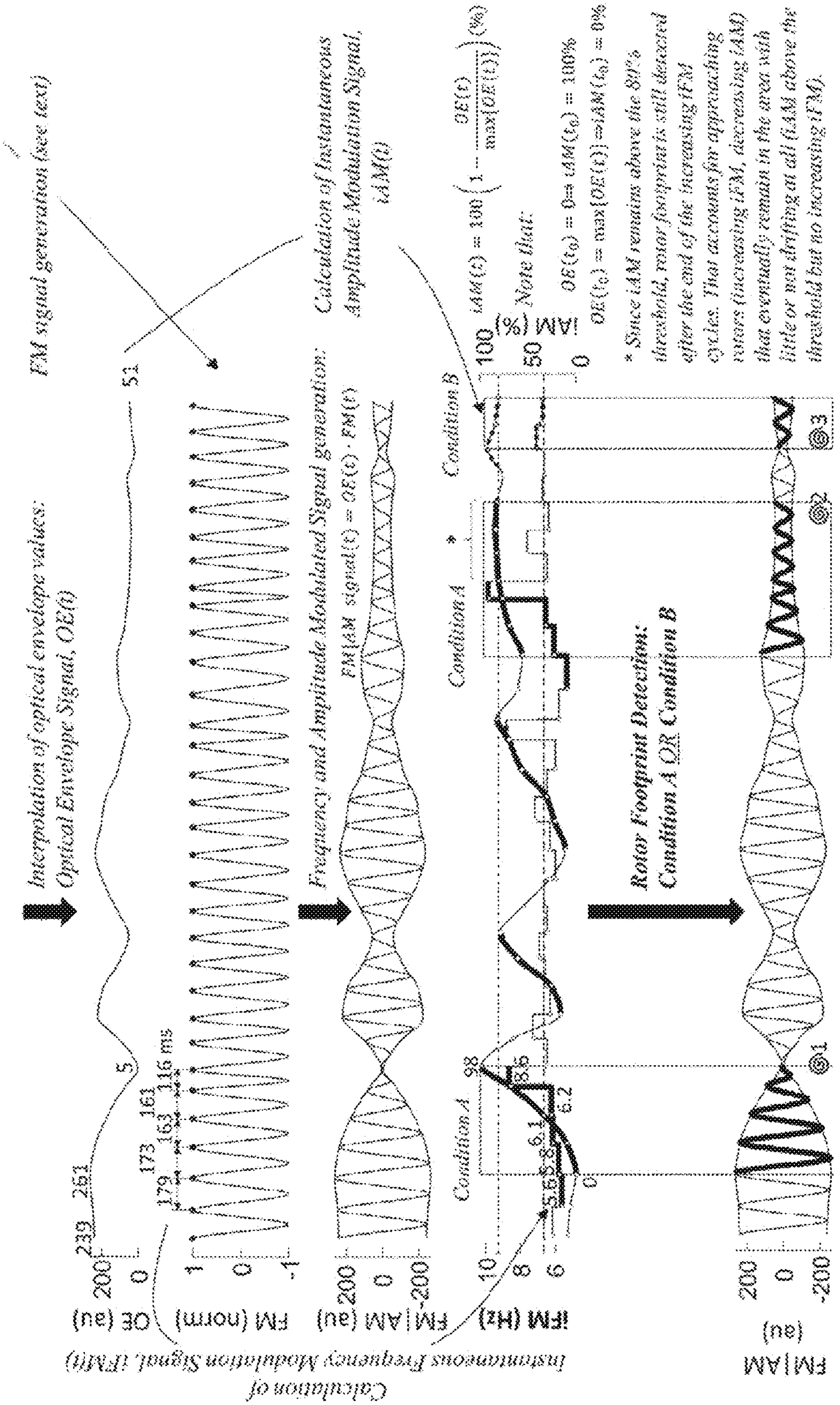

FIG. 3. Single-signal algorithm used with optical signals to calculate instantaneous frequency modulation (iFM) and detect rotational footprints based on the instantaneous amplitude and frequency modulations (iAM/iFM) contained in optical signals during AF. In this version of the algorithm, the minimum refractory period used to calculate activations in the time-domain is calculated from the dominant frequencies of the OAP and APS signals. The rest of the figure is self-explanatory. More details are provided in the text. APS: absolute positive slope signal, FM|AM: Frequency and amplitude modulated signal, FM: frequency modulated signal, iAM: Instantaneous amplitude modulation signal, IFM: Instantaneous frequency modulation signal, OAP: Optical action potentials, OE: optical envelope signal, PSD: power spectral density.

Figure 4:
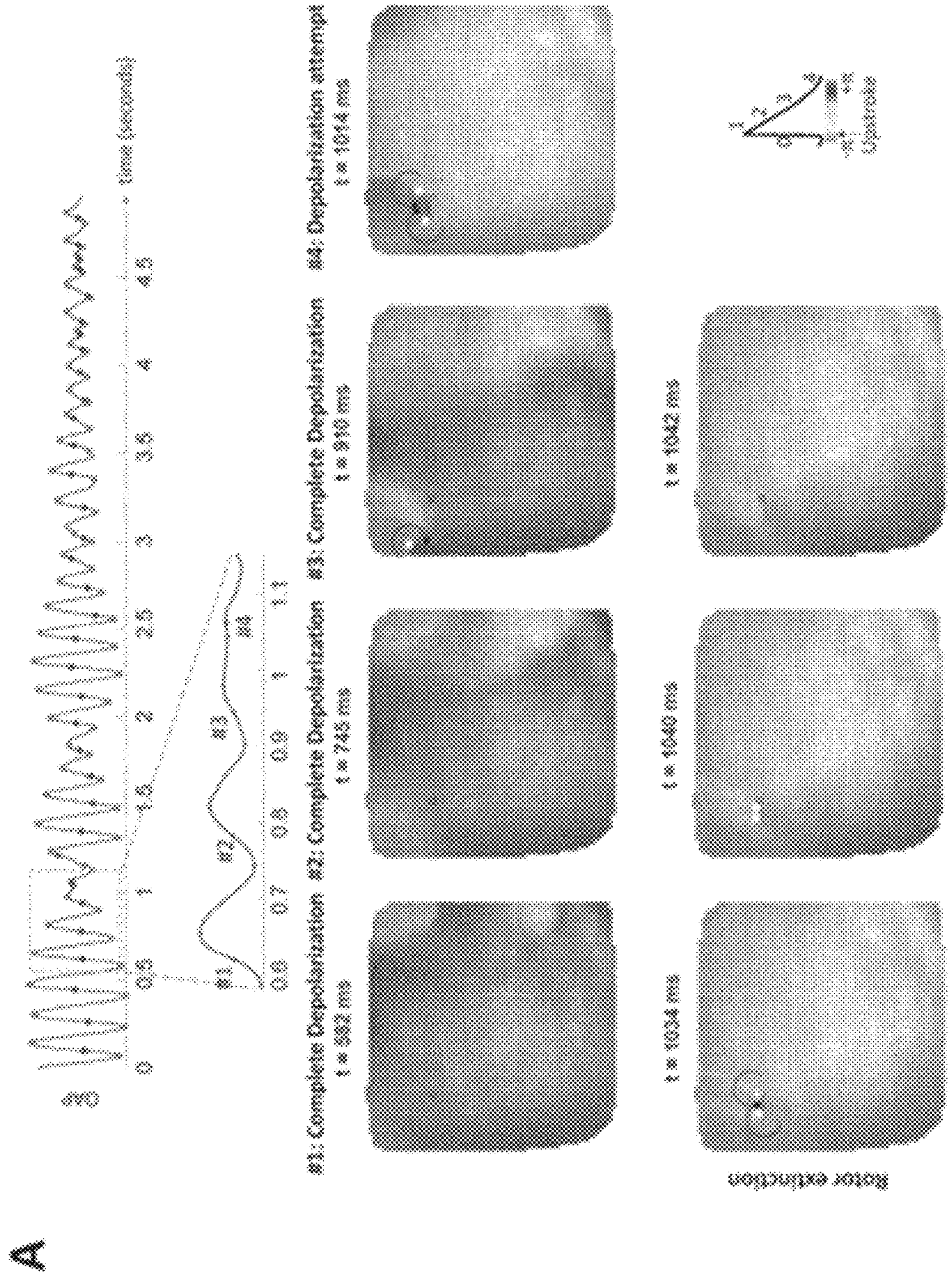
Figure 4:
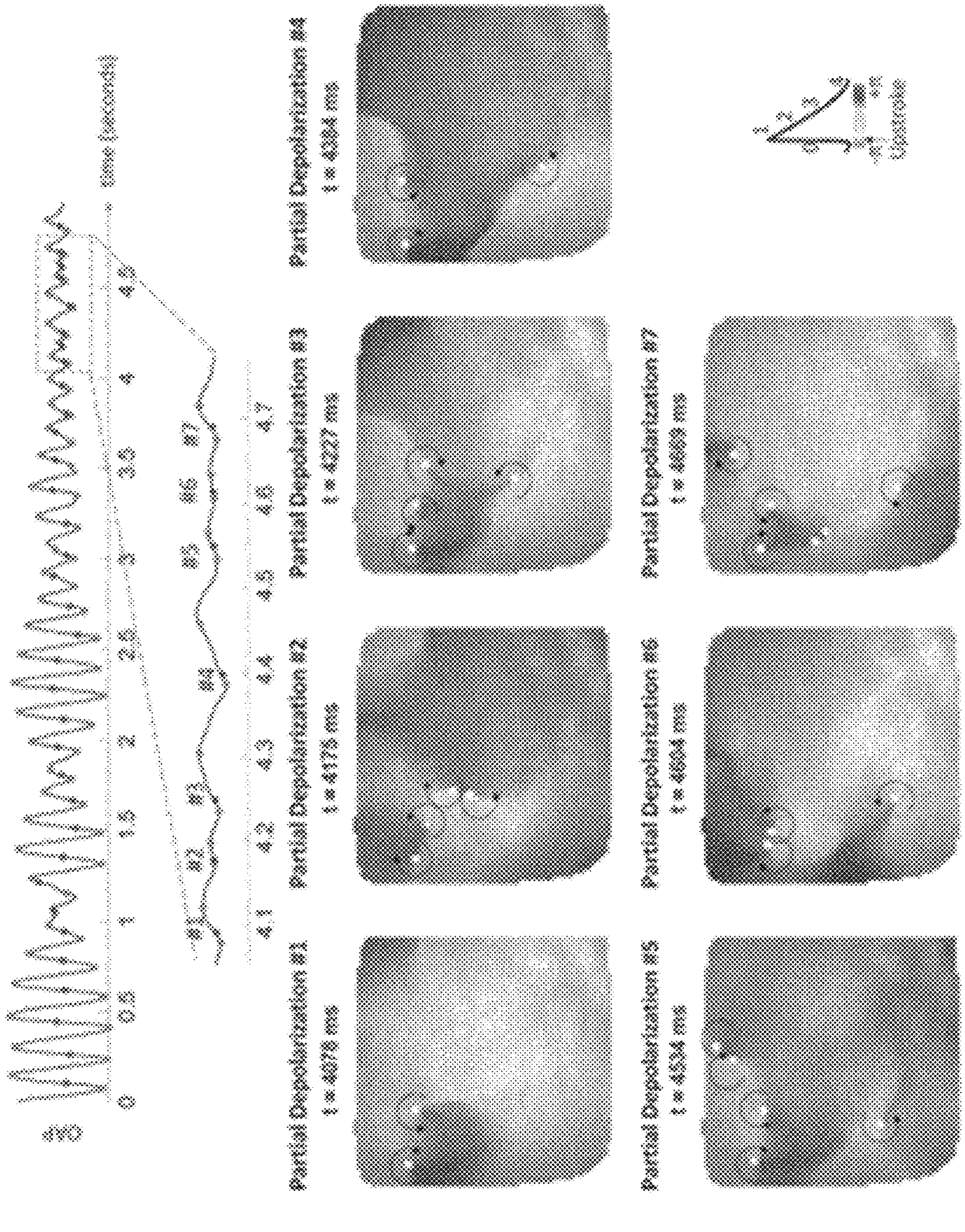

FIG. 4. Multiple depolarization attempts/partial depolarizations are present in an optical signal during the intervals in which phase singularities (white circles) meander through the pixel surroundings. They are the result of the rotational wavefront crossing the pixel in a seemingly very high non-physiological rate. Note that although the pixel is framed with a black square, it could be necessary to zoom in the figure to visualize it due to its tiny size. A. Three complete activations followed by a depolarization attempt in a short period of time before the figure-of-eight reentry terminated. B. Seven depolarization attempts/partial depolarizations in less than 600 ms, which could be considered as a non-physiological activation rate.

Figure 5:
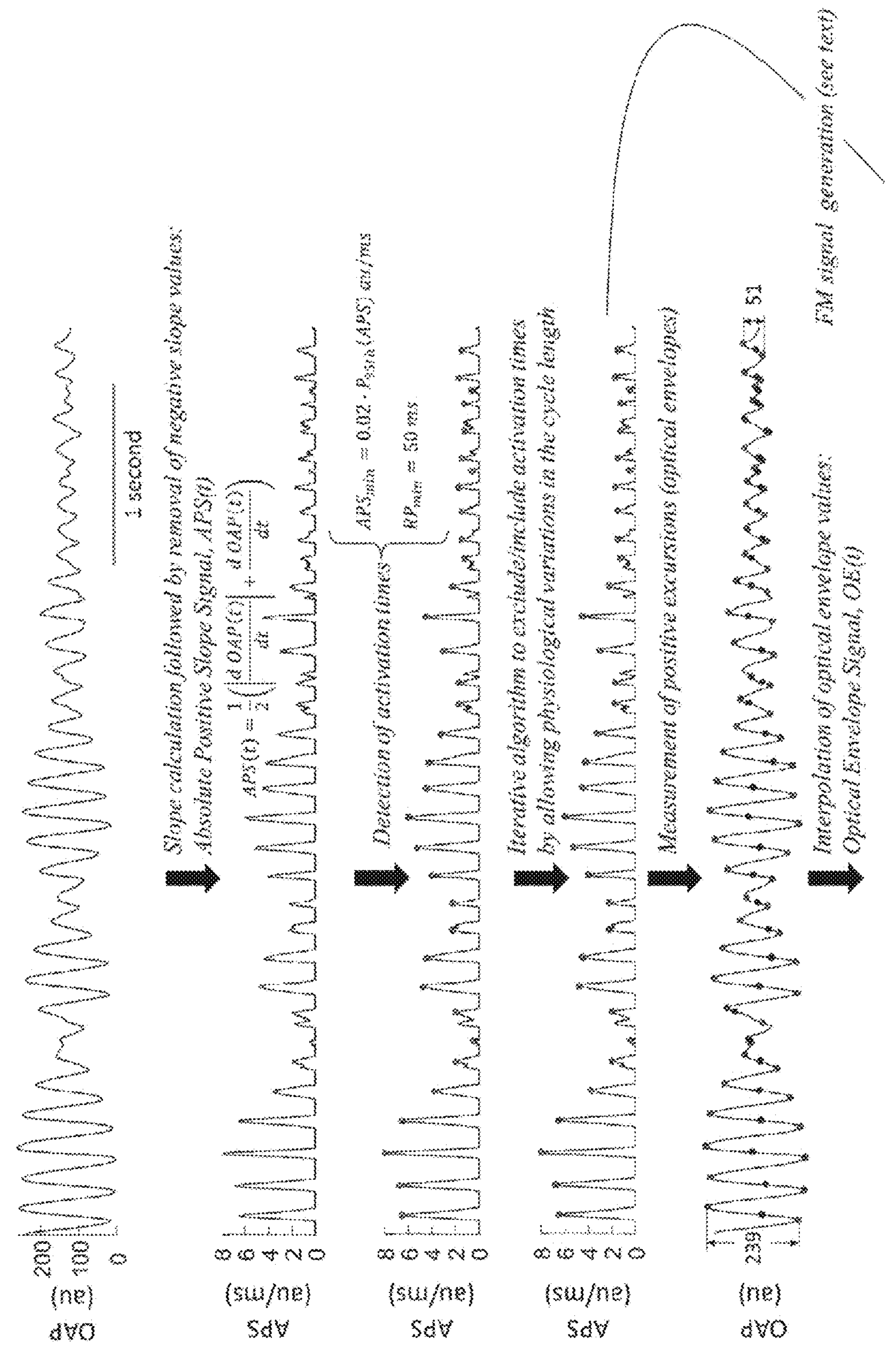
Figure 5:
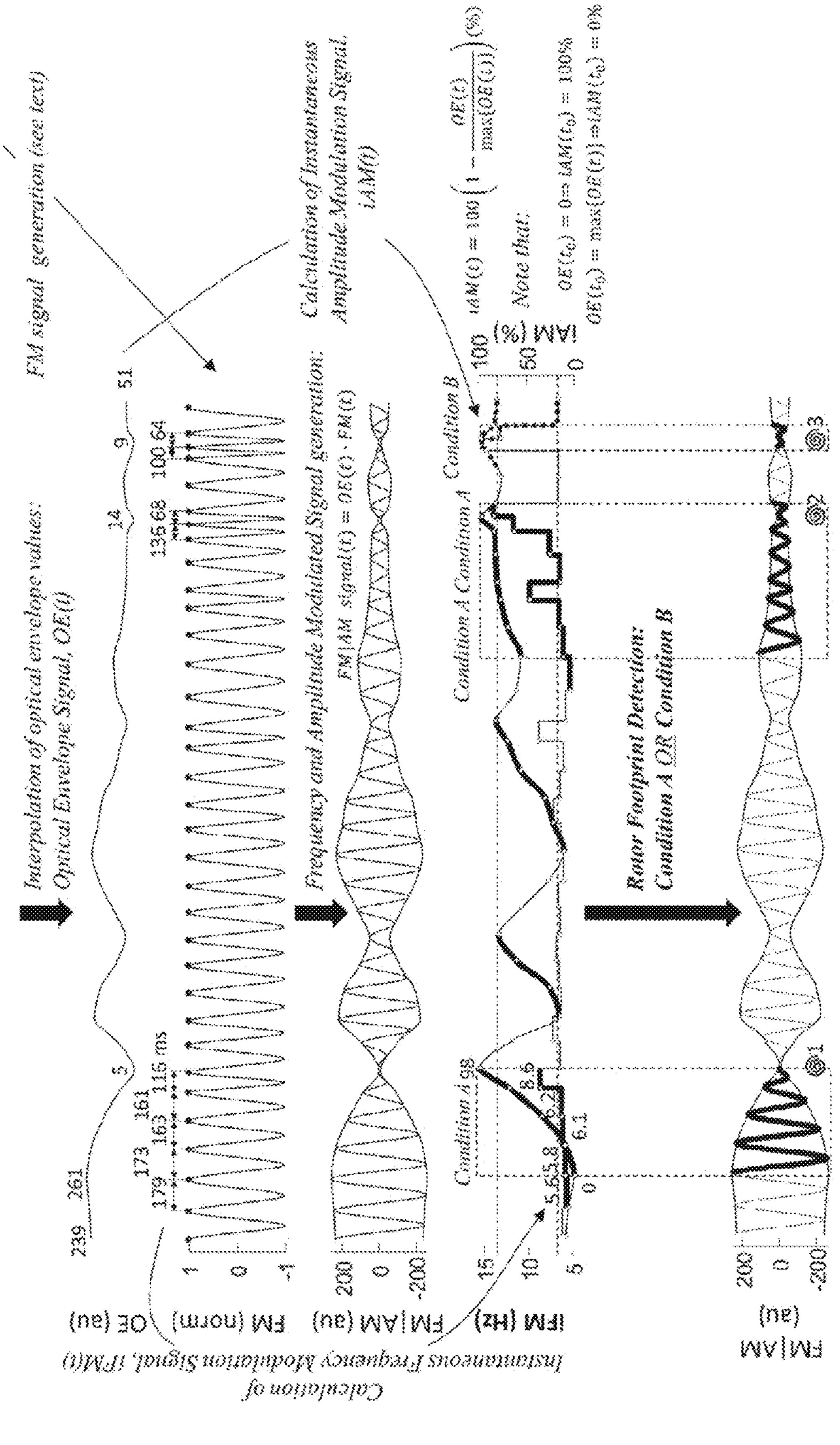

FIG. 5. Single-signal algorithm used with optical signals to calculate instantaneous frequency modulation (iFM) and detect rotational footprints based on the instantaneous amplitude and frequency modulations (iAM/iFM) contained in optical signals during AF. In this version of the algorithm, the minimum refractory period is fixed to 50 ms regardless the dominant frequencies of the OAP and APS signals. Thus, the algorithm is capable to account for high-rate seemingly non-physiological partial depolarizations like the ones shown in FIG. 4. This makes the detection of activations very sensitive, but potentially unspecific. The rest of the figure is auto-explanatory. More details are provided in the text. Acronyms as in FIG. 3.

Figure 6:
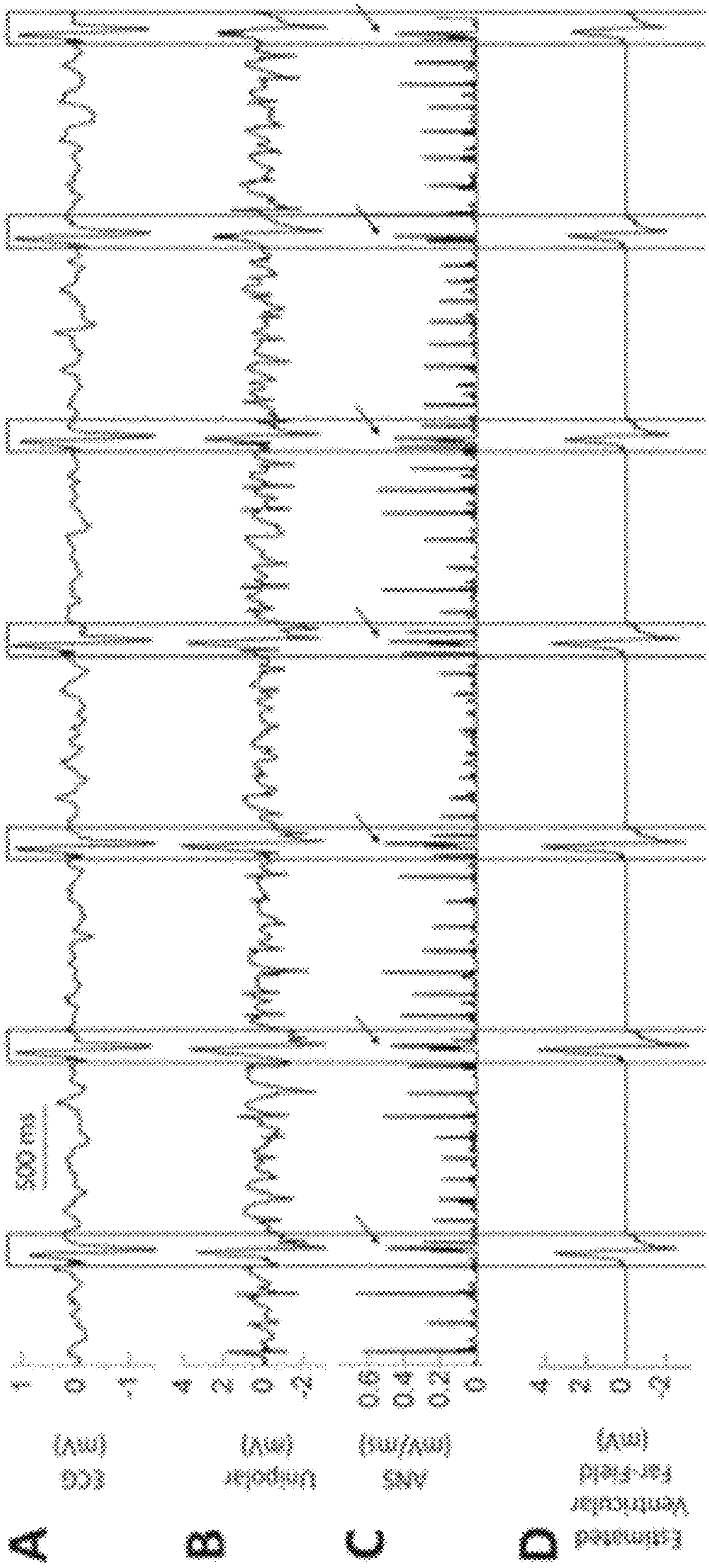
Figure 6:
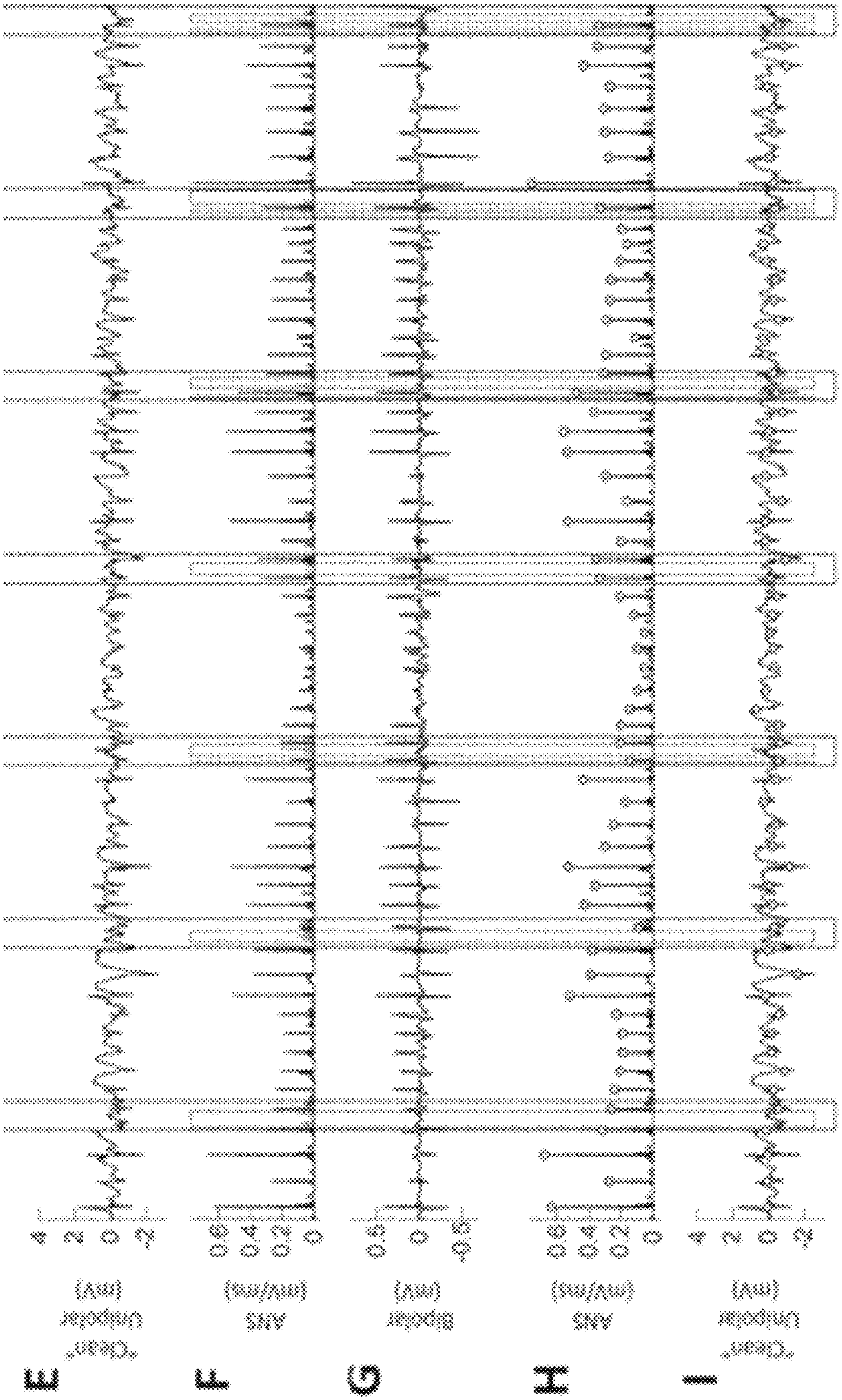

FIG. 6. Ventricular far-field rejection algorithm used to accurately detect atrial activations. A. Surface ECG signal. QRS complexes are highlighted in orange and stimulation artifacts in cyan. The grey intervals are the ones in which the rejection algorithm will be applied. B. Raw unipolar signal from the coronary sinus with clear ventricular far-field. C. Absolute Negative Slope (ANS) signal that will be later used to detect activation times. The red arrows display the spurious peaks generated by the negative deflections of the ventricular far-field. Some of them may actually be simultaneous with true atrial activations. D. A ventricular far-field signal is estimated using Principal Component Analysis (PCA). See details in text. E. Unipolar signal after subtraction of the estimated ventricular far-field in D. F. ANS is calculated again from the 'clean' unipolar signal shown in E. Note that some residual negative slope ventricular activity is still present (in red). G. Then, the corresponding bipolar signal is analyzed during the grey intervals and the negative slope activity in F between atrial activations in the bipolar signal (time intervals with green background) is removed because it would very likely correspond to residual ventricular activity. H. Negative slope activity during green intervals is removed from ANS prior to detecting activations as the times with the maximum negative slopes (see FIG. 9 for more details about detecting activations). I. 'Clean' unipolar signal with cyan dots marking the activation times detected in the ANS shown in H.

Figure 7:
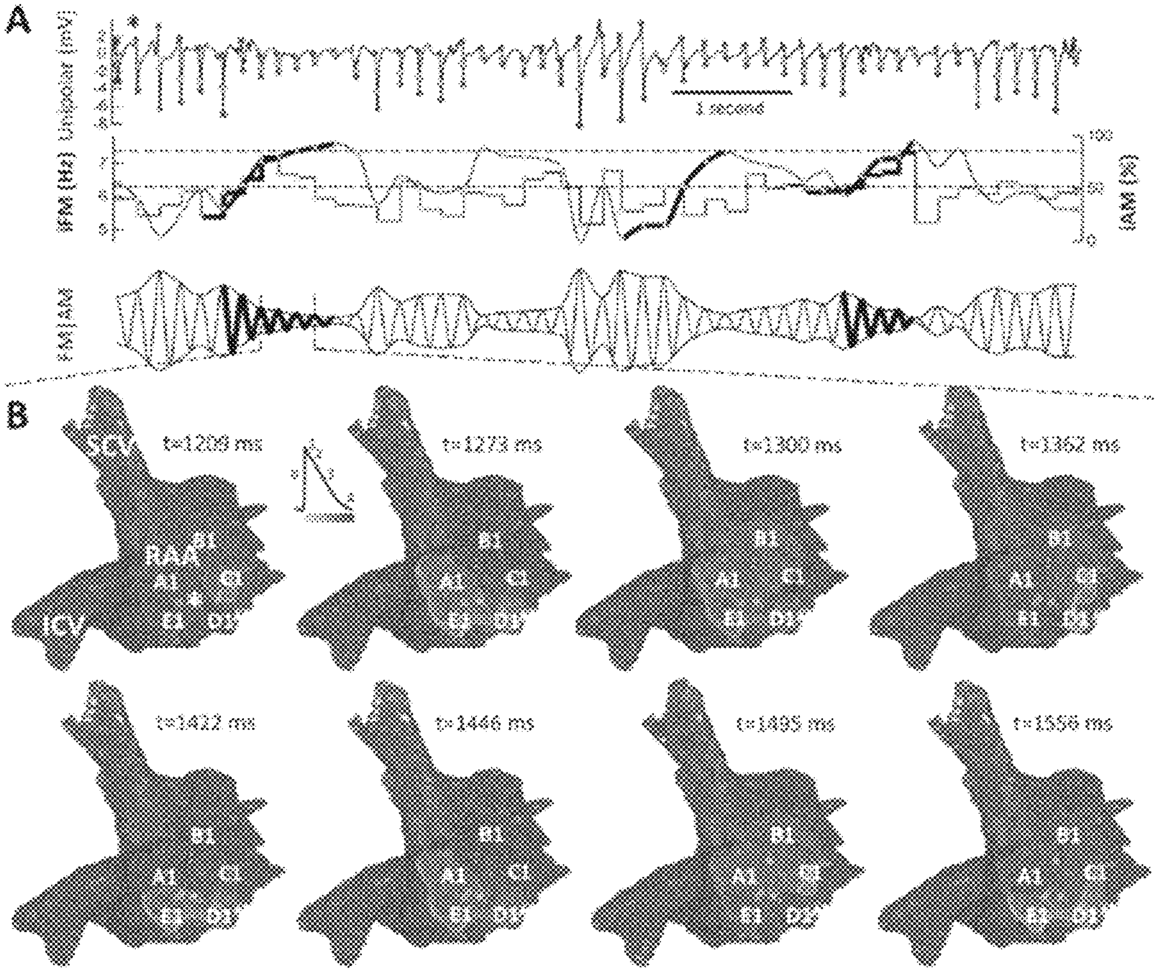
Figure 7:
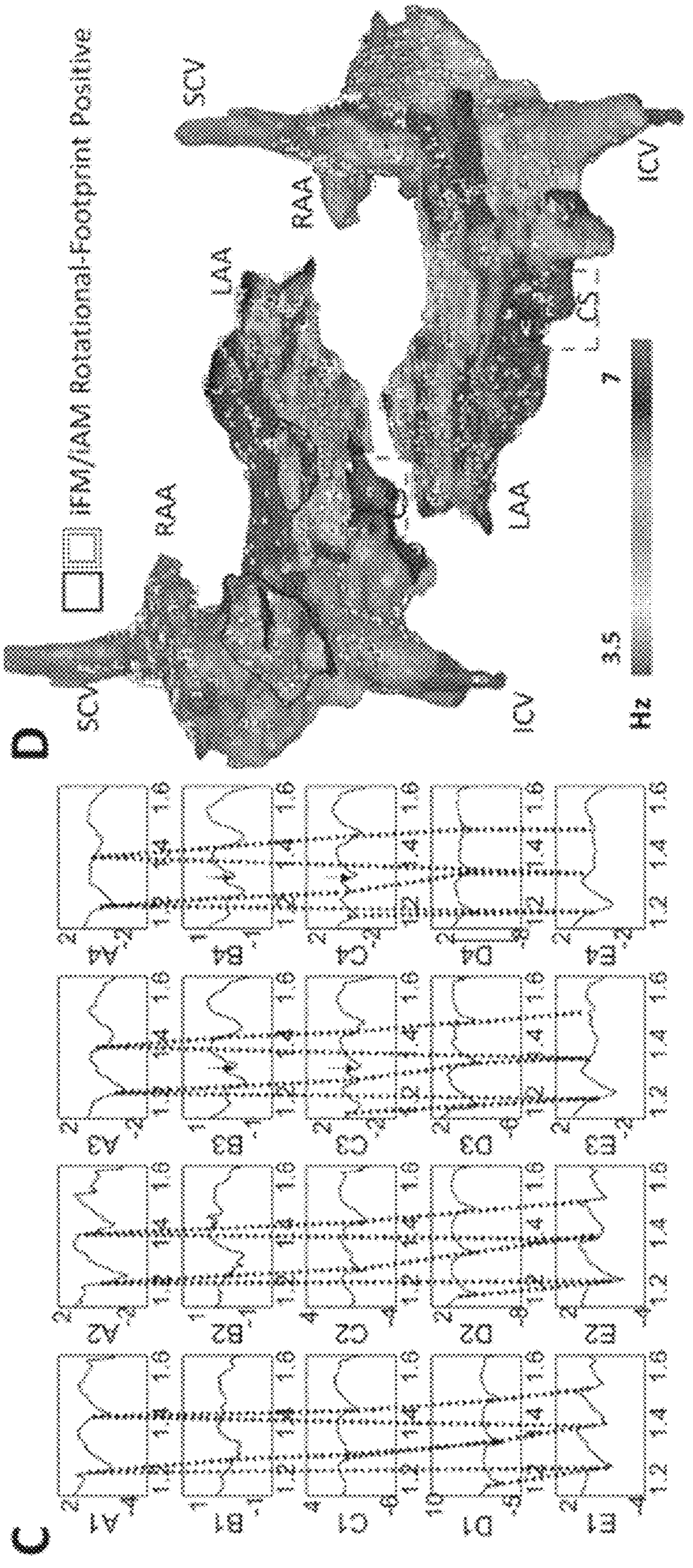

FIG. 7. In-vivo iFM and iAM calculation and single-signal rotational-footprint detection from unipolar electrical signals. A. Activation times (first row, cyan points) were used to generate the iFM signal (second row, cyan tracing). Amplitude excursions between the starts and ends of negative deflections (first row, red points) were used to generate the iAM signal (second row, red tracing). Time intervals with sustained simultaneously increasing iFM (thick cyan) and iAM (thick red) reaching a pre-specified threshold (85% in this example, dotted horizontal red line) are detected. Therefore, this electrode location was marked as 'rotational-footprint positive'. Third row displays a synthetic FM IAM signal that resembles the corresponding optical action potentials. 'Rotational-footprint positive' intervals are highlighted (thick cyan). B. Snapshots from the phase movie obtained by interpolating data from the 20 electrodes of a PentaRay catheter fully deployed in the RAA. 'Rotational-footprint positive' electrode locations are highlighted with cyan squares. Note the high correlation between highlighted electrodes and the center of rotation in the phase movie. C. Unipolar electrograms confirming the rotational activation displayed in C. Red arrows mark partial depolarizations that may be explained by precession of the rotational core (FIG. 4). D. Combined hierarchy ($iFM_{median}$)+rotational-footprint maps. 'Rotational-footprint positive' locations are marked with black or white squares to easy visualization within light/dark areas respectively. Note that, even though many regions displayed repetitive rotational activations, including the RAA and LAA, most of them were not hierarchically relevant to drive AF since it acutely terminated and was not inducible after only ablating the purple area located in the coronary sinus. Importantly, rotational-footprints were also found in that region. Asterisks mark the location from which the signal in A was retrieved. CS: coronary sinus, ICV: inferior cava vein, LAA: left atrial appendage, RAA: right atrial appendage, SCV: superior cava vein.

Figure 8:
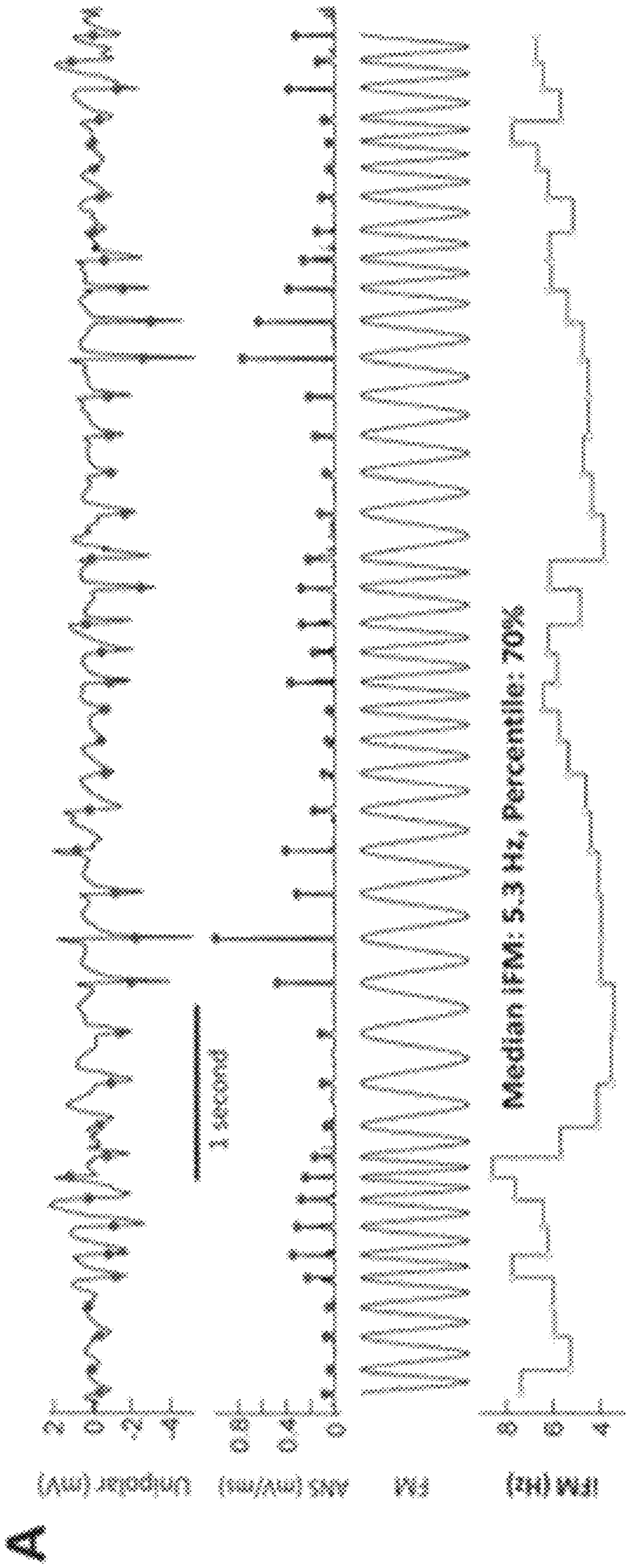
Figure 8:
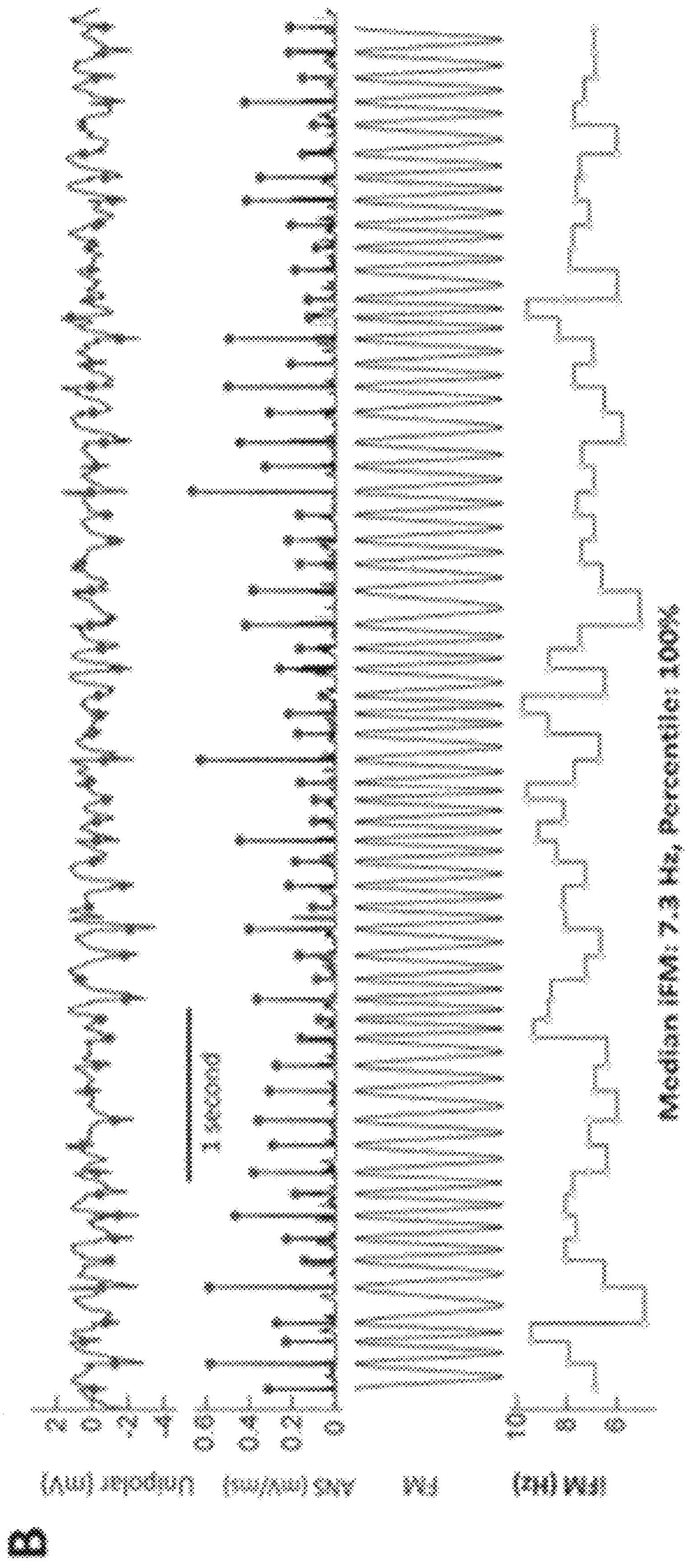
Figure 8:
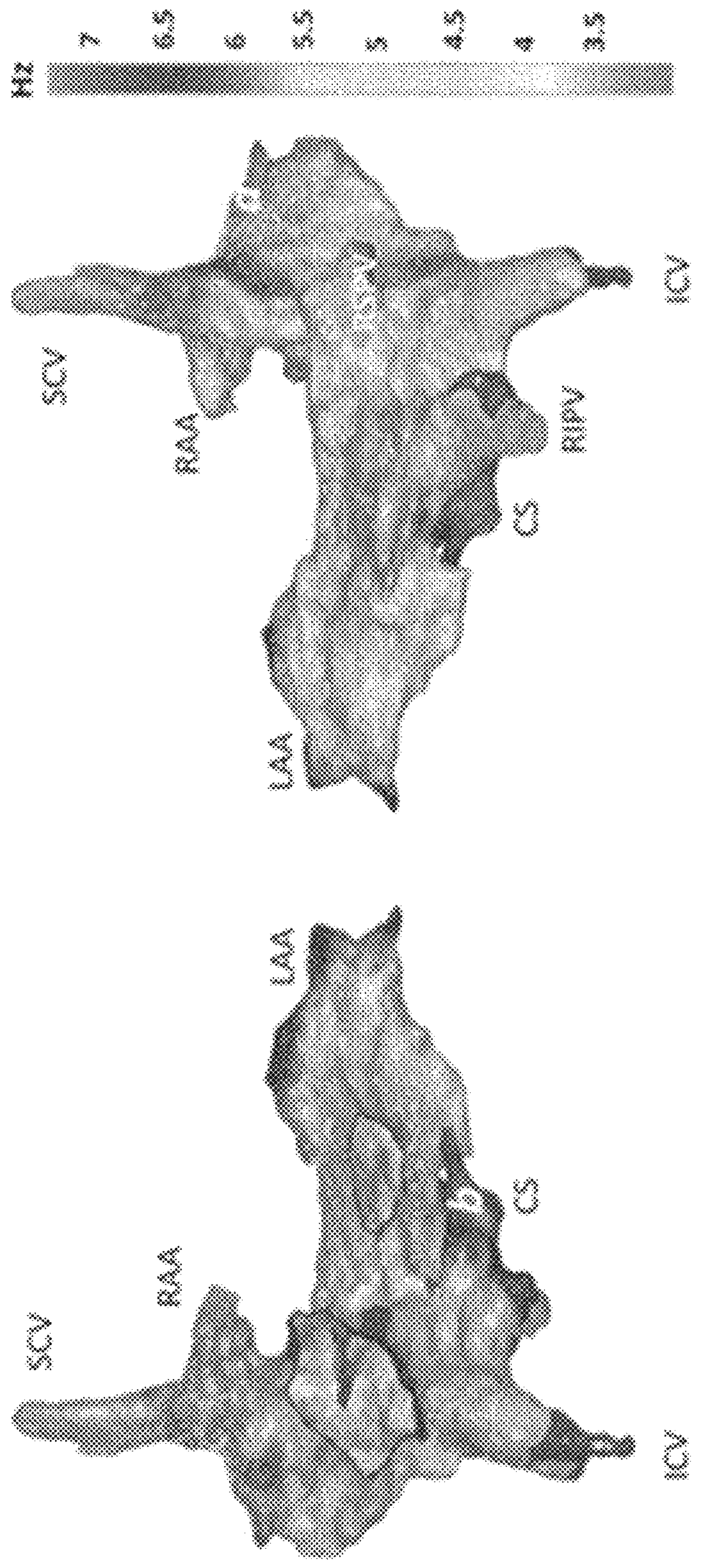
Figure 13:
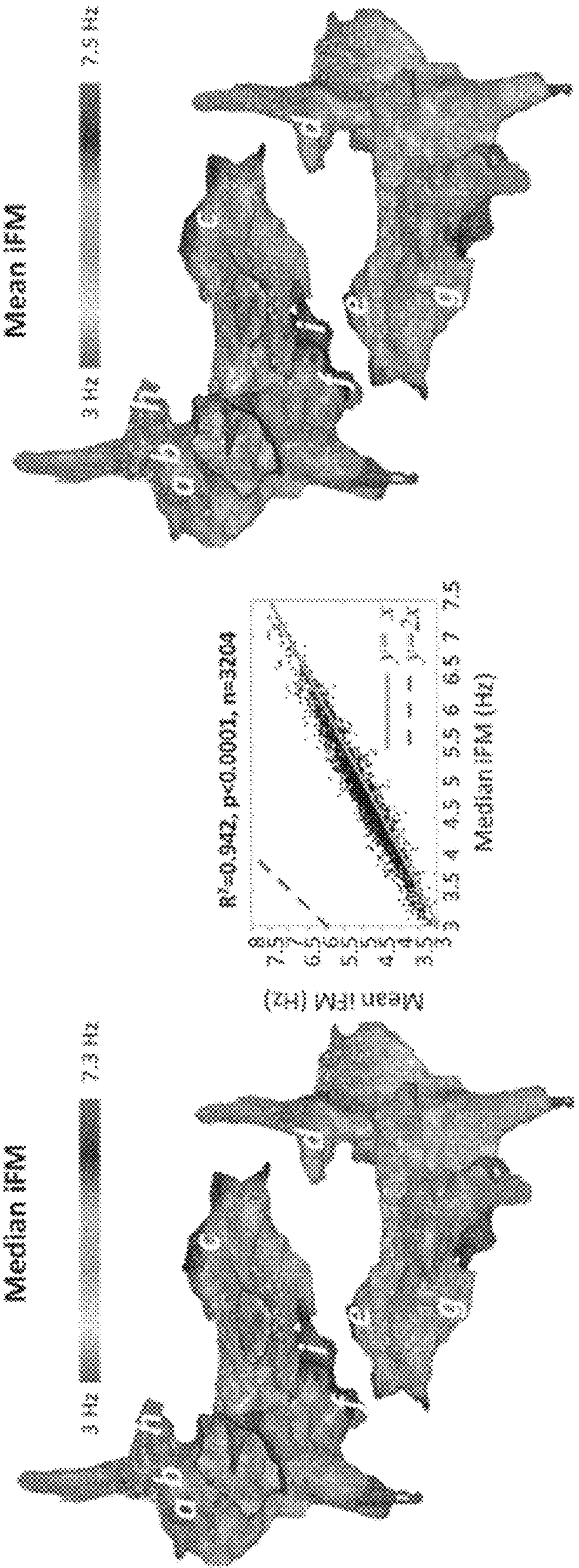
Figure 13:
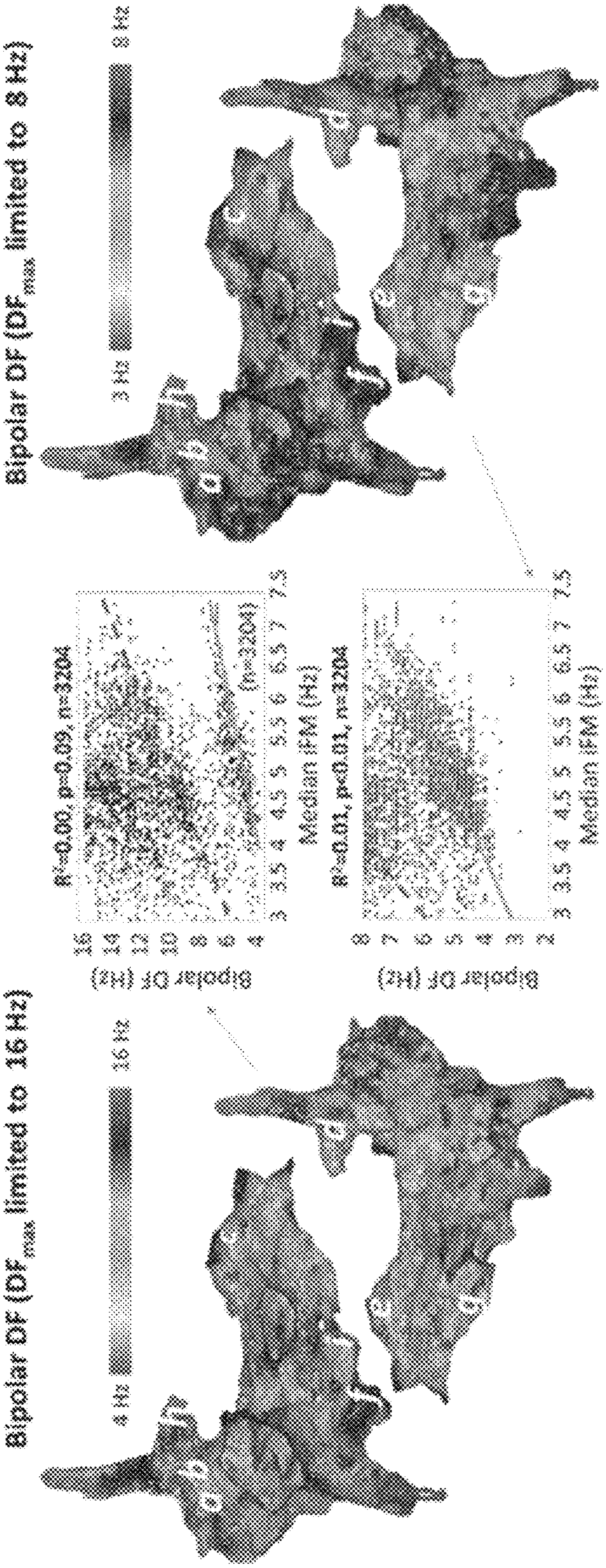
Figure 13:
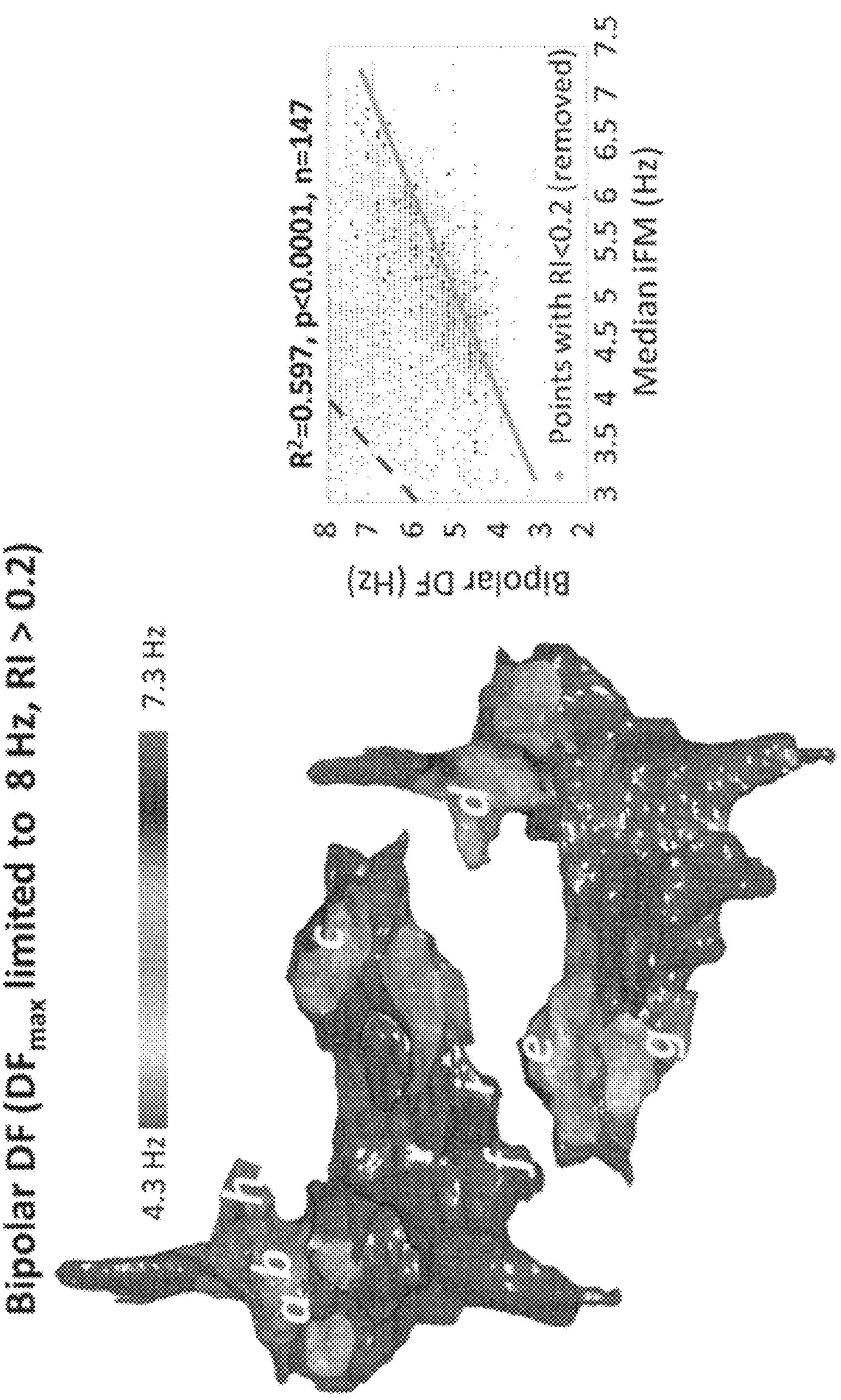
Figure 14:
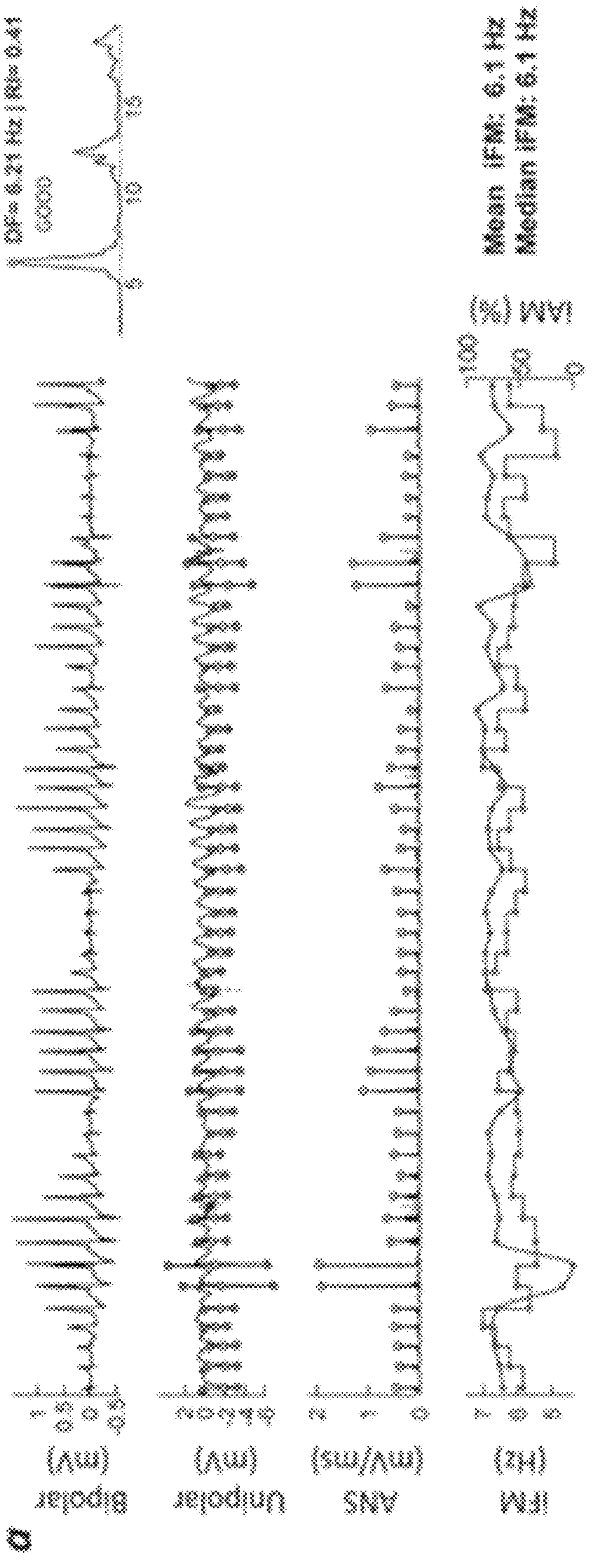
Figure 14:
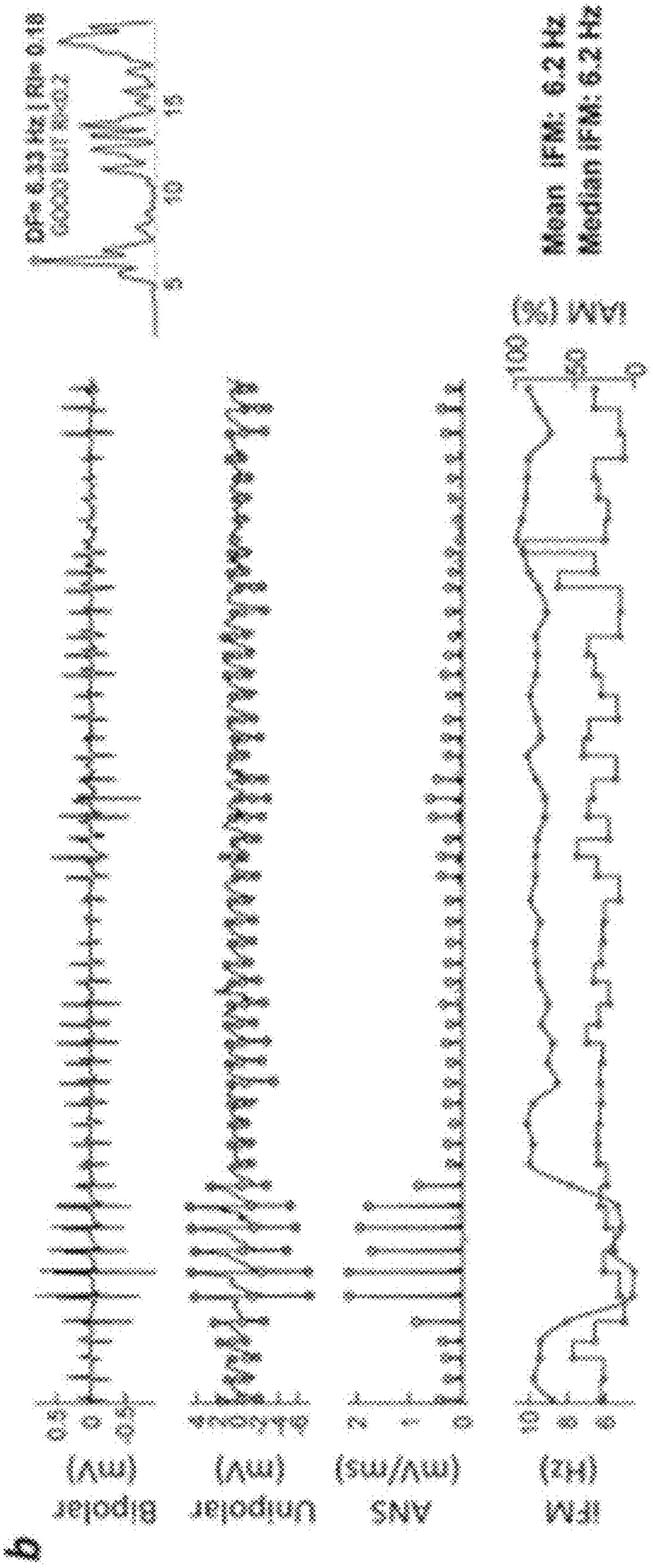
Figure 14:
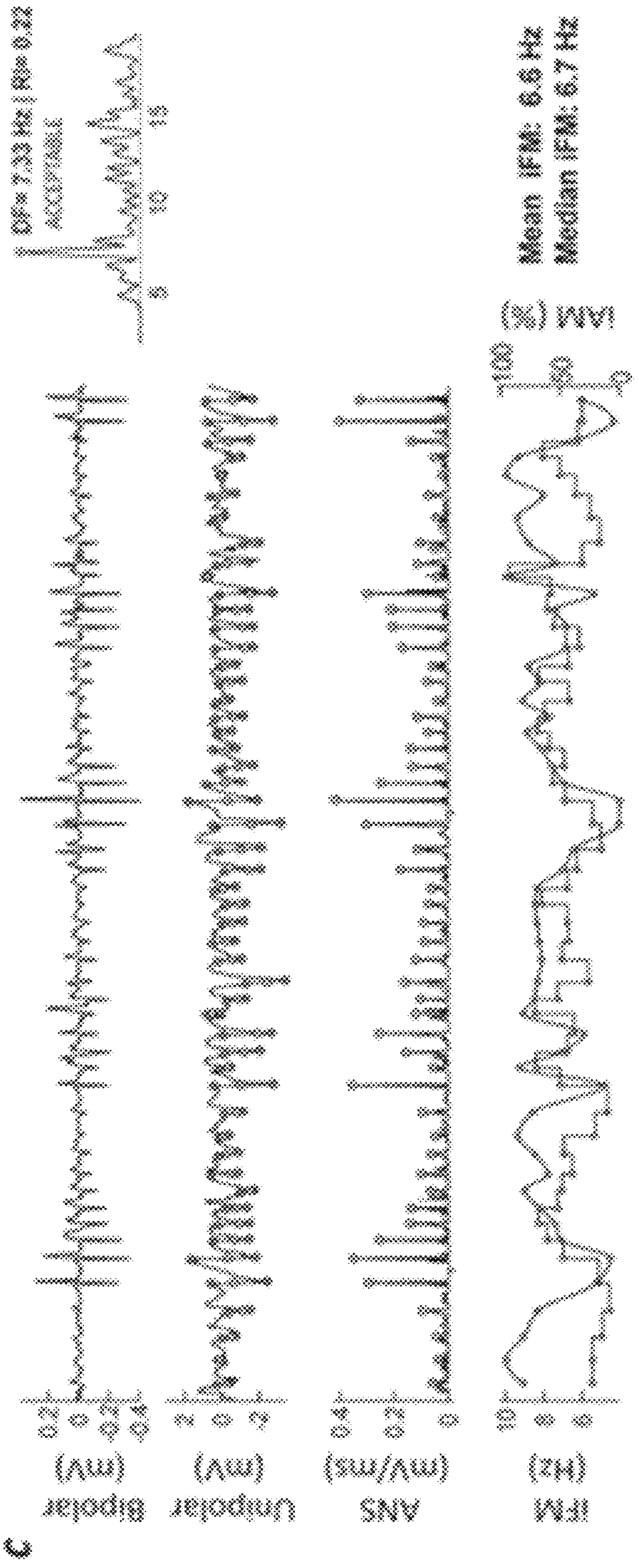
Figure 14:
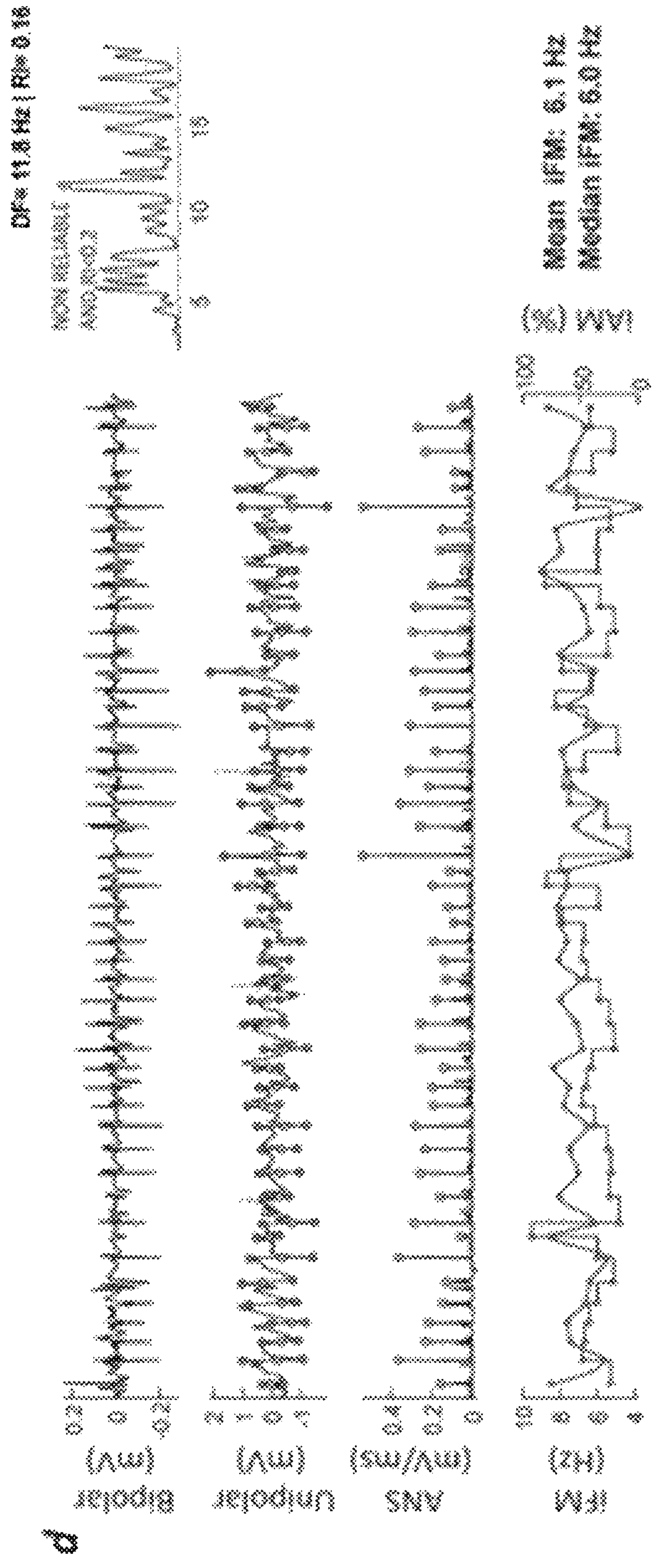
Figure 14:
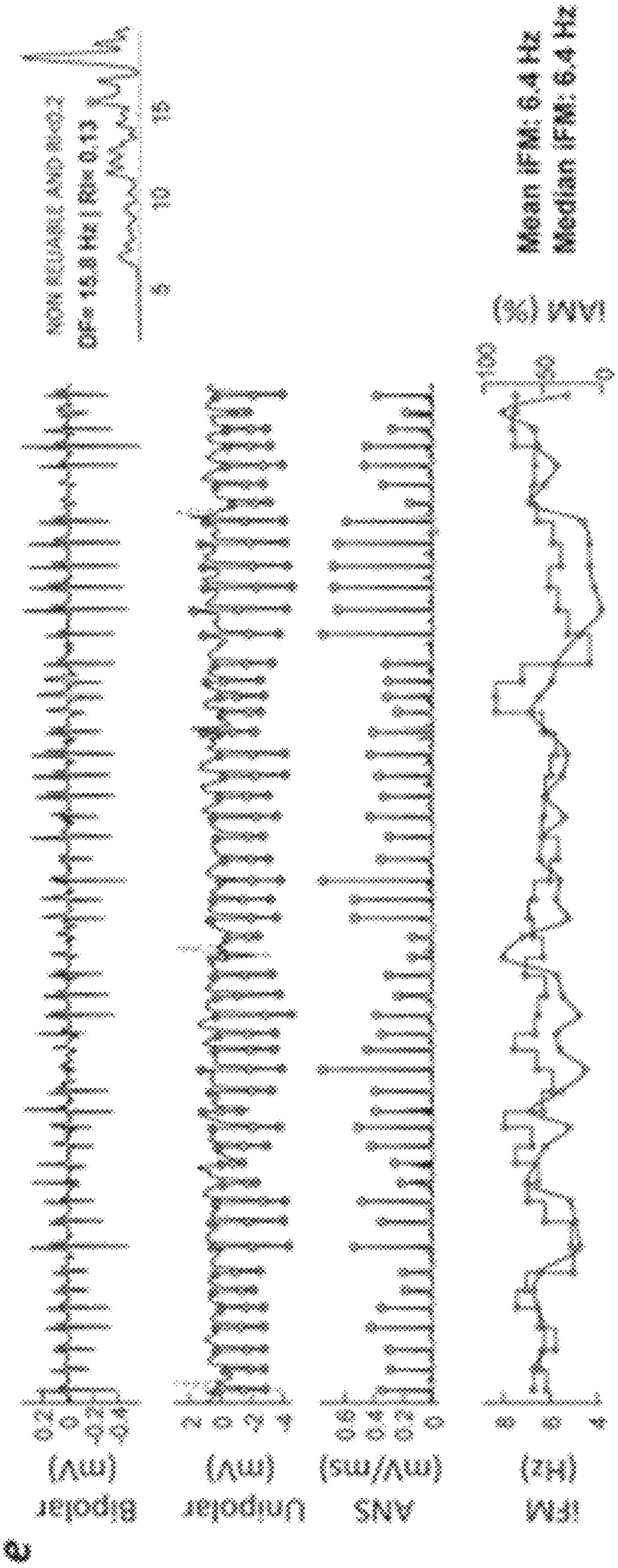
Figure 14:
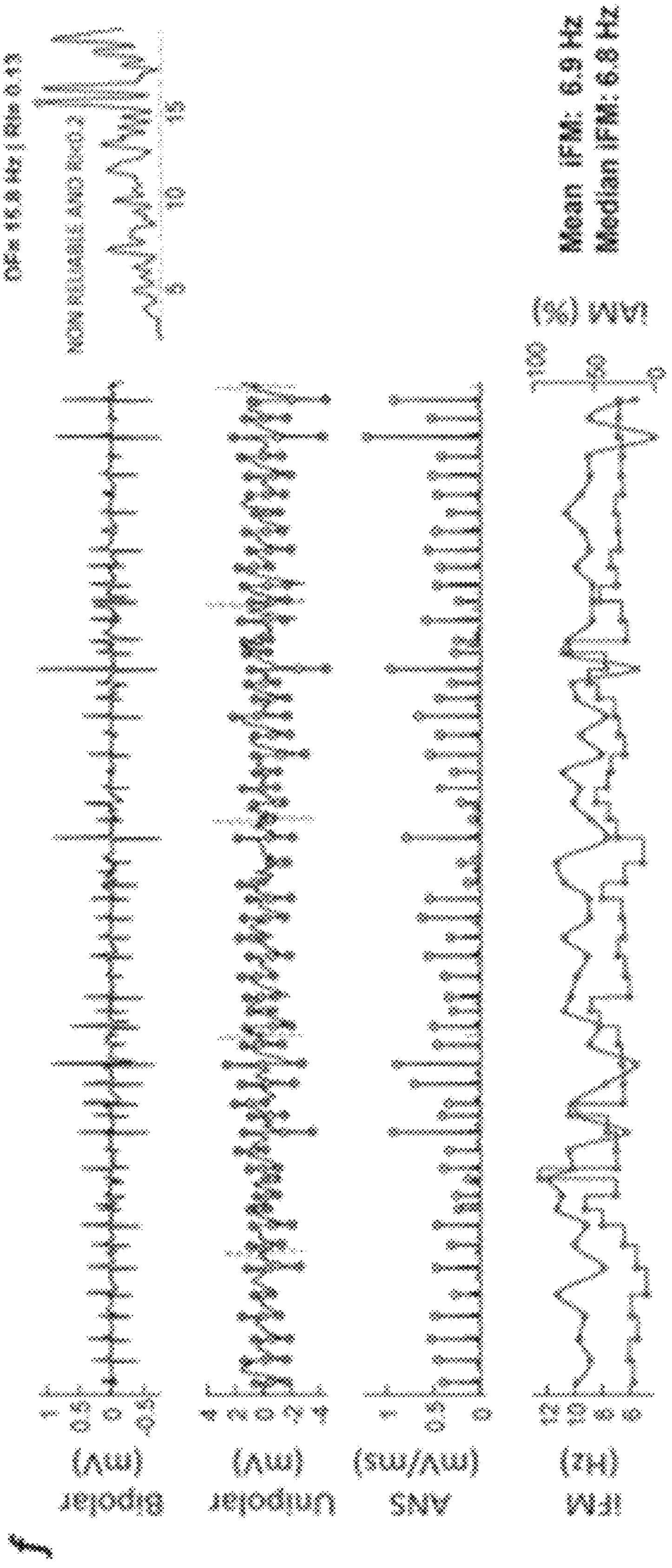
Figure 14:
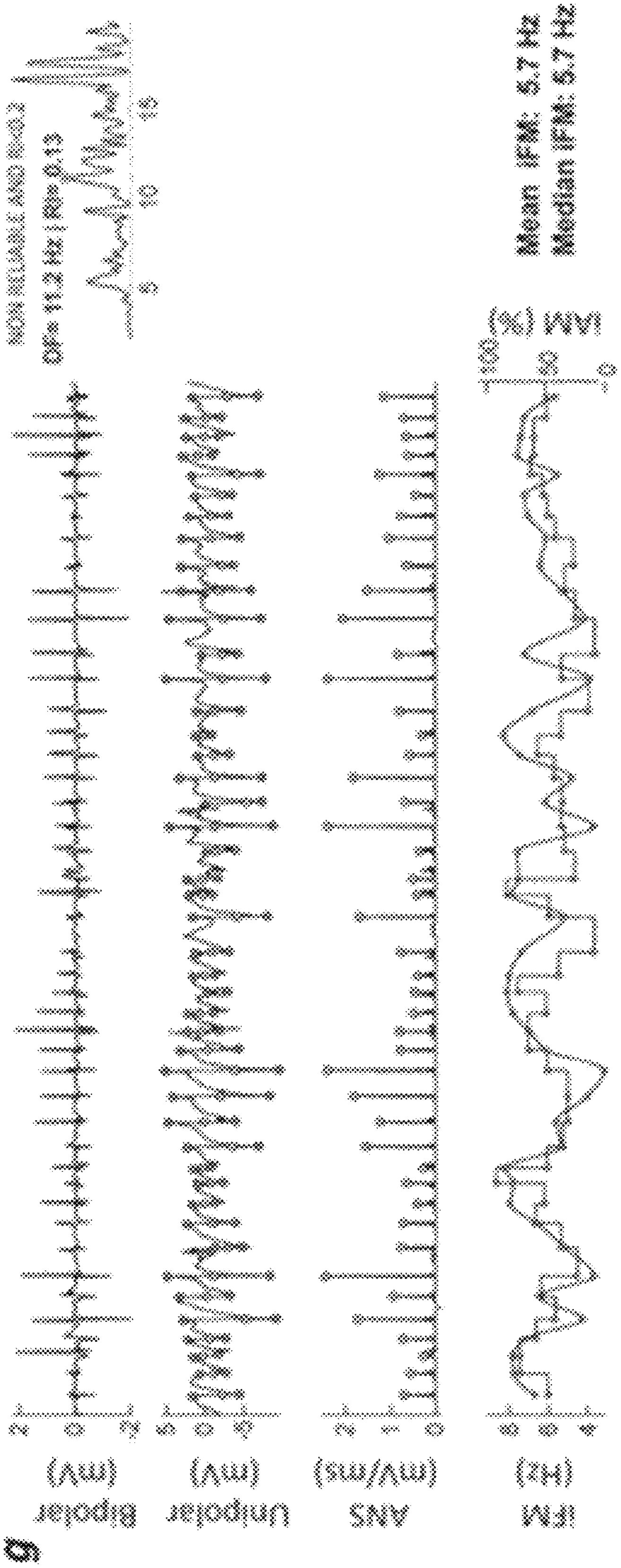
Figure 14:
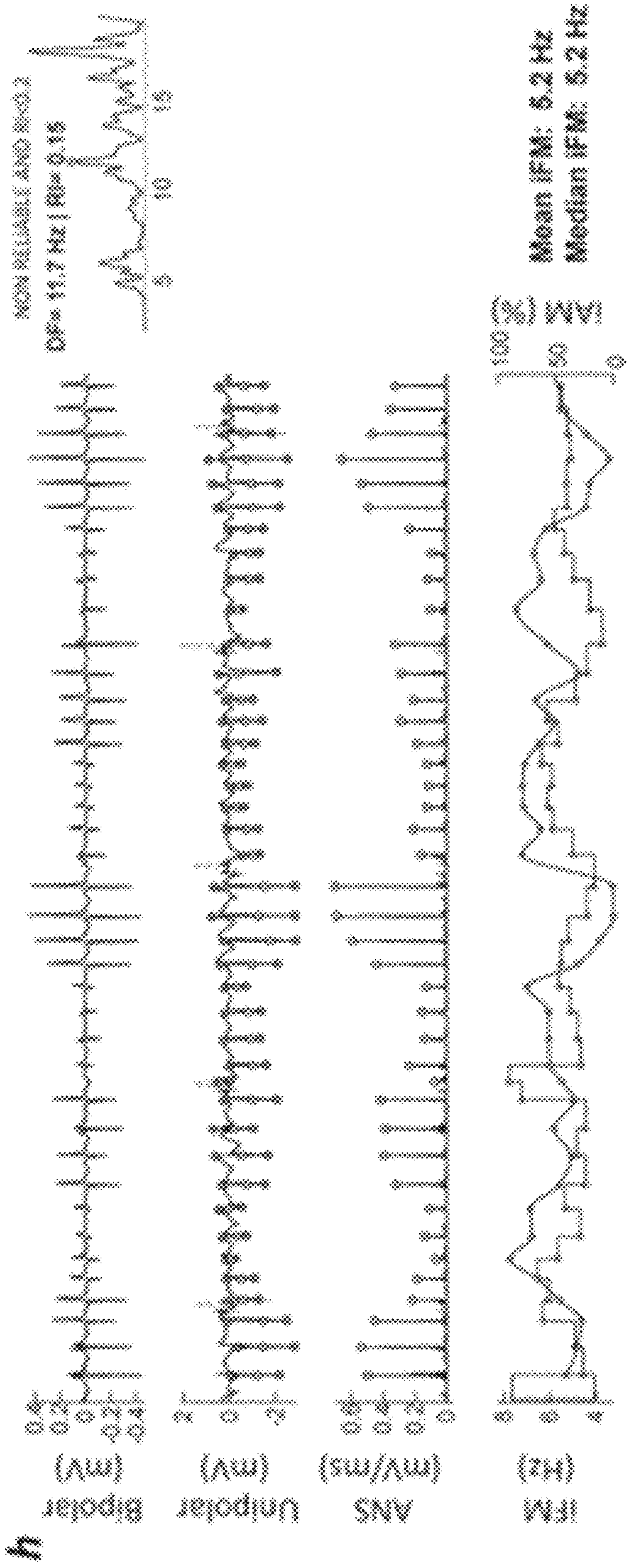
Figure 14:
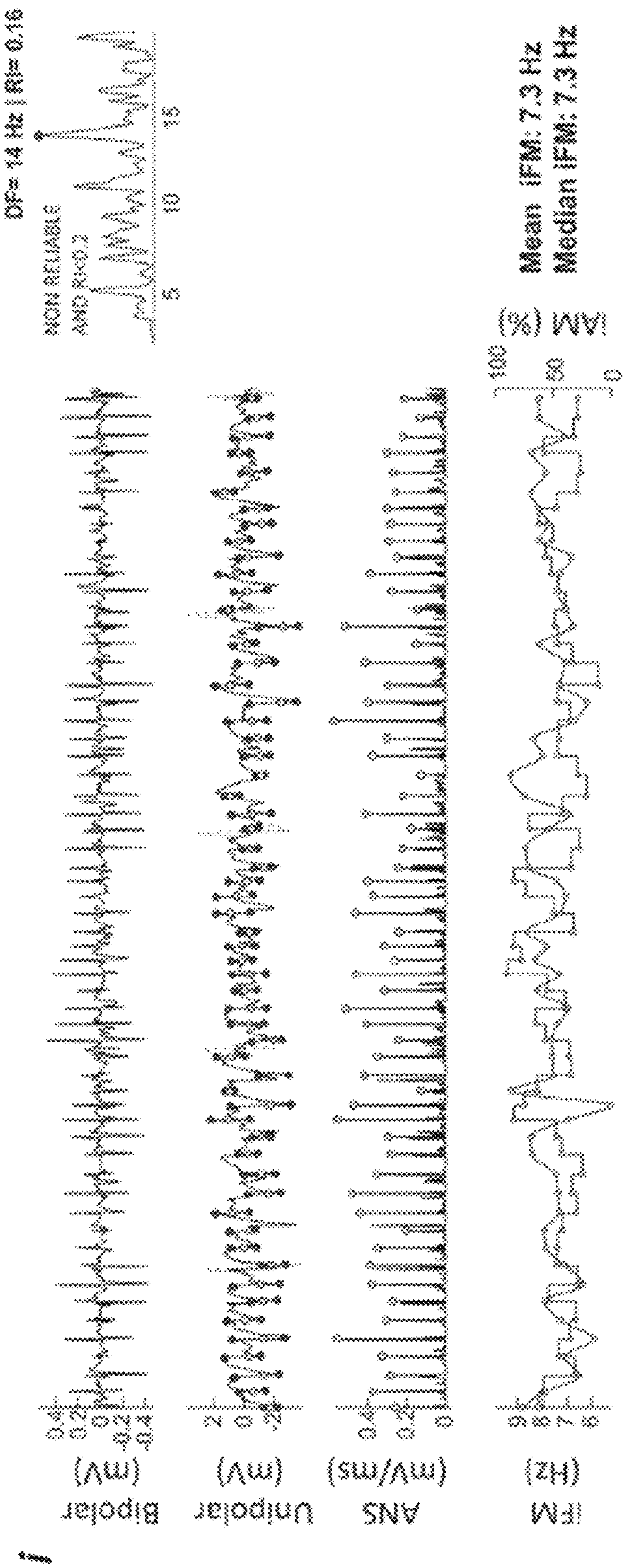

FIG. 8. Generation of median instantaneous frequency modulation (iFM) maps from in-vivo electroanatomical data in a pig with persistent AF (PsAF) to detect 'driver' regions. A. Top row: unipolar signal from the RAA ('a' in panel C). Local activation times are detected on the Absolute Negative Slope (ANS) signal (orange tracing) using the algorithm detailed in FIG. 9. This activation times and their separations are used to create a sinusoidal frequency modulated signal (FM, arbitrary units) and the iFM signal (measured in Hz). The median value of the latter signal is used as a measure of the hierarchy level of that specific spatial location within the atria during the fibrillation process (5.3 Hz, $70^{th}$ percentile). B. Top row: unipolar signal from the CS ('b' point in panel C) after ventricular far-field minimization. Red arrows mark the residual negative slope activity. See FIG. 6 for more details about the ventricular far-field rejection algorithm. Again, the median value of the iFM signal is used as a measure of the hierarchy level of that specific spatial location (7.3 Hz, maximum value) within the atria during the fibrillation process. C. Driver map obtained by interpolating the median iFM values at the 3204 points used to generate it (small white dots). 'Islands' with high iFM median values are considered drivers. Left: anterior view. Right: posterior view. CS: coronary sinus, ICV: inferior cava vein, LAA: left atrial appendage, RAA: right atrial appendage, RSPV: right superior pulmonary vein, SCV: superior cava vein. FIGS. 13-14 show the similarities and differences between the presented iFM approach and previous attempts to quantify hierarchy during atrial fibrillation by Dominant Frequency.

Figure 9:
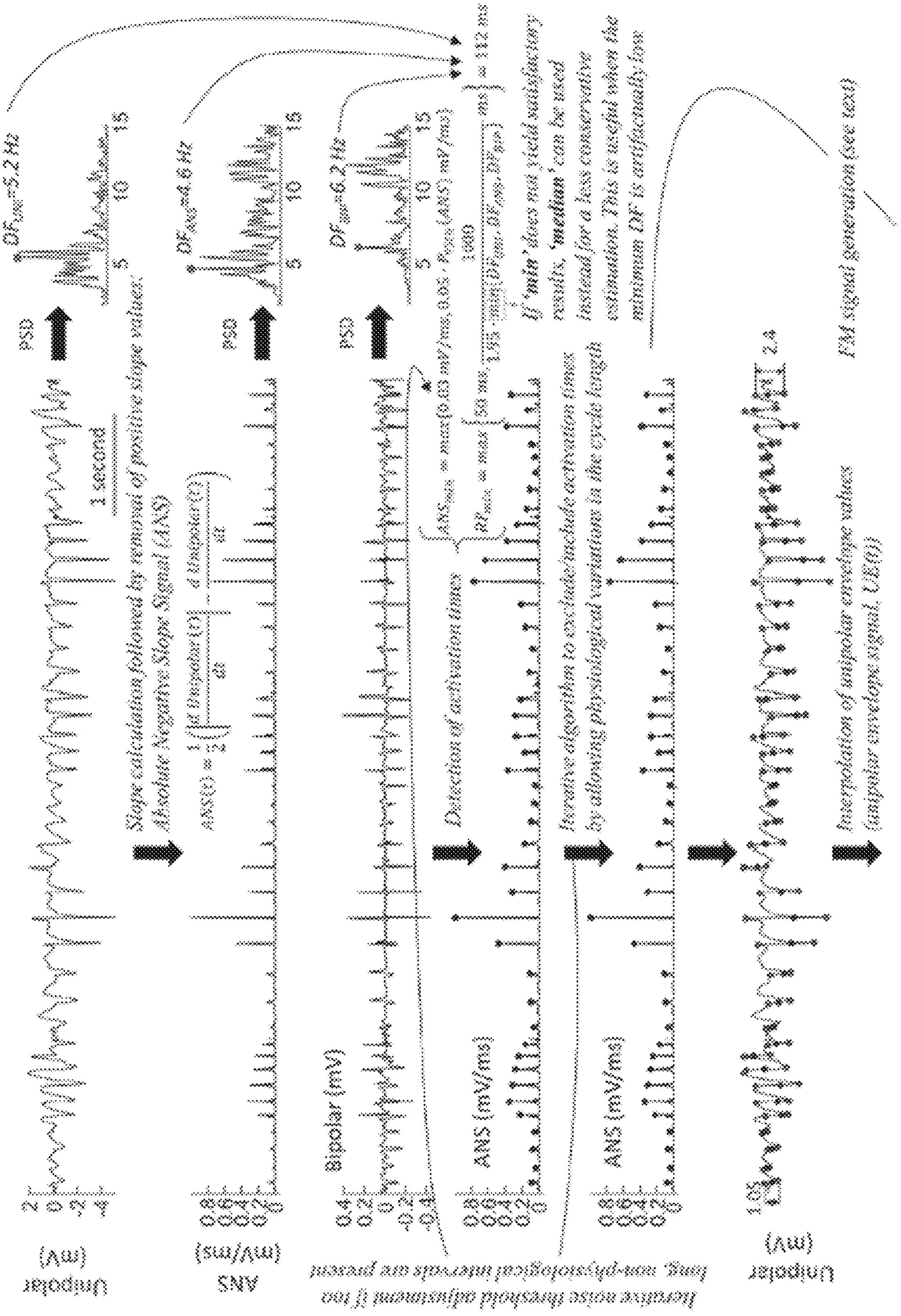
Figure 9:
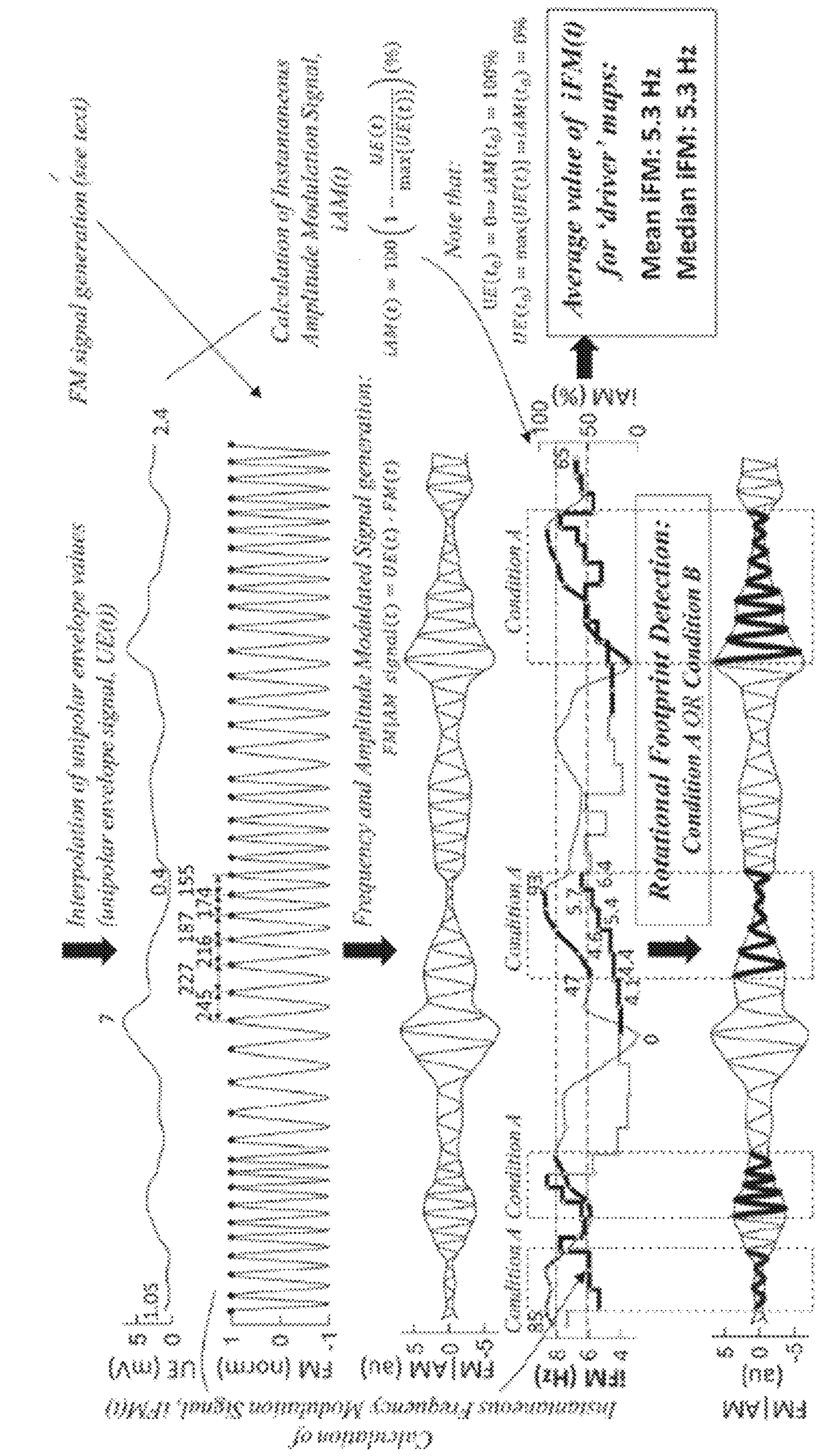

FIG. 9. Single-signal algorithm used with unipolar electrical signals for calculation of the instantaneous frequency modulation (IFM) and detection of rotational footprints based on the instantaneous amplitude and frequency modulations (iAM/iFM) contained in electrical unipolar signals during in-vivo AF. More details are provided in the text. ANS: absolute negative slope, FM|AM: Frequency and amplitude modulated signal, FM: frequency modulated signal, IAM: Instantaneous amplitude modulation signal, iFM: Instantaneous frequency modulation signal, PSD: power spectral density, UE: unipolar envelope signal.

Figure 10:
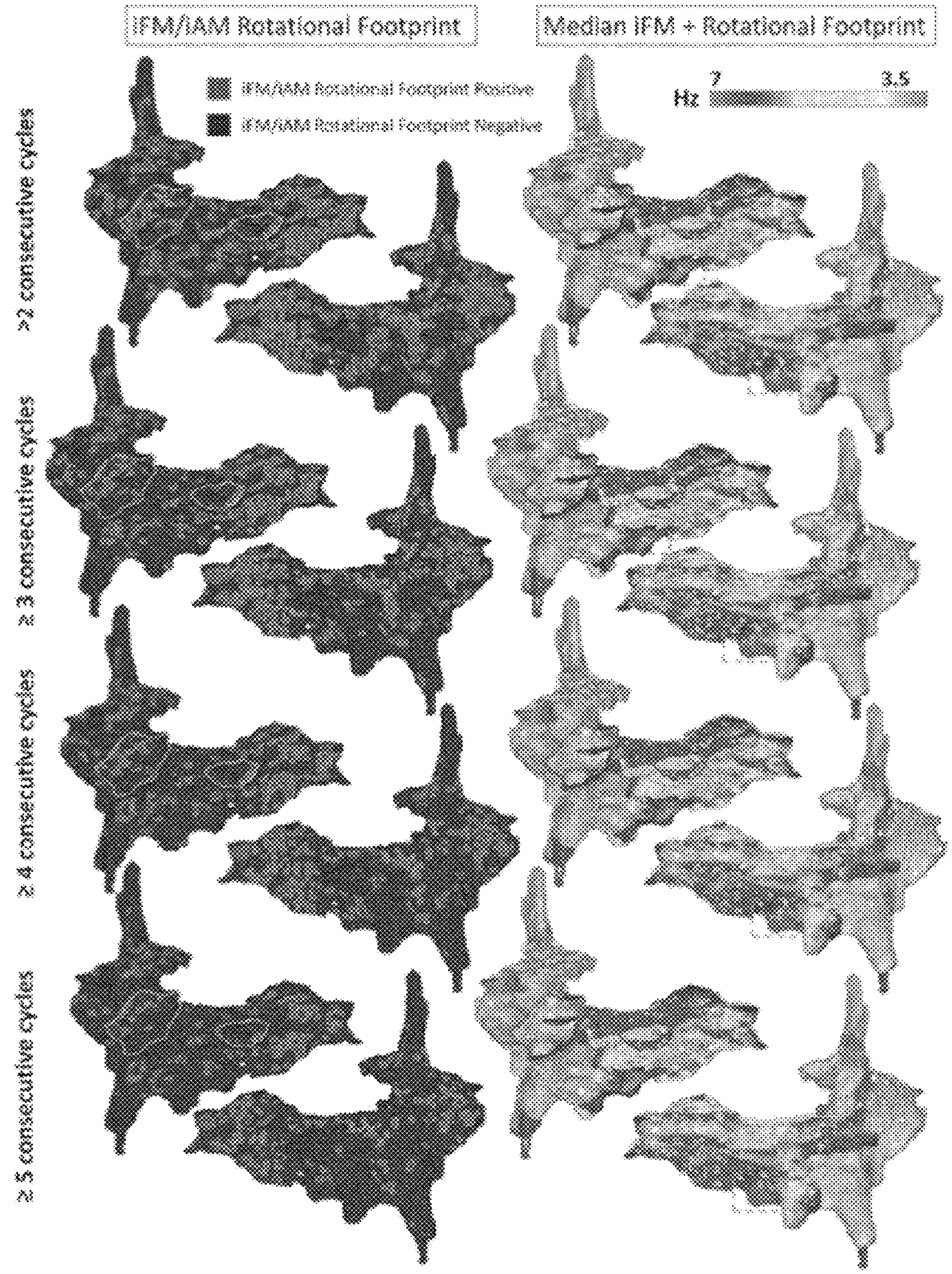

FIG. 10. This figure shows how the rotational-footprint and the combined maps (median iFM+rotational-footprint) change, depending on the criteria established for a positive rotational-footprint (2, 3, 4 or 5 consecutive cycles in which algorithm conditions are fulfilled). The higher the number of consecutive cycles required, the patchier the red areas are. However, the anatomical regions with positive rotational footprints are still the same.

Figure 11:
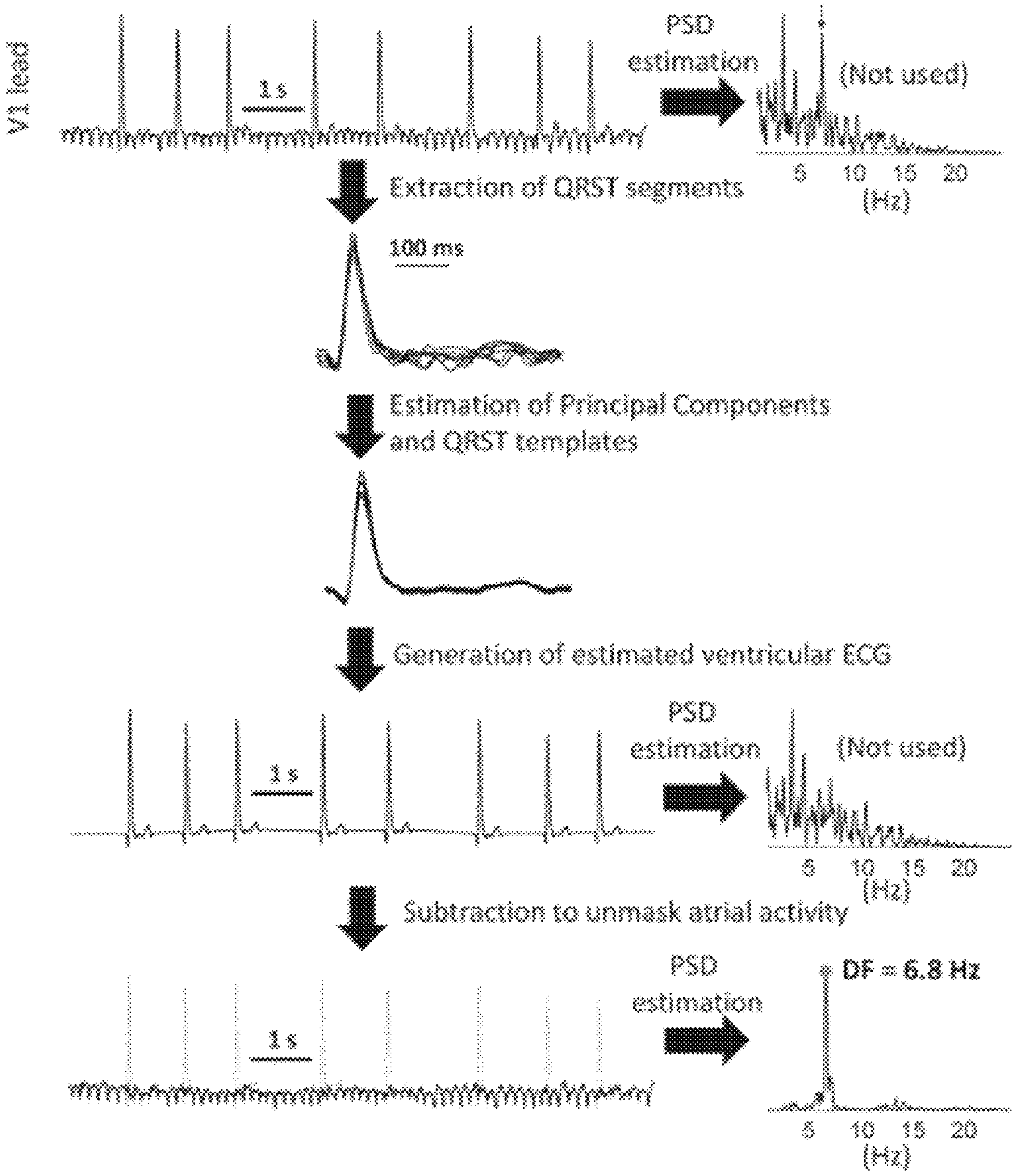

FIG. 11. QRST subtraction from a surface ECG lead. The estimated ventricular ECG is obtained using PCA, and then subtracted to obtain atrial activity. In this example, the frequency component that displays atrial activity was clearly visible in the original ECG spectrum (red arrow), but this is not always the case (see also FIG. 12).

Figure 12:
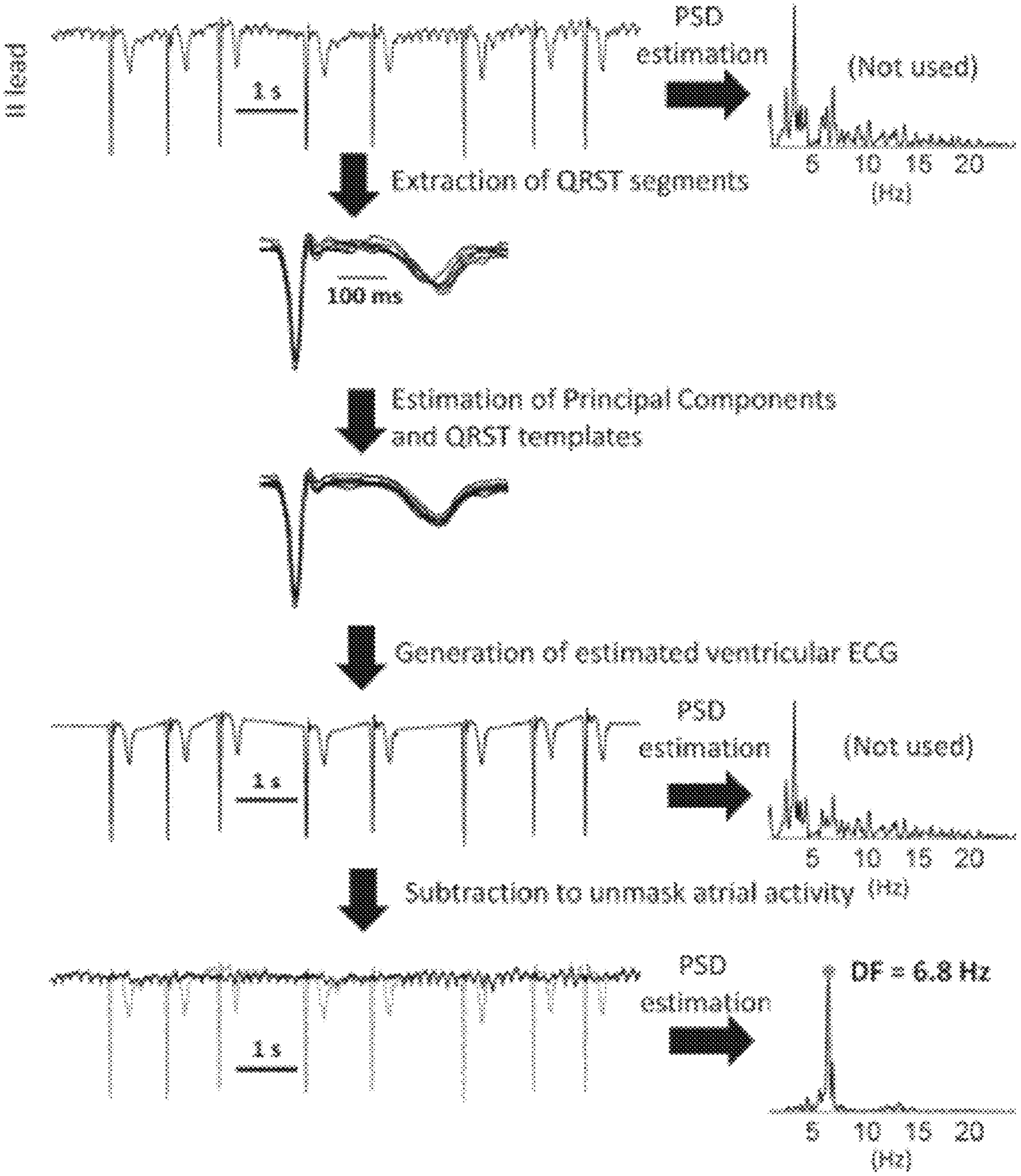

FIG. 12. QRST subtraction from a surface ECG lead. The estimated ventricular ECG is obtained using PCA, and then subtracted to obtain atrial activity. In this example, the frequency component that displays atrial activity was not clearly present in the original ECG spectrum.

FIG. 13. Comparison of the approaches to detect hierarchically relevant regions (driver regions) in persistent AF: 1) Median instantaneous frequency modulation (iFM), 2) Mean iFM, 3) Bipolar dominant frequency (DF) (upper limit for DF: 16 Hz), 4) Bipolar DF (upper limit for DF: 8 Hz) and 5) Bipolar DF (upper limit for DF: 8 Hz, only points with regularity index RI>0.2). a, b, c, d, e, f, g, h, i display the locations where the signals shown in FIG. 14 were retrieved from. See text for details.

FIG. 14. Examples of signals from different atrial regions that illustrate the relative inability of dominant frequency values obtained from bipolar signals for detecting the most hierarchically relevant regions during persistent AF. The first row in each panel shows the bipolar signal, its power spectral density, dominant frequency (DF) and regularity index (RI). The second row displays the raw unipolar signal (grey dashed trace) and the resulting unipolar signal after ventricular far-field minimization (black trace). The third row shows the absolute negative slope (ANS) signal, in which activation times (cyan circles) are detected to calculate the instantaneous frequency modulation (iFM) signal shown in the fourth row in blue. Red circles in the third row display the amplitude values of the unipolar signal used to calculate the instantaneous amplitude modulation (iAM, red trace in the fourth row). Also, the mean and median iFM values are shown to summarize the local average activation rate. a. Signal with a good correlation between Bipolar DF and median/mean iFM. a. Signal with a good correlation between Bipolar DF and median/mean iFM but RI<0.2 because of the harmonic peaks. Note that this type of signal would have been removed from the map in previous approaches. c. Signal with an acceptable correlation between Bipolar DF and median/mean iFM and RI>0.2. FIG. 14 (continued). d. Signal with a very bad correlation between Bipolar DF and median/mean iFM because the second harmonic was selected as DF. Using 8 Hz as the upper limit for DF, bipolar DF decreased from 11.8 to 5.7 Hz and RI decreased from 0.16 to 0.10. Note that even showing an improved correlation (bipolar DF=5.7 Hz, median iFM=6.0 Hz), a RI<0.2 would preclude this signal to be included in the map to guide ablation. e. Signal with a very bad correlation between Bipolar DF and median/mean iFM. Using 8 Hz as the upper limit for DF, bipolar DF decreased from 15.8 to 6.8 Hz and RI decreased from 0.13 to 0.06. f. Signal with a very bad correlation between Bipolar DF and median/mean iFM. Using 8 Hz as upper limit for DF, bipolar DF decreased from 15.8 to 7.2 Hz and RI decreased from 0.13 to 0.07. FIG. 14 (continued). g. Signal with a very bad correlation between Bipolar DF and median/mean iFM. Using 8 Hz as the upper limit for DF, bipolar DF decreased from 11.2 to 5.2 Hz and RI decreased from 0.13 to 0.08. h. Signal with a very bad correlation between Bipolar DF and median/mean iFM. Using 8 Hz as the upper limit for DF, bipolar DF decreased from 11.7 to 5.8 Hz and RI decreased from 0.15 to 0.10. i. Signal with a very bad correlation between Bipolar DF and median/mean iFM. Using 8 Hz as upper the limit for DF, bipolar DF decreased from 14.0 to 5.1 Hz and RI decreased from 0.16 to 0.07. Note that this point was one of those with the highest median iFM (7.3 Hz, maximum value) and was located within the region that was ablated to terminate persistent AF. However, bipolar DF was only 5.1 Hz (at best) in that location which would not have identified as such a relevant target using a DF approach.

Figure 15:
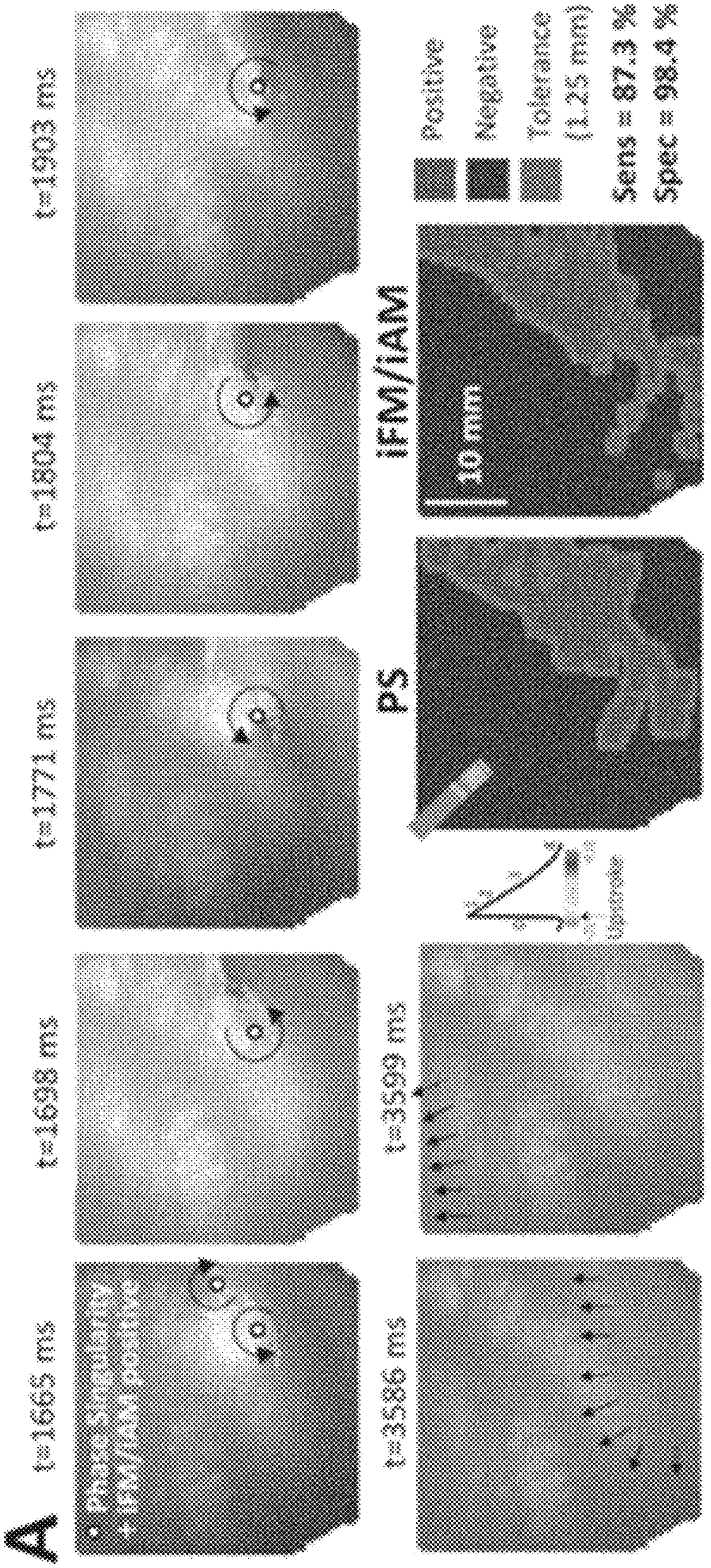
Figure 15:
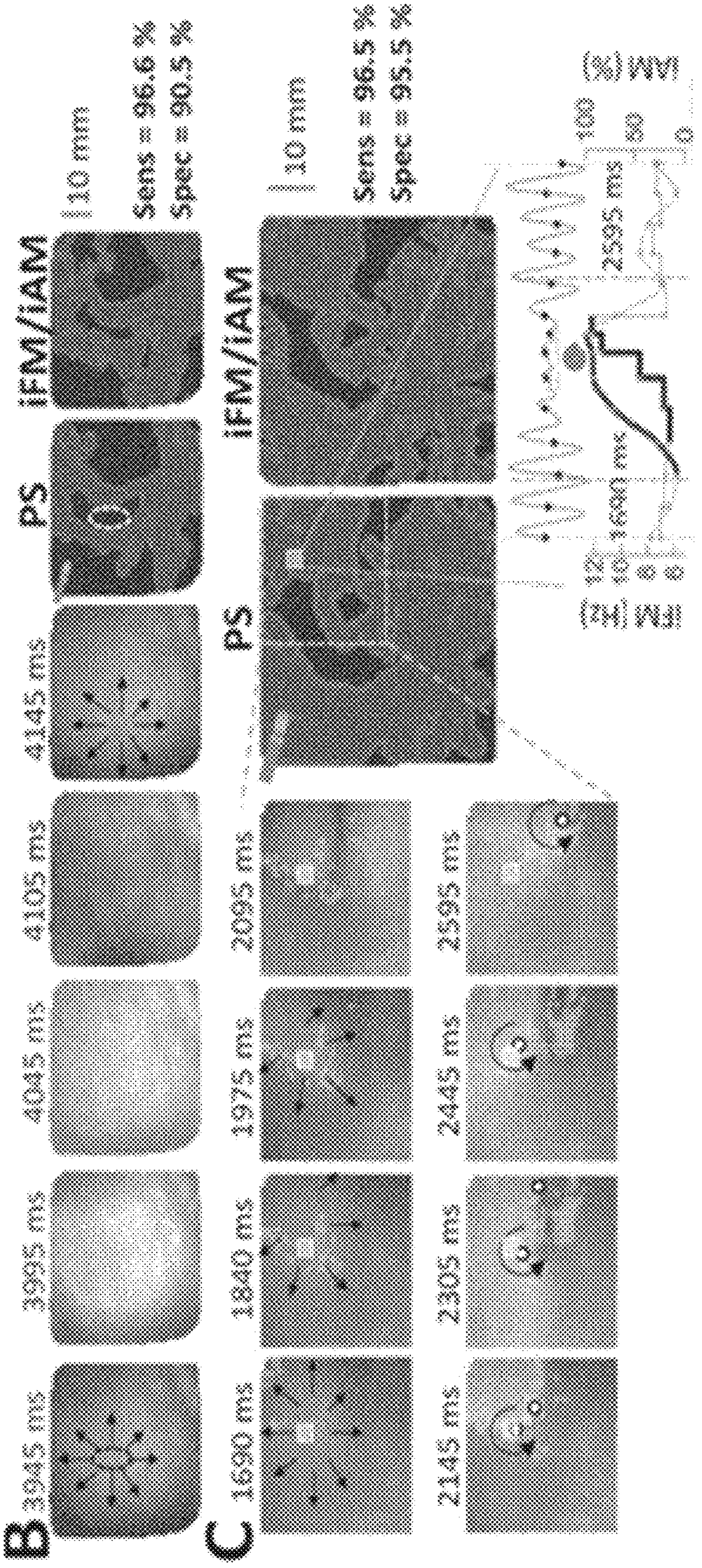
Figure 15:
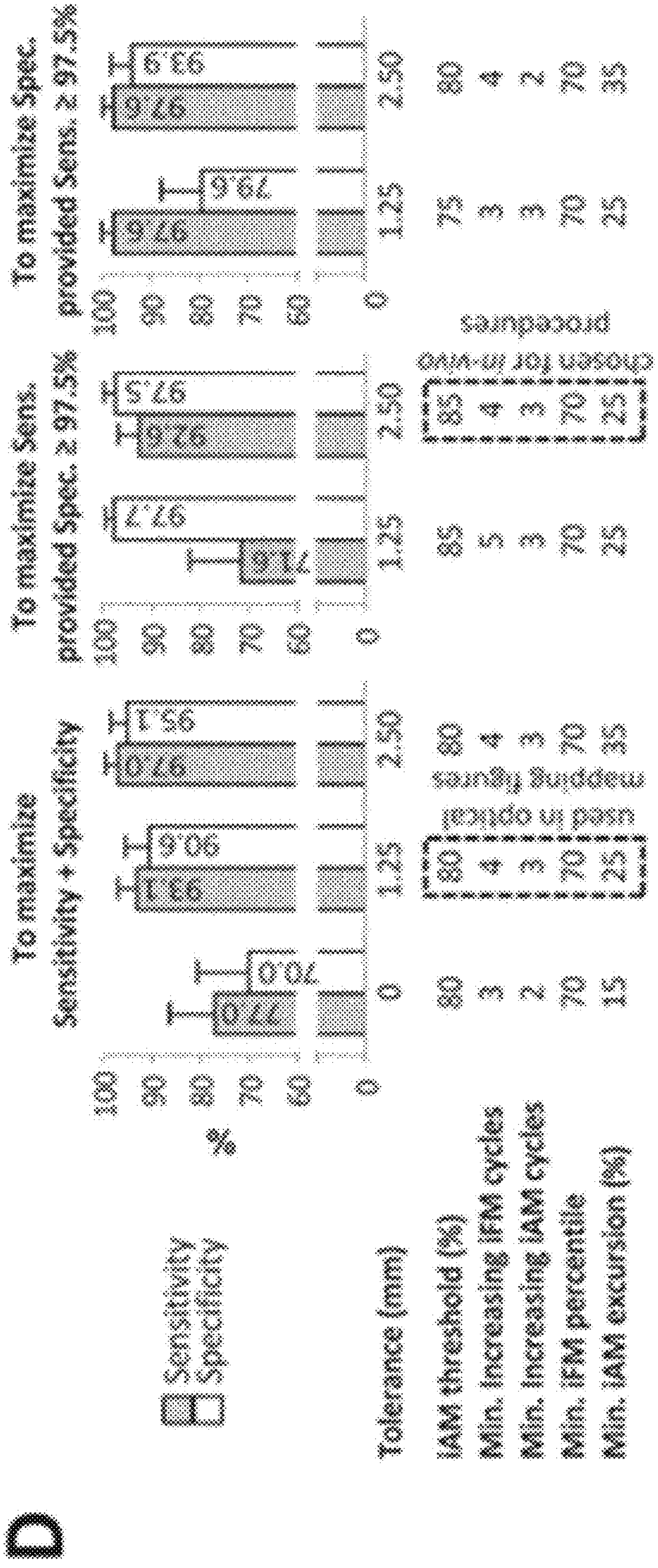

FIG. 15. Performance of the iFM/iAM algorithm to detect rotational-footprints in optical movies from PersAF sheep. A. Sample snapshots from sheep #1 with a drifting rotor (top row) that eventually leaves the field of view. Then, planar wavefronts appear on the field of view. The single-signal algorithm yielded positive results (white '+') in the pixels near the pivoting point of the drifting rotor (phase singularities, PS). Importantly, during planar wavefront intervals none of the pixels were tagged as positive. The PS map displays in red the pixels that were actually crossed by a PS (gold-standard). The map labelled as iFM/iAM displays in red the pixels that were 'rotational-footprint positive' according to the iFM/iAM algorithm. Considering a 1.25 mm tolerance (light blue areas, width equal to the radius of a conventional ablation electrode), both maps are extremely similar. B. Sample snapshots from sheep #2 displaying a time interval with centrifugal activation. C. Sample snapshots from sheep #3 displaying a time interval with breakthrough activation. The pixel marked with a grey square shows a sample signal during the same time interval. A simultaneous increase in IFM and iAM is present. Therefore, the initial breakthroughs seem to be the result of a scroll wave with a changing filament approaching the mapped epicardial surface. Indeed, this breakthrough activation immediately turned into a drifting figure-of-eight reentry. D. Optimal combinations of all 5 parameters used in the iFM/iAM algorithm for detecting rotational-footprints.

Figure 16:
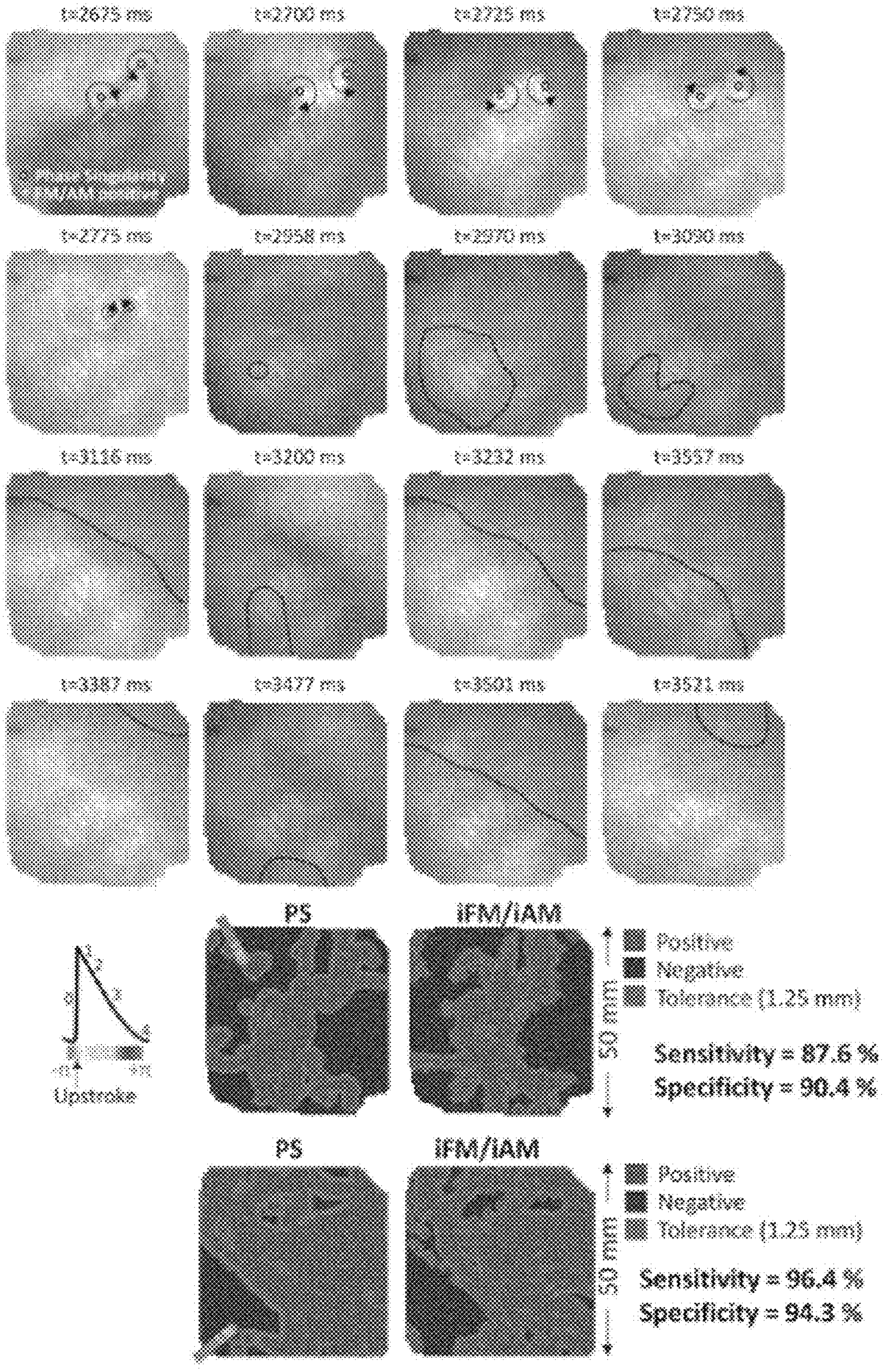

FIG. 16. A. Sample optical snapshots from sheep #4 displaying a figure-of-eight reentry, breakthroughs and planar wavefronts. Note that the single-signal iFM/iAM algorithm consistently displayed positive rotational-footprints in pixels close to the phase singularities (PS) of the figure-of-eight reentry. Conversely, no positive detections were displayed by the algorithm during the time intervals with centrifugal/planar wavefront activations. B. SP and iFM/iAM maps of a sample optical mapping movie from sheep #5.

Figure 17:
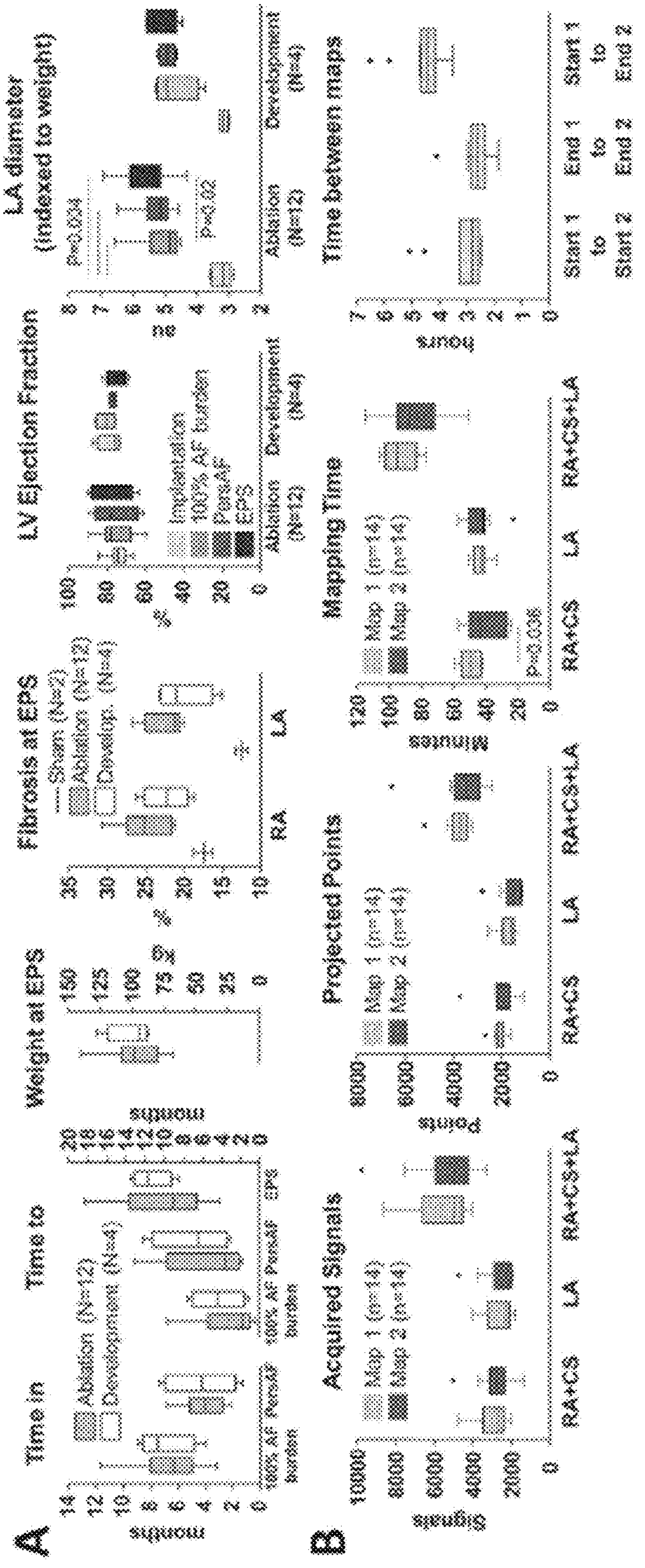
Figure 17:
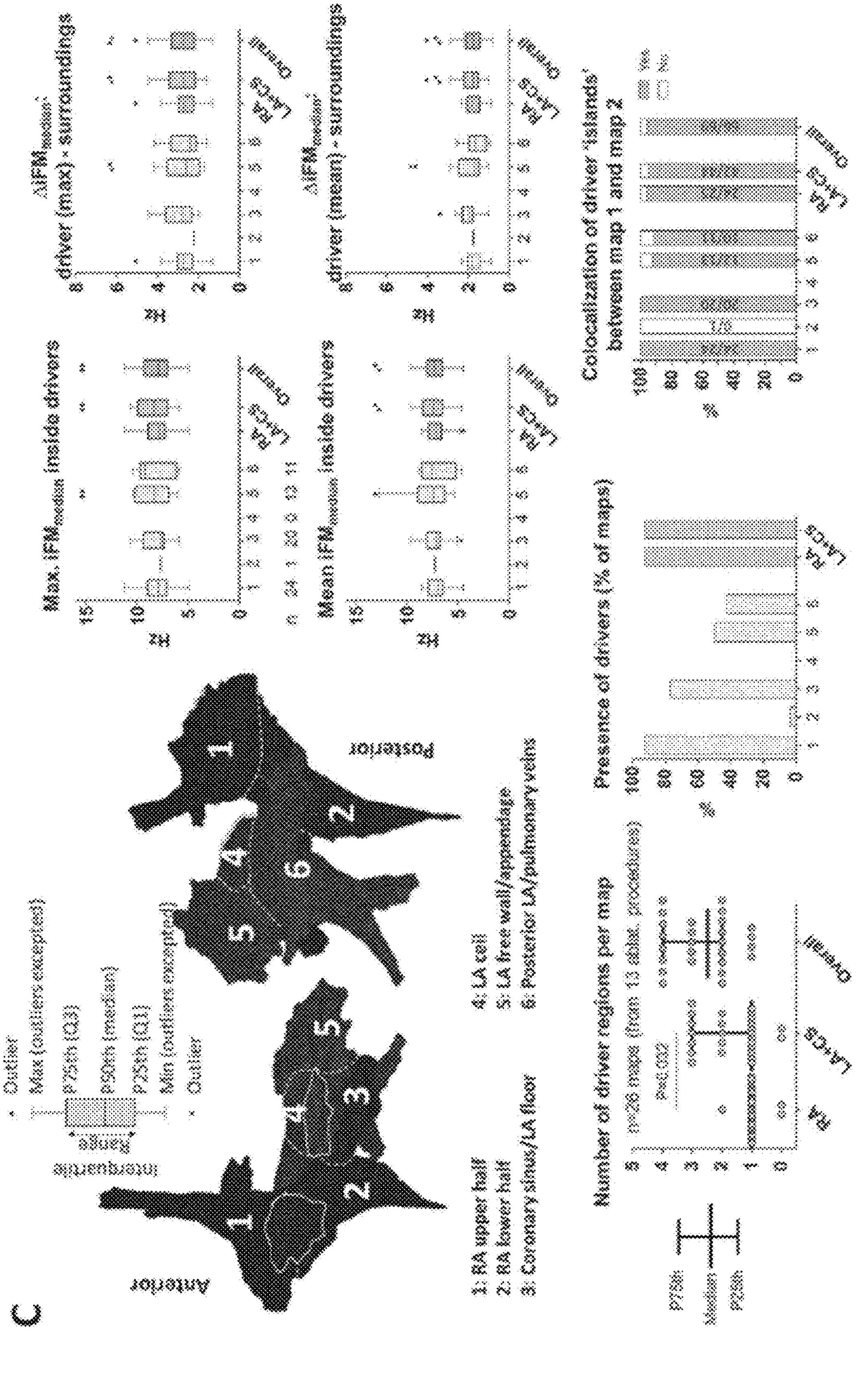
Figure 17:
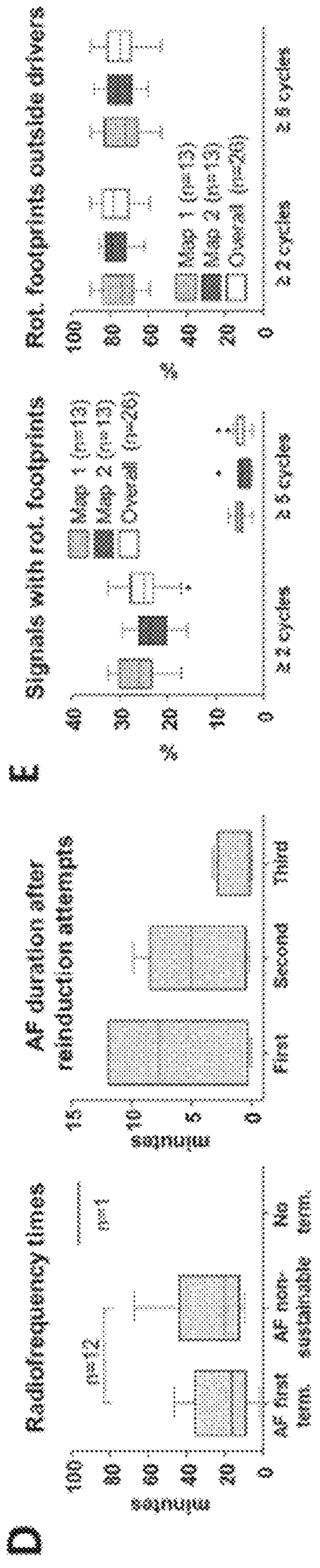

FIG. 17. In-vivo quantitative results. A. Descriptive data of the porcine model of PersAF. B. Descriptive data about electroanatomical mapping. C. IFM values, gradients, regional distribution and spatiotemporal stability of 'high-hierarchy' regions. D. Ablation data. E. Rotational-footprint quantification and spatial correlation with 'high-hierarchy' atrial fibrillation drivers. Data are usually displayed with Tuckey's box plots. P values are only shown for statistically significant differences.

Figure 18:
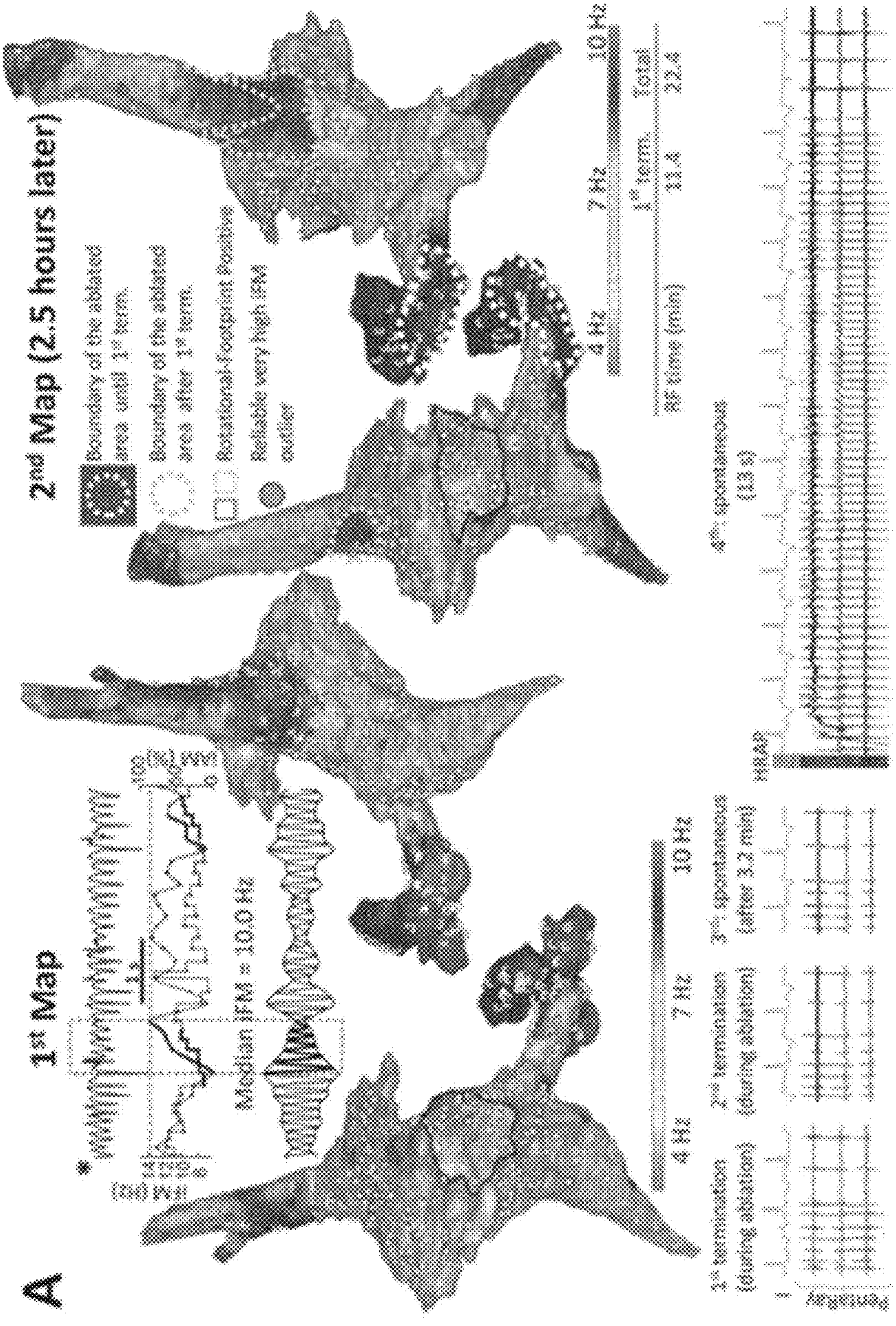
Figure 18:
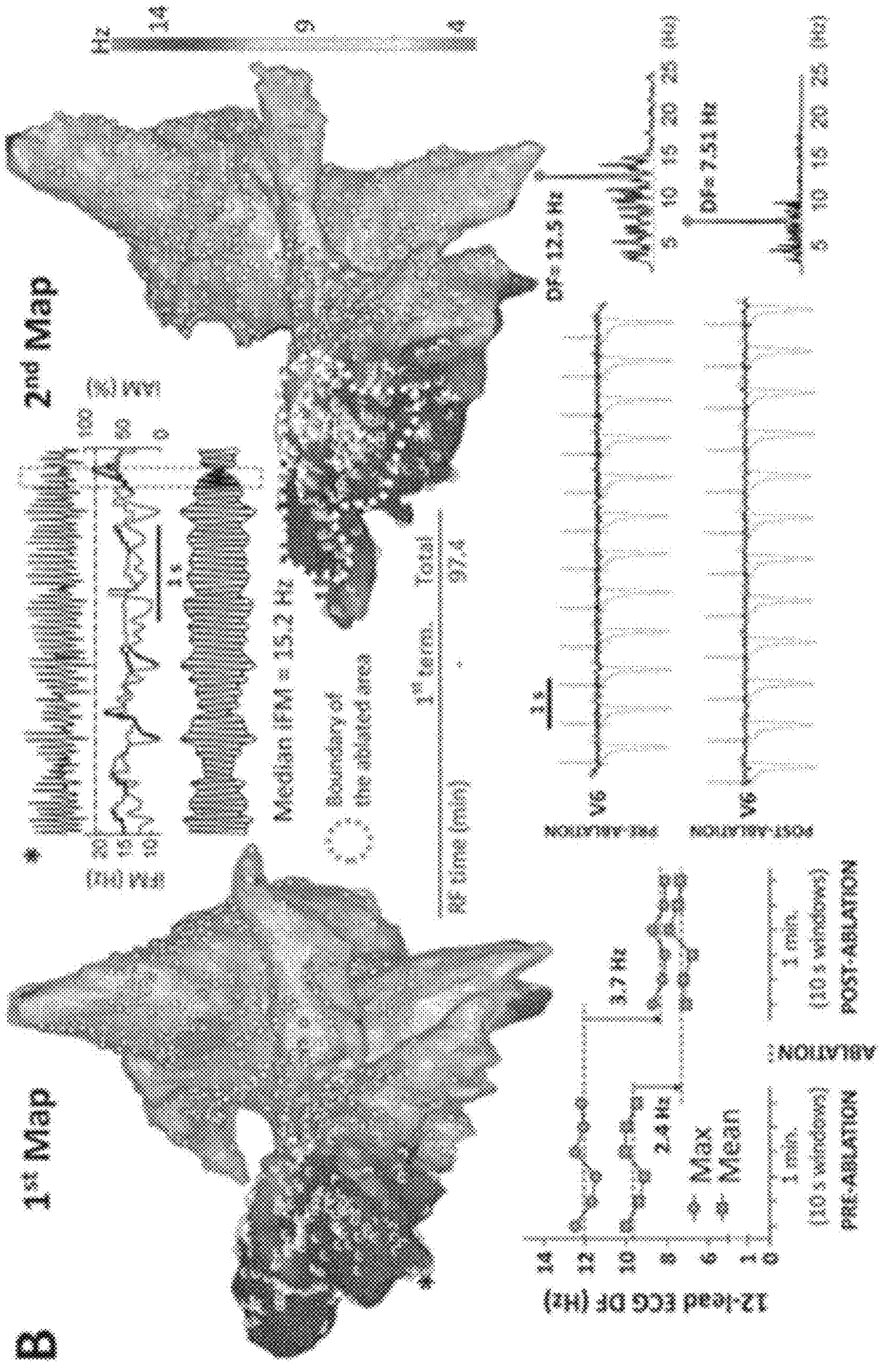

FIG. 18. 'High-hierarchy' regions are highly stable in the medium-term (hours). A. Sample case with PersAF termination during catheter-based radiofrequency delivery. Note the extremely high similarity between the first and the second maps, acquired ~2.5 hours apart. PersAF successfully terminated after ablating the coronary sinus region on the delineated fuchsia area for 11.4 minutes. Then, AF was reinduced using very high rate atrial pacing and the episode was sustained from >10 min. Therefore, we continued ablating the other driver region (delineated with the orange dashed line) for 11 more minutes, which yielded successful AF termination. Then, AF was no longer sustainable from more than a few minutes. B. Sample case with extensive atrial remodelling due to severe tricuspid regurgitation. Extremely high atrial iFM median values over large areas of the left atrium were documented after mapping. The latter precluded us from achieving successful AF termination during radiofrequency delivery. This panel shows the only pig, in which ablation did not terminate PersAF. $iFM_{median}$ values in such pig were much higher than in the rest of animals (LA: ~15 Hz, RA: ~9 Hz). Again, note the huge similarity between the first and second maps acquired >2.5 hours apart. Importantly, despite delivering radiofrequency for 97 minutes, PersAF did not terminate. However, ablation resulted in an important reduction in the overall atrial activation rate measured by DF from the 12-lead surface ECG (bottom panel). Asterisks mark the locations where the displayed signals were retrieved from.

Figure 19:
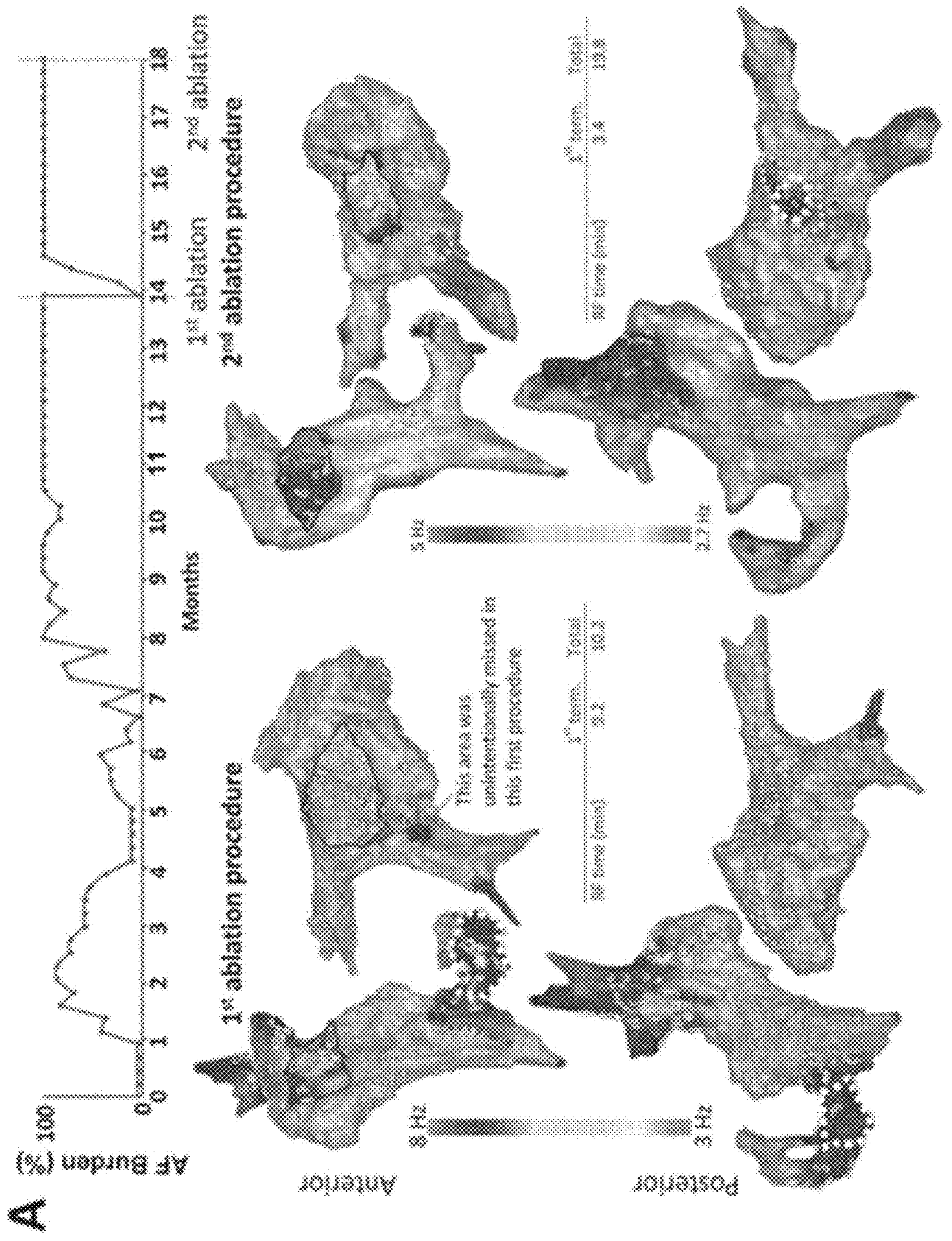
Figure 19:
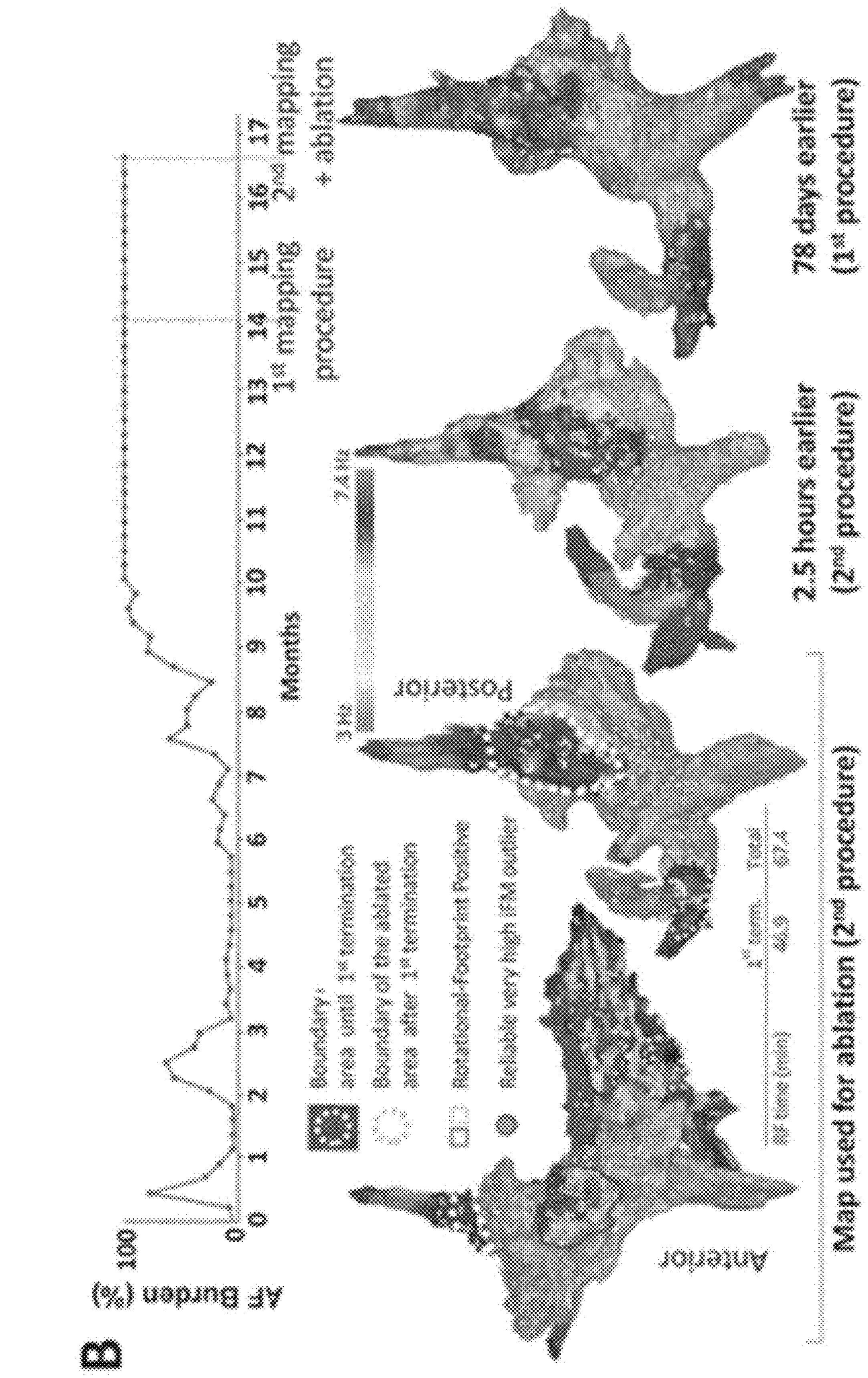
Figure 20:
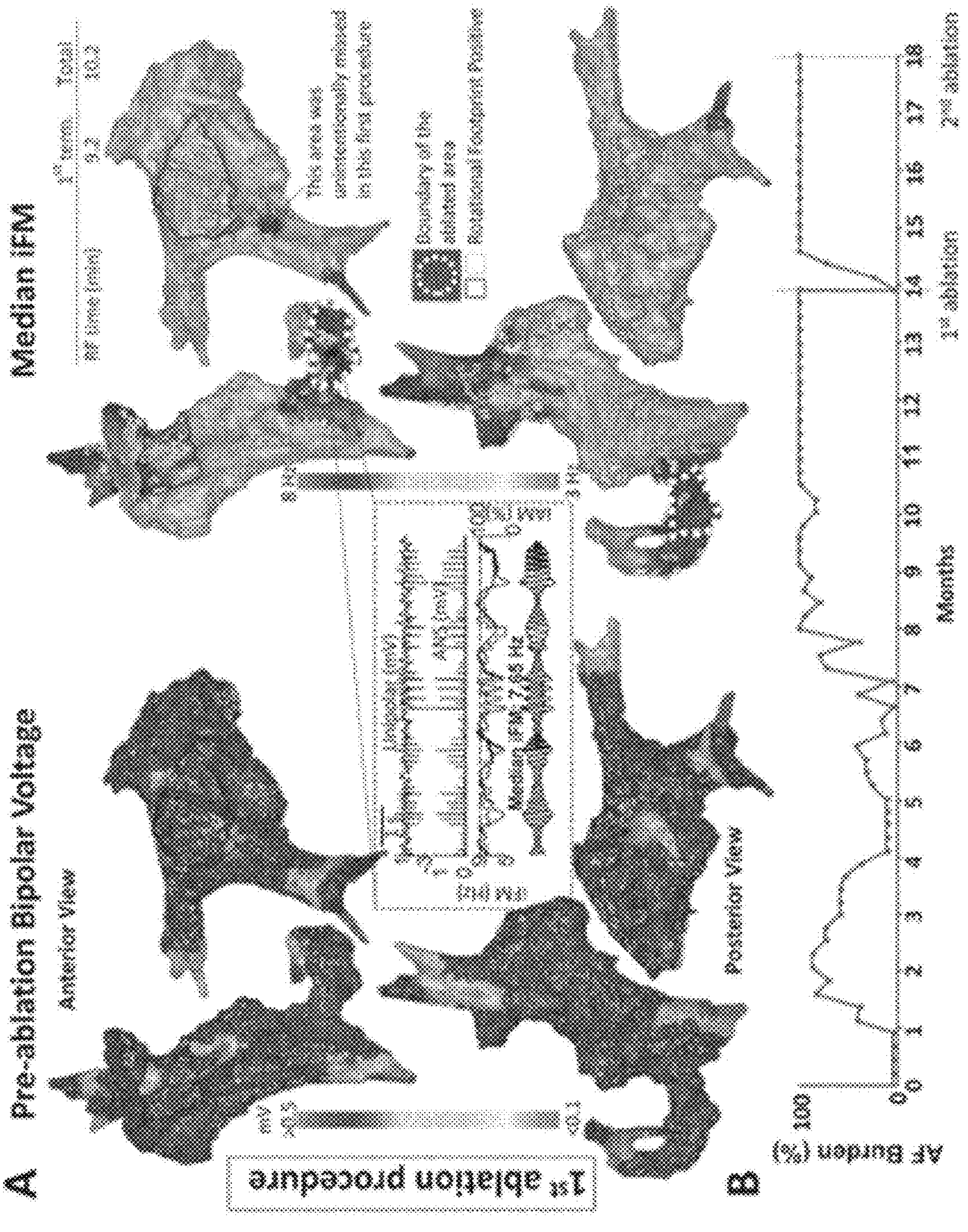
Figure 20:
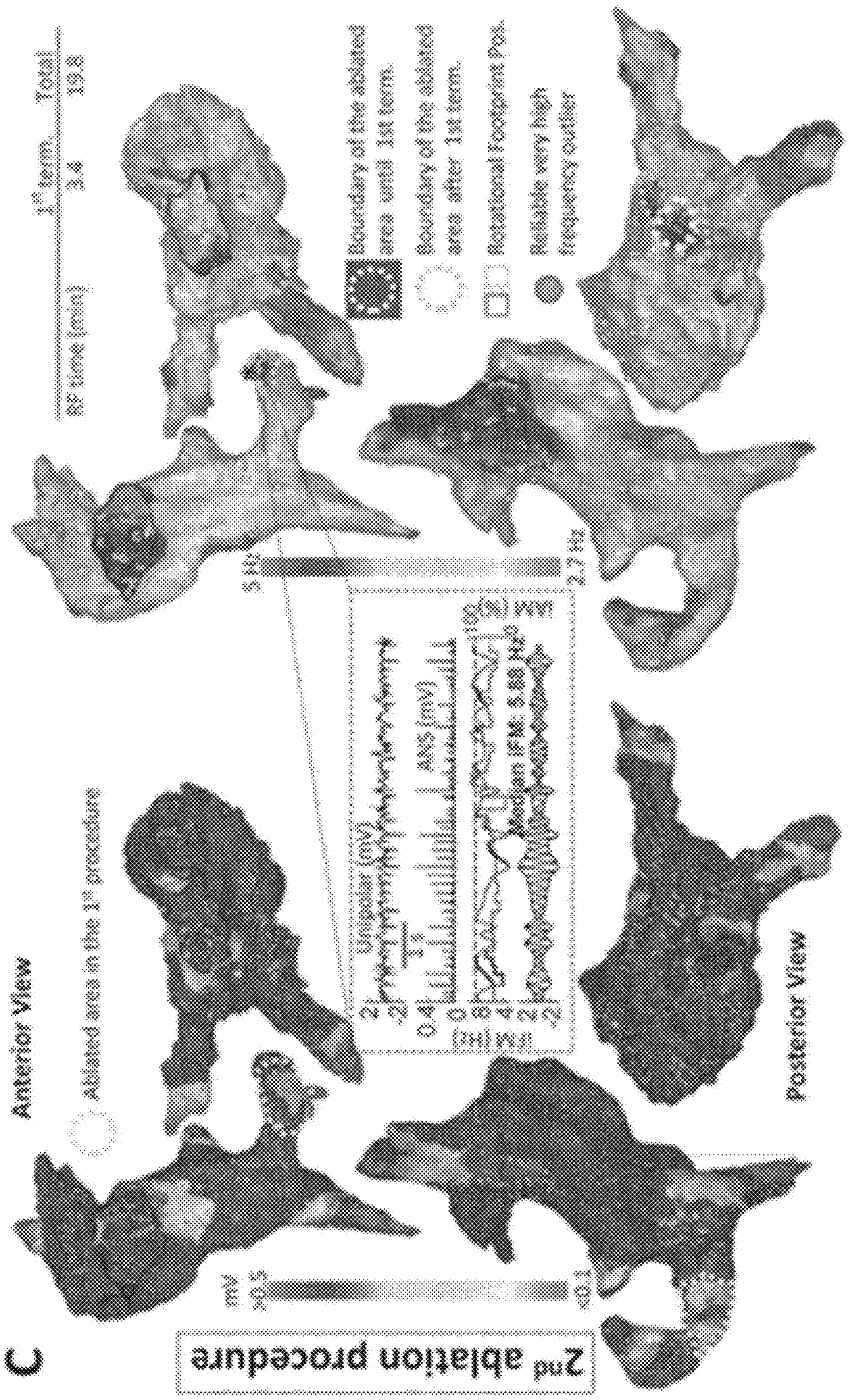
Figure 21:
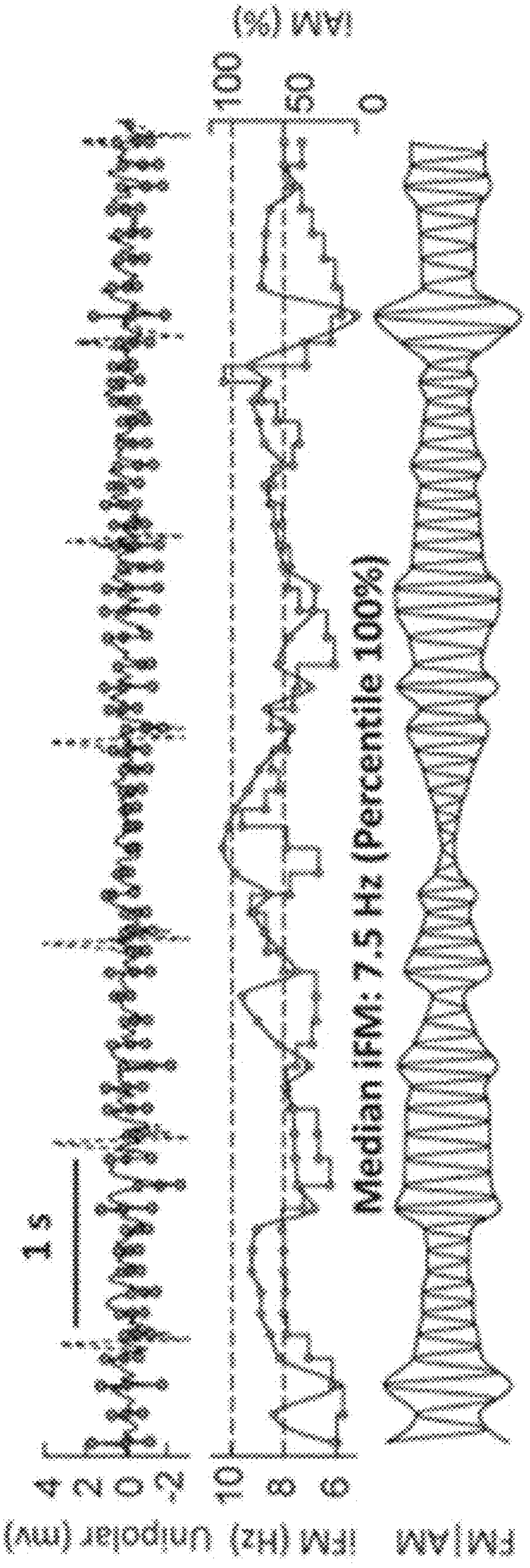

FIG. 19. 'High-hierarchy' regions seem stable in the long-term. A. One pig was kept alive for 4 more months after a $1^{st}$ ablation procedure, and before performing a $2^{nd}$ mapping+ablation procedure. PersAF acutely terminated and was rendered non-sustainable after ablating the coronary sinus region during the $1^{st}$ procedure. Accordingly, AF burden (percent of time in AF) was temporally reduced to 0%. It took it >3 weeks of high rate atrial pacing to reach 100% AF burden again. Signals from locations marked with an asterisk and pre-ablation bipolar voltage maps are shown in FIG. 20. $iFM_{median}$ values were much lower in the $2^{nd}$ procedure (note the different color scales). 'High-hierarchy' areas in the $1^{st}$ procedure that were not ablated remained as key regions in the $2^{nd}$ procedure. Also, a new area with consistent high $iFM_{median}$ outliers was found in the posterior LA and its ablation terminated PersAF after 3.4 minutes of radiofrequency delivery. Then, AF was reinduced and lasted for >10 minutes, so ablation protocol was resumed. After completing the region at posterior LA, ablating the area unintentionally missed in the previous procedure and the reliable iFM outliers at the boundary of the previously ablated tissue at the coronary sinus, AF terminated again (total radiofrequency time: 19.8 min). Then, all the reinduced AF episodes were potentially maintained by the non-ablated 'high-hierarchy' region at the RA and self-terminated after 8-9 minutes (<10 min), so ablation protocol was not continued. B. Sample pig with 2 mapping procedures 78 days apart. Target areas were stable from the first to the second mapping procedure. Left panel: during the second procedure PersAF successfully terminated after ~47 minutes of radiofrequency delivery within the area delineated with a fuchsia dashed line. Then, 20 more minutes of radiofrequency delivery were needed to complete that area and to ablate the other high-hierarchy region at the coronary sinus (orange dashed line). A signal from the white asterisk location is shown in FIG. 21. Then, atrial fibrillation episodes were no longer sustained after high rate atrial pacing (longest reinduced episode: 17 seconds). Middle panel: $iFM_{median}$ map acquired ~2.5 hours earlier. Right panel: $iFM_{median}$ map acquired 78 days earlier (without ablation) with the same 'high-hierarchy' regions driving PersAF.

FIG. 20. This figure is an extended version of panel A in FIG. 19. Pre-ablation voltage maps and signals from the main driver regions are additionally shown. This pig underwent 2 ablation procedures ~4 months apart to demonstrate that acute termination of persistent AF during the first ablation procedure was the result of an important modification of the underlying substrate that was maintaining persistent AF. A. First ablation procedure. Left panel: pre-ablation bipolar voltage during AF. Both atria mostly consisted of healthy tissue (>0.5 mV). Only venous or peri-annular regions showed bipolar voltages ≤0.5 mV. Right panel: persistent AF terminated after ablating a high hierarchy region in the coronary sinus for ~10 min. Note that a high hierarchy area at the ostium of the inferior pulmonary vein and close to the coronary sinus was unintentionally missed. B. After the first ablation procedure, the pig was kept alive for 4 more months before attempting a second mapping+ablation procedure. After the acute termination of persistent AF during the first ablation procedure AF burden was reduced to 0%. It took over 3 weeks of high rate atrial pacing to reach 100% AF burden again. This fact confirms that the ablated high-hierarchy regions were highly relevant for persistent AF maintenance. C. Second ablation procedure. Left panel: bipolar voltage map during AF. In addition to venous or peri-annular regions, the coronary sinus region that had been ablated during the first procedure also presented low bipolar voltage values. The new persistent AF episode presented high hierarchy reliable outliers at the previously unintentionally missed area, at the boundary of the area ablated in the coronary sinus, and at the posterior left atrium (PLA). Note that this AF was considerably slower than the one in the previous procedure. Persistent AF terminated after 3.4 min of radiofrequency delivery at the posterior left atrium (delineated with the fuchsia dashed line). Then, AF was reinduced and lasted >10 minutes. Therefore ablation protocol was resumed to complete ablation on posterior left atrium, and to target the area unintentionally missed in the previous procedure and the outliers at the boundary of the previously ablated tissue at the coronary sinus. Such approach terminated AF again (total RF time: 19.8 min) and AF was no longer sustainable for more than 10 minutes.

FIG. 21. Sample signal with the maximum $iFM_{median}$ from the map showed in FIG. 19B. This signal was retrieved from the coronary sinus (white '*' in FIG. 19B). Note the presence of 6 intervals of increasing instantaneous frequency modulation for ≥4 cycles (blue thick line). Even though the accompanying iAM did not reach the required 85% threshold to consider that a rotor crossed through the location, these sustained intervals of increasing iFM likely indicate the presence of rotors/scroll waves nearby.

Figure 22:
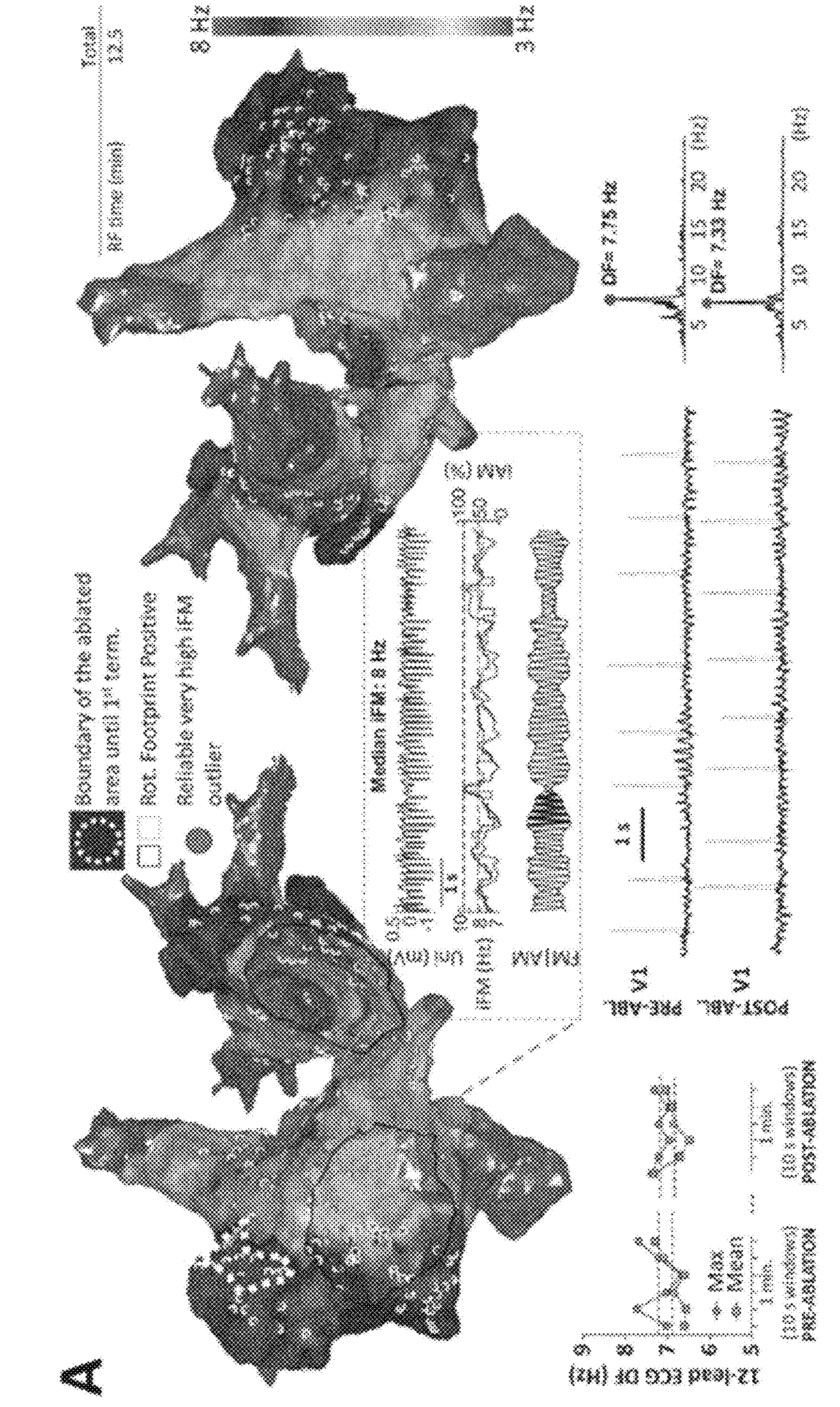
Figure 22:
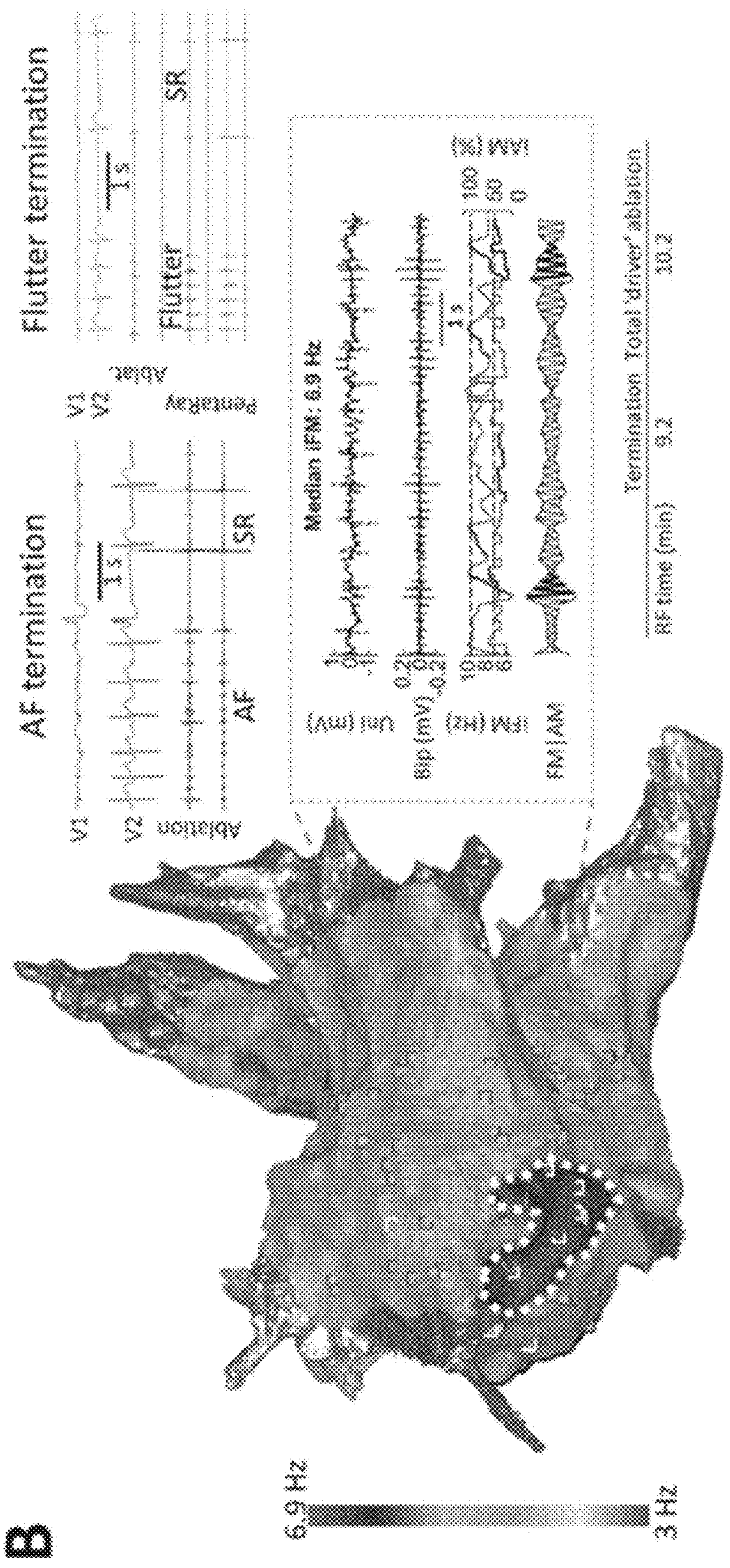

FIG. 22. Translation ability of the iFM/iAM approach to terminate recurrent PersAF episodes in patients who have undergone ≥1 previous pulmonary vein isolation (PVI) procedure. After PVI was confirmed, a single biatrial map was acquired. A. Sample patient case undergoing a third ablation procedure after two previous unsuccessful ablation procedures. The iFM/iAM-based approach identified large and fast 'high-hierarchy' regions covering a considerable portion of the total atrial surface, similar to the pig case showed in FIG. 18B. Such large areas precluded a limited ablation strategy from acutely terminating PersAF. Thus, limiting the ablation to the region delineated with the fuchsia dashed line for 12.5 min did not modify the atrial activation rates on the 12-lead ECG. The patient was then cardioverted but, as expected, AF recurred after a few days. Nevertheless, this kind of maps may anticipate failure of a limited ablation strategy, although other therapeutic options as surgical ablation may still be an option for symptomatic patients. B. Sample patient case with a high-hierarchy region identified with the iFM/iAM approach. Limited radiofrequency delivery for ~10 min successfully terminate PersAF. Upon reinduction, common atrial flutter was the only inducible arrhythmia, which was eventually terminated by creating a linear lesion at the cavotricuspid isthmus. After nine months of follow-up, this patient remains in sinus rhythm without taking antiarrhythmic drugs.

DESCRIPTION OF THE INVENTION

Abbreviations used: AF: atrial fibrillation, ANS: absolute negative slope, APS: absolute positive slope, ECG: electrocardiogram, FM: frequency modulated signal, FM|AM: frequency and amplitude modulated signal, iAM: instantaneous amplitude modulation, iFM: instantaneous frequency modulation, MESPAS: multielectrode (64-256) simultaneous panoramic acquisition systems, PersAF: persistent atrial fibrillation, PS: phase singularity, PSD: power spectral density.

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

The main findings of this invention are: 1) the combined analysis of the iFM and iAM present in single-signals during cardiac fibrillation can detect 'high-hierarchy' drivers' and/or the footprint of rotational activations (rotors) with high sensitivity and specificity without the need of costly MESPAS (see Figure IA-B); 2) 'islands'/regions of tissue with reproducibly higher average iFM values than their surroundings are those actually sustaining cardiac fibrillation ('high-hierarchy' drivers), are stable at least for hours, and their ablation acutely terminates cardiac fibrillation and renders it non-sustainable (see FIGS. 17D, 18 and 19); 3) rotational activations (rotors) are sensitive but not specific to these regions (see FIG. 17E); and 4) it is feasible to translate this approach to treat cardiac fibrillation, preferably atrial fibrillation, more preferably persistent atrial fibrillation patients (see FIG. 22).

Figure 1:
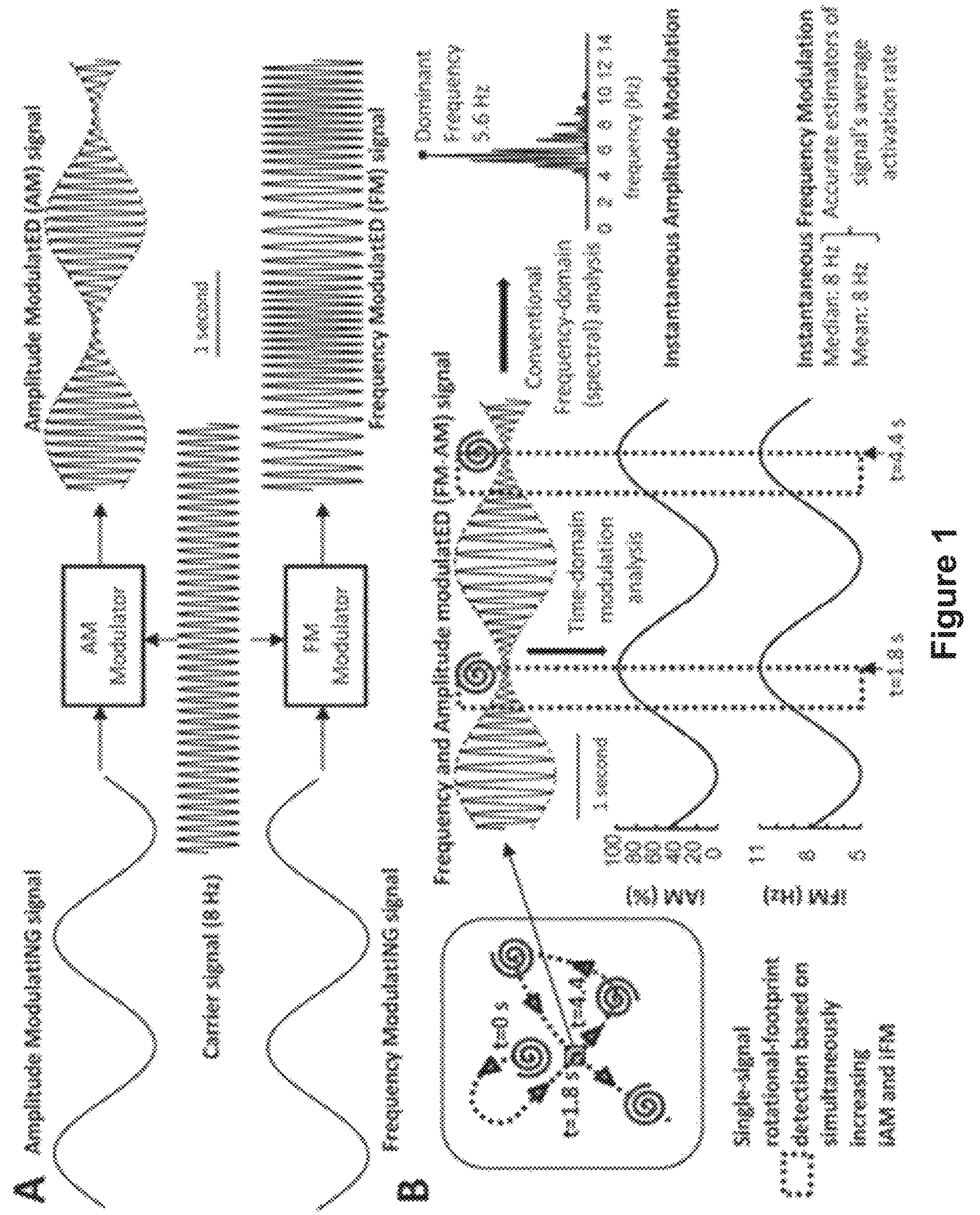
FIG. 1. A. Concept of AM/FM used in radio broadcasting. Note that in FM the increases in the blue modulatING signal make the sinusoid oscillate proportionally faster and vice versa. B. AM and FM are present during cardiac fibrillation due to scroll-wave/rotor drifting. A schematic representation of a piece of cardiac tissue is displayed in red. When a drifting scroll-wave filament/rotor core approaches the blue square spot, the amplitude of the action potentials decreases resulting in an increased iAM (in red). Simultaneously, as the wave-emitting source (scroll-wave filament/rotor core) is approaching, the perceived iFM (in blue) at the spot increases (Doppler Effect). In this schematic representation, this situation occurs at 1.8 and 4.4 seconds. Therefore, a simultaneous iAM/iFM increase is indicative of drifting scroll-waves/rotors in the surroundings. At the same time, the areas with the highest values of average (mean/median) iFM would be those hierarchically driving fibrillation (drivers). The right panel shows the estimation of such average iFM by its median/mean values (8 Hz both) and with the conventional Dominant Frequency (DF) spectral approach (5.6 Hz). Note that the time intervals with the highest iFM usually display the lowest amplitudes and viceversa. The latter affects the height of their corresponding power spectral peaks. This and other issues limit hierarchical approaches based on DF. C. Schematic representation of the translational approach performed to develop this invention.
Figure 1:
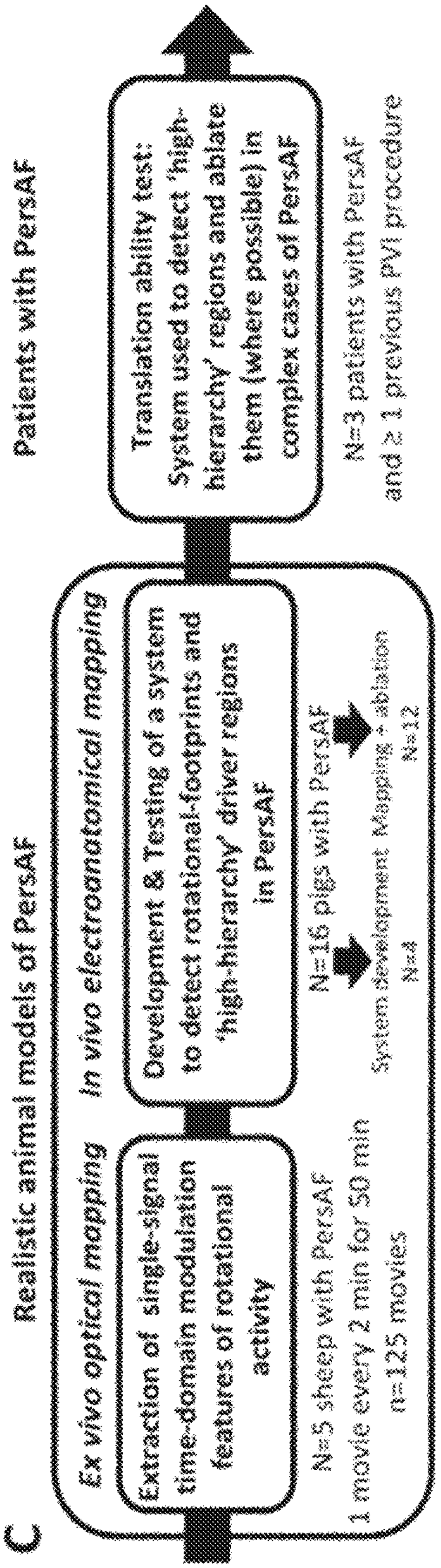

It is important to note that our findings have been mainly obtained from realistic animal models (see FIG. 1C) with long times of evolution and comparable to humans in body weight (median: 96 kg, see FIG. 17A). They mostly represent a pure PersAF (persistent atrial fibrillation) substrate with no other comorbidities that may be present in patients. Despite this might be perceived by some as a weakness, we consider such a model a strength, because it has enabled us to test our invention and hypothesis without any confounding factors. Moreover, the results from clinical studies usually include patients that, although classified as PersAF, can be in sinus rhythm at the beginning of the ablation procedure. Therefore, AF needs to be initiated by pacing maneuvers in these patients and radiofrequency ablation may lead to serendipitous AF termination. Conversely, thanks to the comprehensive monitoring to which our long-term animal model has been submitted, we can guarantee that all animals had been in PersAF for several months at the beginning of the procedure (see FIG. 17A). This makes serendipitous termination of PersAF much less likely. Importantly, fibrillatory frequencies in the animal model were very similar to those documented in patients, with the exception of the pig in which ablation did not terminate PersAF (see FIG. 18B). An intrinsic limitation of complex animal models are that are expensive and long times are needed to generate the suitable specimens with long-standing persistent AF (up to 18.3 months, see FIG. 17A). Therefore, sample sizes are small compared to most clinical studies. However, ethical considerations and temporal limitations in clinical or surgical procedures have usually precluded human studies to conclusively test the medium-term (hours) spatiotemporal stability of drivers. Therefore, testing new ablation approaches in realistic animal models of PersAF before translating them to patients should be encouraged, especially when conflicting clinical outcomes are being reported.

Figure 2:
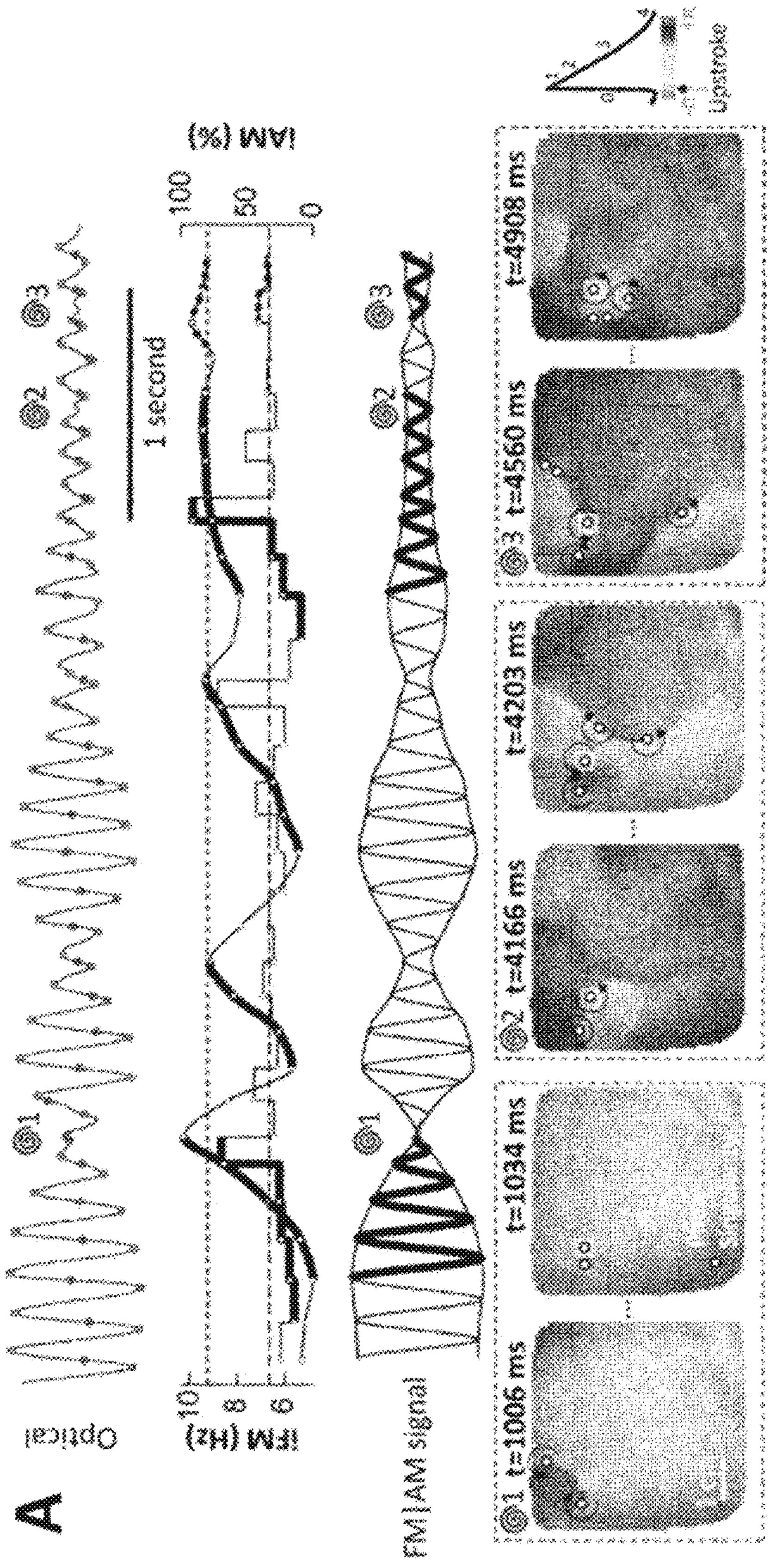
FIG. 2. Examples of iAM/iFM from an optical movie of a sheep heart with PersAF. A. Top row: optical signal from a pixel (grey square, larger than actual pixel size for viewing purposes) crossed by a phase singularity (PS) from figure-of-eight reentries at 3 different time intervals (bottom row). The times at which any PS (white circles in the bottom row) passes by the pixel are marked with a spiral. Activation times are marked with blue points. Red points show the start and the end of phase zero. The activation times are used to generate the iFM signal (second row, in blue). Phase 0 amplitude excursions are used to generate the iAM signal (second row, in red). The time intervals with sustained simultaneously increasing iFM (second row, thick blue tracings) and iAM (thick red tracings) reaching a pre-specified iAM threshold are detected. This pixel was marked as 'rotational-footprint positive'. The third row displays a 'synthetic' FM IAM signal in which the 'rotational-footprint positive' intervals detected by the algorithm are highlighted with a thicker blue line. B. Signal from a pixel close to areas swept by drifting rotors but not actually crossed by the PS associated with their cores. Note that there are still intervals with simultaneously increasing iFM and iAM. However, iAM does not reach the pre-specified threshold meaning that the rotor core has not been close enough to the pixel. Therefore, the algorithm does mark the pixel as 'rotational-footprint negative'. C. Signal from a pixel far from areas actually swept by drifting rotors. Note that, although still present, iAM is not as noticeable as in pixels close to or actually crossed by drifting rotors.
Figure 2:
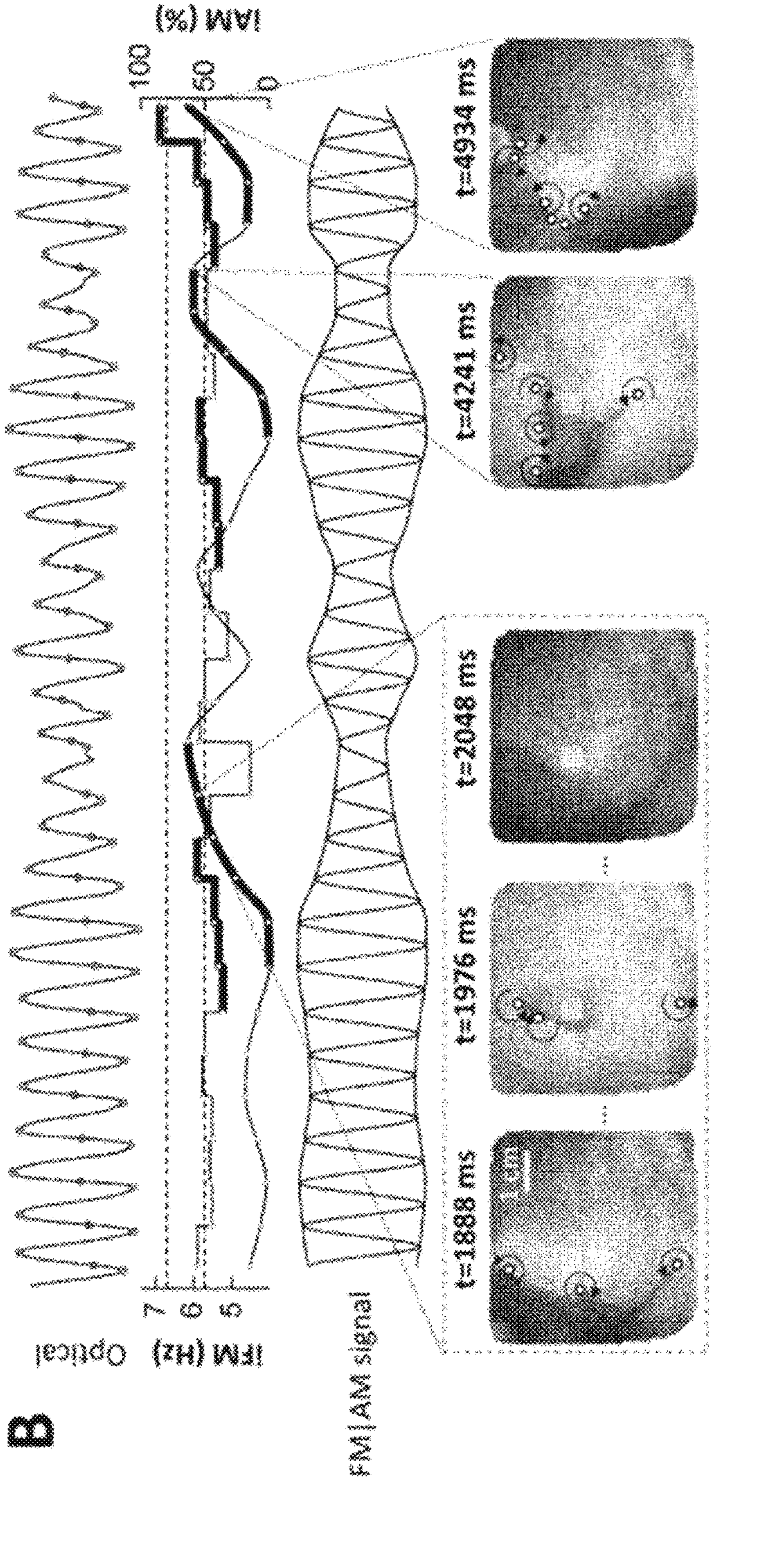
Figure 2:
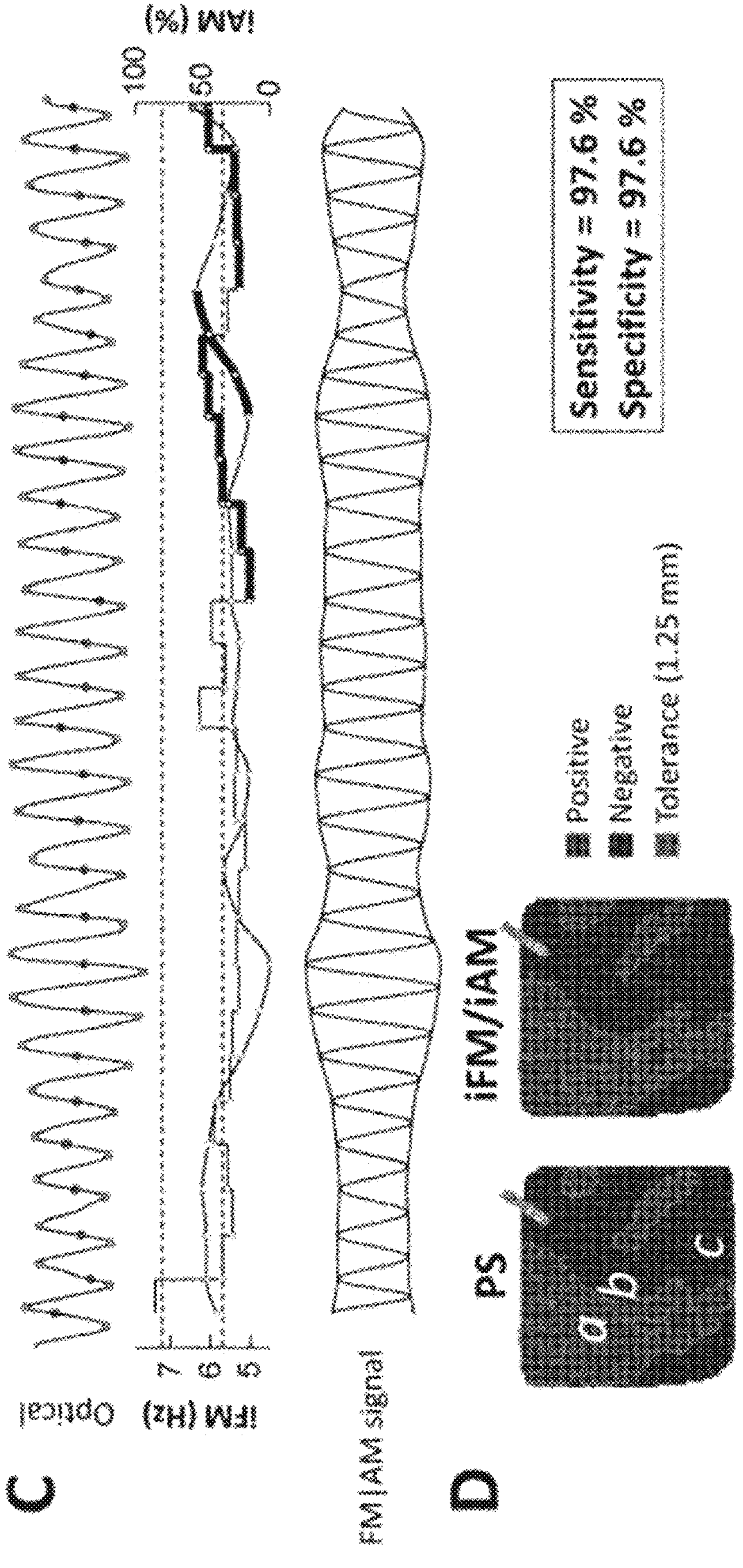

On the other hand, phase mapping of electrical data to detect potential drivers and/or rotors during cardiac fibrillation is known. However, such knowledge is usually linked to the use of multiple electrodes and is completely dependent on their location and separation. Moreover, depending on the signal processing performed, phase mapping of electrical signals can be little specific for rotor detection. In contrast and as it is shown in the examples of the present specification, our iFM-iAM algorithm allows in-vivo single-signal detection of the locations with a rotational-footprint without the need of performing phase mapping of multiple electrograms simultaneously acquired by costly MESPAS or fully deployed multispline catheters. Our invention achieves extremely high values of sensitivity and specificity with <2.5 mm accuracy, which is more than enough considering that the diameter of an ablation lesion is considerably larger. One could only expect reliable enough phase movies using multispline catheters when are well deployed and have good contact with the tissue. This scenario is not achievable in important areas of the atria (coronary sinus, pulmonary veins, septum, etc.). Indeed, previous attempts to search rotational activations by sequential positioning of a fully-deployed PentaRay catheter reported a mapping coverage of ~65% of the endocardial atrial surface, and even there some issues can arise due to interpolation of sparse data. Therefore, phase mapping of electrical data cannot be considered a 'gold-standard', and that is the reason why we only used electrical phase movies to qualitatively assess the correlation between the rotational cores in such movies and the 'rotational-footprint positive' locations detected by the iFM/iAM algorithm within areas where the PentaRay catheter was fully deployed (see FIG. 7B). For this reason, validation of the iFM-iAM algorithm to detect rotational-footprints was performed using ex-vivo high-quality optical mapping movies, which are universally considered as the true 'gold-standard'. However, they have the inconvenience that they cannot be obtained in-vivo, so they cannot be incorporated to the clinical practice. Note that, unlike the iFM-iAM algorithm that works with single signals, phase mapping of optical mapping movies does require multiple signals. However, the rest of the aforementioned technical limitations of phase mapping do not apply to optical mapping movies because of their high spatiotemporal resolution (6400 signals separated ~0.43-0.62 mm). Some examples of detection of rotational-footprints with the iFM-iAM algorithm vs. the 'gold-standard' (phase singularities, PS, detected by phase mapping of high-resolution optical mapping movies) are shown in FIGS. 2, 15 and 16.

Also, some could argue that our 'driver' IFM maps are similar to bipolar dominant frequency (DF) maps used in previous approaches that offered suboptimal results in PersAF. However, important conceptual and practical differences are present. First, DF is a spectral measurement (obtained from the frequency-domain) that selects the frequency of the highest spectral peak as a surrogate of the signal activation frequency. On the contrary, iFM maps are obtained from time-domain measurements that are more robust than spectral measurements for a wider range of electrical signals when properly designed algorithms are used. Unlike DF, iFM tracks dynamic changes in the local activation rate throughout the duration of the signal and enables the detection of intervals with rotational-footprint or high-frequency bursts. Second, morphology and iAM/iFM content of electrical signals often result in multiple spectral peaks with similar heights which makes DF analysis challenging. Moreover, the time intervals with the highest iFM usually display the lowest amplitudes and vice versa. The latter affects the height of their corresponding power spectral peaks. Therefore, the usually higher signal amplitudes in the slowest time intervals strongly affect DF calculation (see FIG. 1B). Third, we mainly relied on unipolar signals from 1-mm size electrodes instead on bipolar signals whose amplitudes depend on the wavefront orientation, are not directly proportional to those in the underlying action potentials and are more prone to fractionation. A comparison between iFM and DF performance in maps and sample tracings from a particular animal can be found in FIGS. 13 and 14.

In addition, we found an extraordinary intra-case reproducibility (95.7%) in the location of 'high-hierarchy' driver regions between the maps acquired ~2.5 hours apart (see FIG. 17B, right panel and FIG. 17C, bottom row, right panel). The small percentage (4.3%) that were not reproducible in the two maps might be due to early or delayed after depolarization islands arising spontaneously in different regions and shifting location on a beat-to-beat basis. PersAF termination and non-sustainability after ablating 'high-hierarchy' regions in the majority of procedures confirmed that a small number of localized regions can maintain PersAF at least in the medium-term. Although spatiotemporal stability in the short-term (minutes) of contact and non-contact AF maps has been previously reported with controversial results, medium-term driver stability has usually been assumed underlying the rationale for some PersAF patient-tailored ablation approaches. However, to our knowledge, such a stability had not been conclusively demonstrated until now by performing two very detailed high-density contact maps acquired several hours apart. This might be because previous mechanistic approaches have been directly tested in patients, and too long, ethically-dubious procedures would be required for this purpose. Moreover, most patient-tailored ablation approaches do not consider the dynamic frequency content or hierarchy of the rotational/centrifugal activation regions identified as 'AF drivers'. According to our findings, not every region with focal or rotational activations should be targeted but only the 'high-hierarchy' ones. Importantly, almost half of these 'high-hierarchy' driver regions were found in the coronary sinus/left atrium floor or left atrial appendage/left atrial free wall (see FIG. 17C, bottom row, middle panel). However, MESPAS using basket catheters or ECG imaging are not optimal to map these regions. Around a third of 'high-hierarchy' driver regions were located in the posterior right atrium/superior cava vein junction. Those locations are consistent with some approaches that routinely isolate the left atrial appendage or ablate triggers that can (re) initiate AF in those regions.

There is no controversy about the role of focal triggers from fixed locations (e.g. pulmonary veins) in (re) initiating AF. However, the fact that PersAF episodes can be usually terminated (at least transiently) and not only reset by electrical cardioversion does not support a purely non-reentrant focal mechanism to maintain AF. Also, some so-called foci might actually represent breakthroughs generated by intramural scroll-waves (3D rotors) with nonlinear filament shapes (see FIG. 15C). Conversely, some short-lived rotational-footprints observed may be the consequence of wave collisions initiating transient rotational activity. Despite the aim of this invention was not to conclusively discern among centrifugal or rotational mechanisms in these regions, the presence of rotational-footprints for ≥5 consecutive cycles in >97% of 'high-hierarchy' regions argues in favour of scroll-waves/rotors or microanatomic intramural reentry as the main underlying mechanism for PersAF maintenance in our pig model of long-standing PersAF. Worthy of note is the fact that around three quarters of the rotational-footprints were found outside 'high-hierarchy' regions (see FIG. 17E, right panel). That suggests that current approaches ablating rotational/centrifugal activation or spatiotemporal dispersion regions regardless its iFM may be highly sensitive but little specific to detect true driver regions. Indeed, we have seen a plethora of rotors performing several rotations and appearing repeatedly in low-hierarchy regions that were not relevant to maintain PersAF (see a sample case in FIG. 7).

Previous patient-tailored mechanistic-based ablation approaches in PersAF have attempted different targets for ablation: i) high DF sites; ii) rotational and centrifugal activation detected with MESPAS and propriety algorithms; iii) visually-detected spatiotemporal dispersion; and iv) rotor domains detected with a PentaRay catheter and phase mapping of electrical data. Our invention proposes a completely different approach that has shown a great success rate in a clinically-relevant animal model of long-standing PersAF. Our invention successfully terminated PersAF in the vast majority of procedures (92.3%) and AF was rendered non-sustainable after 16.9 and 20.4 minutes of radiofrequency delivery, respectively (see FIGS. 17D, 18 and 19).

Our data supports the assertion that PersAF is often maintained by a few atrial regions with the highest average iFM values that are, at least, spatiotemporally stable for several hours. Rotational activation is sensitive but not specific to these 'high-hierarchy' driving regions. Both rotational-footprints and steady 'high-hierarchy' driver regions can be accurately detected by iFM-iAM analysis of single-signals without requiring costly propriety MESPAS. This approach can be easily implemented into any routinely used electroanatomical mapping system to considerably reduce the cost associated to patient-tailored mechanistic ablation procedures for Pers AF.

Consequently, a first aspect of the invention refers to the, preferably ex vivo (outside of the human or animal body) use of the instantaneous frequency modulation (iFM) signal calculated as the reciprocal of the intervals between consecutive cardiac activations during cardiac fibrillation, wherein said activations are detected over i) a single or multiple electrical unipolar signals obtained via a single or multiple mapping electrodes, or ii) a single or multiple optical signals obtained via a single or multiple optical fibers, wherein preferably the spatial locations at the times of acquisition are used for constructing an electroanatomical map of the heart in a subject in need thereof, for detecting 'driver' or 'high-hierarchy' regions in the heart of a subject with cardiac fibrillation. Alternatively, the first aspect of the invention, also refers to the use of the frequency modulated (FM) signal in a context of cardiac fibrillation obtained as a sinusoidal signal that incorporates the iFM present during cardiac fibrillation calculated as described above, for detecting 'driver' or 'high-hierarchy' regions in the heart of a subject with cardiac fibrillation.

In addition, a second aspect of the invention refers to a, preferably an in vitro or ex vivo (outside of the human or animal body), method for detecting 'driver' or 'high-hierarchy' regions in the heart of a subject with cardiac fibrillation, preferably with atrial fibrillation, more preferably with persistent atrial fibrillation, which comprises the following steps:

a. Constructing an electroanatomical map of the heart, or of a portion of the heart such as one atrium, both atria, one ventricle or both ventricles, of the subject obtained via a mapping device with i) one or more electrodes and/or ii) one or more optical fibers embedded, and obtaining i) electrical unipolar signals via the electrodes and/or ii) optical signals via the optical fibers;
b. Detecting activations over i) the electrical unipolar signals or ii) the optical signals via any known method for detecting activations in cardiac signals. Preferably said activations are selected over i) the ANS signal as described below, or ii) the APS signal as defined below.
c. From the activations of step b), the instantaneous frequency modulation (iFM) signal is obtained from the i) unipolar electrical signal/s or ii) optical signal/s, by calculating the reciprocal of the intervals between consecutive activations in seconds (the shorter the interval between consecutive activations, the higher the iFM value);
d. Then, the mean, median or specific percentile values (e.g. $10^{th}$, $20^{th}$, $30^{th}$, $40^{th}$, $50^{th}$, $60^{th}$, $70^{th}$, $80^{th}$, or $90^{th}$ percentiles) of the iFM are calculated for each signal in the electroanatomical map and displayed over said electroanatomical map of the heart;

wherein a driver map obtained by interpolating the mean, median or specific percentile values of iFM at each of the points used to generate the map, is used to detect cardiac spots with mean, median or specific percentile values of iFM higher than their surroundings that are considered as the regions potentially driving cardiac fibrillation ('drivers' or 'high-hierarchy' regions).

As used herein, 'driver' or 'high-hierarchy' regions in the heart of a subject with cardiac fibrillation is understood as regions with values of mean, median ($50^{th}$ percentile) or another specific percentile of iFM that are higher than the same values in the surrounding locations (cardiac tissue regions or 'islands' of high mean, median—$50^{th}$ percentile—or another specific percentile of iFM).

As used herein, the term "driver" is preferably understood as "leading-driver". As used herein, the term "high-hierarchy' drivers" is preferably understood as 'high-hierarchy' or 'leading-driver' regions.

In a preferred embodiment of the first or second aspect of the invention, the activations are detected by first calculating i) the 'absolute negative slope' (ANS) signal/s that is/are obtained as the absolute value of the time derivative of a single or multiple electrical unipolar signals obtained via a single or multiple mapping electrodes, in the intervals with negative slope (the only ones potentially hosting cardiac activations in electrical unipolar signals) and assigning a 0 value in the intervals with positive slopes; or by first calculating ii) the 'absolute positive slope' (APS) signal/s that is/are obtained as the absolute value of the time derivative of a single or multiple optical signals obtained via a single or multiple optical fibers, in the intervals with positive slope (the only ones potentially hosting cardiac activations in optical signals) and assigning a 0 value in the intervals with negative slopes.

In another preferred embodiment of the first or second aspect of the invention or of any of its preferred embodiments, the cardiac fibrillation is atrial fibrillation, and the intervals between consecutive cardiac activations during atrial fibrillation to provide the iFM are calculated by first detecting false atrial negative deflections due to ventricular electrical far-field in an electrical unipolar signal acquired from an atrium of a heart of a subject during atrial fibrillation, which comprises the following steps:

a. Acquiring two unipolar electrical signals from two close atrial locations in the heart of the subject during atrial fibrillation via at least two electrodes.
b. Acquiring one signal via surface ECG or an electrical signal from one ventricular location in the heart of the subject during atrial fibrillation for detecting ventricular activations via at least one electrode.
c. Obtaining a bipolar electrical signal from the 2 unipolar electrical signals acquired in step a) using any known method for this purpose (e.g. subtraction of both unipolar electrical signals and subsequently 30-500 Hz band pass filtering).
d. Detecting intervals containing false unipolar atrial negative deflections as intervals when simultaneously: i) the unipolar electrical signals from the atria acquired in step a) present negative slope; ii) the surface ECG signal or the ventricular one acquired in step b) display ventricular activation; and iii) the bipolar electrical signal obtained in step c) contains negligible voltages;

wherein the instantaneous frequency modulation (iFM) signal is thus calculated as the reciprocal of the intervals between consecutive atrial activations during atrial fibrillation discarding activations contained in the false unipolar atrial negative deflections detected in step d).

It is noted that the above method (steps a) to d)) for detecting false atrial negative deflections due to ventricular electrical far-field in an electrical unipolar signal acquired from an atrium of a heart of a subject during atrial fibrillation, also constitutes a different aspect of the present invention independently of whether it is used or not to calculate the iFM.

In another preferred embodiment of the first or second aspect of the invention or of any of its preferred embodiments, the cardiac fibrillation is atrial fibrillation, and the atrial activations in unipolar electrical signals acquired from the atria of a subject with atrial fibrillation to provide the iFM values, preferably with persistent atrial fibrillation, are calculated by a method which comprises the following steps:

a. Acquiring at least two unipolar electrical signals from two close atrial locations in the heart of the subject during atrial fibrillation via at least two electrodes.
b. Acquiring one signal via surface ECG or an electrical signal from one ventricular location in the heart of the subject during atrial fibrillation for detecting ventricular activations via at least one electrode.
c. Obtaining a bipolar electrical signal from the 2 unipolar electrical signals acquired in step a) using any known method for this purpose (e.g. subtraction of both unipolar electrical signals and subsequently 30-500 Hz band pass filtering).
d. Applying any known ventricular far-field subtraction method to the atrial unipolar signal acquired in step a) (e.g. using principal component analysis to estimate the ventricular far-field signal).
e. Calculating the ANS signal from the signal obtained after performing step d) as described above.
f. Detecting local maxima in the ANS signal. The times at which the local maxima are detected are considered potential atrial activations. Preferably said maxima are selected upon compliance with both condition A (a minimum height and prominence) and condition B (a minimum separation from the previous and next detected local maxima). More preferably, the following specific conditions are used:

$$\text{Minimum height and prominence}=\max\{0.03, 0.05\cdot P_{95^{th}}(\text{ANS})\} \quad \text{Condition A:}$$

wherein $95^{th}$ percentile of ANS signal values is used as reference instead the maximum value to prevent excessive thresholds due to artifactually high values in the electrical unipolar signal slope, and 0.03 is used as noise level threshold.

Condition B:

$$\text{Min. separation between activations} == \max\left\{50\text{ ms}, \frac{1000}{1.95\cdot\text{median}\{DF_{UNI}, DF_{ANS}, DF_{BIP}\}}\text{ ms}\right\}$$

or alternatively, condition B:

$$\text{Min. separation between activations} == \max\left\{50\text{ ms}, \frac{1000}{1.95\cdot\min\{DF_{UNI}, DF_{ANS}, DF_{BIP}\}}\text{ ms}\right\}$$

wherein $DF_{UNI}$ is the dominant frequency of the unipolar electrical signal, $DF_{ANS}$ the dominant frequency of the ANS signal and $DF_{BIP}$ the dominant frequency of the bipolar electrical signal. $DF_{UNI}$, $DF_{ANS}$ and $DE_{BIP}$ are calculated as the frequencies with the highest peak in the power spectral density (PSD) of the unipolar, ANS and bipolar signals, respectively. PSD is calculated by any known method (e.g. Welch's periodogram).
g. Rejecting the false atrial activations contained in the residual false atrial negative unipolar deflections detected by the method described above.
h. Identifying the activations used to calculate the iFM.

Preferably, after step g) an iterative method to allow only physiological variations in the intervals between consecutive activations is performed. Such methodology can be performed as described in [Ng et al. Iterative Method to Detect Atrial Activations and Measure Cycle Length From Electrograms During Atrial Fibrillation. IEEE Trans Biomed Eng. 2014 February; 61 (2): 273-278]

It is noted that the above method (steps a) to g)) for detecting atrial activations in unipolar electrical signals acquired from the atria of a subject with atrial fibrillation, also constitutes a different aspect of the present invention independently of whether it might be used or not to calculate the IFM.

In another preferred embodiment of the first or second aspect of the invention or of any of its preferred embodiments, the cardiac fibrillation is atrial or ventricular fibrillation, and the method used to detect cardiac activations in optical signals acquired from the heart of a subject with cardiac fibrillation, preferably with atrial fibrillation, more preferably with persistent atrial fibrillation, comprises the following steps:

a. Acquiring one or more optical signals from the heart, or from a portion of the heart such as one atrium, both atria, one ventricle or both ventricles, of the subject obtained via a device with one or more optical fibers embedded, and obtaining optical signals via the optical fibers;
b. Calculating the APS signal/s from the signal/s obtained after performing step a) as described above.
c. Detecting local maxima in the APS signal/s. The times at which the local maxima are detected are considered potential cardiac activations. Preferably said maxima are selected upon compliance with both condition A (a minimum height and prominence) and condition B (a minimum separation from the previous and next detected local maxima). More preferably, the following specific conditions are used:

$$\text{Minimum height and prominence}=0.02\cdot P_{95^{th}}(\text{APS}) \quad \text{Condition A:}$$

wherein $95^{th}$ percentile of APS signal values is used as reference instead the maximum value to prevent excessive thresholds due to artifactually high values in the optical signal slope.

Condition B:

$$\text{Min. separation between activations} == \max\left\{50\text{ ms}, \frac{1000}{1.95\cdot\min\{DF_{Optical}, DF_{APS}\}}\text{ ms}\right\}$$

wherein $DF_{optical}$ is the dominant frequency of the optical signal and $DF_{APS}$ the dominant frequency of the APS signal. $DF_{optical}$ and $DF_{APS}$ are calculated as the frequencies with the highest peak in the power spectral density (PSD) of the optical signal and APS signal respectively. PSD is calculated by any known method (e.g. Welch's periodogram).
d. Identifying the activations used to calculate the IFM.

Preferably, after step c) an iterative method to allow only physiological variations in the intervals between consecutive activations is performed. Such methodology can be performed as described in [Ng et al. Iterative Method to Detect Atrial Activations and Measure Cycle Length From Electrograms During Atrial Fibrillation. IEEE Trans Biomed Eng. 2014 February; 61(2): 273-278].

It is noted that the above method (steps a) to c)) for detecting cardiac activations in optical signals acquired from the heart of a subject with cardiac fibrillation, also constitutes a different aspect of the present invention independently of whether it is used or not to calculate the iFM.

A third aspect of the invention refers to the, preferably an in vitro or ex vivo (outside of the human or animal body), use of the iFM signal calculated as the reciprocal of the intervals between consecutive activations and the iAM signal calculated from the amplitude excursions of the signal deflections that contain activations, wherein the lower these amplitude excursions, the higher the iAM, during cardiac fibrillation, wherein said activations are detected over i) a single or multiple electrical unipolar signals obtained via a single or multiple mapping electrodes, or ii) a single or multiple optical signals obtained via a single or multiple optical fibers, wherein preferably the spatial locations at the times of acquisition are used for constructing an electroanatomical map of the heart in a subject in need thereof, for detecting cardiac spots with rotational activations in the heart of a subject during cardiac fibrillation. Alternatively, the third aspect also refers to the use of the frequency and amplitude modulated (FM IAM) signal in a context of cardiac fibrillation obtained as a sinusoidal signal that incorporates the iFM and iAM present during cardiac fibrillation calculated as described above, for detecting cardiac spots with rotational activations in the heart of a subject during cardiac fibrillation.

On the other hand, a fourth aspect of the invention, provides a, preferably ex vivo (outside of the human or animal body), method to detect cardiac spots with rotational activations in the heart of a subject during cardiac fibrillation using single signals, as opposed to multiple signals, which comprises:

a. Acquiring i) electrical unipolar signals or ii) optical signals of the heart, or of a portion of the heart such as one atrium, both atria, one ventricle or both ventricles, of the subject via a mapping device with i) one or more electrodes and/or ii) one or more optical fibers embedded, and obtaining i) the electrical unipolar signals via the electrodes and/or ii) the optical signals via the optical fibers;

a. Detecting activations over i) the electrical unipolar signals or ii) the optical signals via any known method for detecting activations in cardiac signals. Preferably said activations are selected over i) the ANS signal described above; or ii) the APS signal as described above.

b. Calculating the iFM as described in the first or second aspect of the invention or as described in any of its preferred embodiments; and calculating the iAM from the sequence of amplitude excursions of i) the negative deflections that contain activations in unipolar electrical signals or ii) the optical phases 0 that contain activations in optical signals: wherein the lower these amplitude excursions, the higher the iAM; and c. Detecting intervals with i) simultaneous increase in IFM and iAM (reaching a certain iAM threshold), which is indicative of drifting rotors approaching a cardiac spot or ii) simultaneously high iAM and iFM values, which is indicative of stationary rotors or rotors meandering around a cardiac spot. Preferably said intervals are selected upon compliance with at least one of the conditions A or B:

Condition A: a simultaneous increase in IFM and iAM, which is indicative of drifting rotors approaching a cardiac spot (e.g. rotors 1 and 2 in rows 9/10 of FIG. 3). Specifically, the following logical condition should be preferably fulfilled: Increasing iFM(t) for at least parameter_1 cycles AND [(increasing iAM(t) with a minimum excursion of parameter_2% for at least parameter_3 cycles reaching at least parameter_4%) OR iAM(t)≥parameter_4%].

Condition B: simultaneous high iAM and iFM values, which is indicative of stationary rotors or rotors meandering around a cardiac spot (e.g. rotor 3 in rows 9/10 of FIG. 3). Specifically, the following logical condition should be preferably fulfilled: iFM(t)≥parameter_5 percentile AND iAM(t)≥parameter_4% for at least 2 cycles.

Note that if iAM remains above parameter_4%, rotational footprint is still detected after the end of the increasing iFM cycles in condition A. In other words, after simultaneously increasing iAM and iFM intervals, the algorithm could be made to consider that the rotor is still around there while iAM keeps over the parameter_4% threshold regardless their IFM. That specific detail of the algorithm is warranted by the extremely low amplitude/high frequency of the activations during such intervals, which can result in infra-detection of actual complete/partial depolarizations for not fulfilling the algorithm criteria resulting in low, non-increasing values of iFM. Examples of this kind of situation are shown in FIG. 4.

Note that one or more specific parameters can be disabled in the algorithm if they are assigned the following values:

parameter_1=0 (disabled)
parameter_2=0 (disabled)
parameter_3=0 (disabled)
parameter_4=0 (disabled)
parameter_5=100 (disabled)

Very good values of sensitivity and specificity can be achieved by only using 2 parameters and setting the remaining 3 ones to their 'disabled' values. For example, the following parameters achieved a mean sensitivity of 92.2% and a mean specificity of 87.7% with a 1.25 mm tolerance:

parameter_1=3
parameter_2=0 (disabled)
parameter_3=0 (disabled)
parameter_4=85
parameter_5=100 (disabled)

Also, the following parameters achieved a mean sensitivity of 95.4% and a mean specificity of 93.3% with a 2.50 mm tolerance:

parameter_1=4
parameter_2=0 (disabled)
parameter_3=0 (disabled)
parameter_4=80
parameter_5=100 (disabled)

Even better values of sensitivity and specificity can be achieved by only using 3 parameters and setting the remaining 2 ones to their 'disabled' values. For example, the following parameters achieved a mean sensitivity of 91.8% and a mean specificity of 90.6% with a 1.25 mm tolerance, and a mean sensitivity of 97.2% and a mean specificity of 93.3% with a 2.50 mm tolerance:

parameter_1=3
parameter_2=0 (disabled)
parameter_3=2
parameter_4=85
parameter_5=100 (disabled)

When adding a fourth parameter while setting the remaining one disabled, sensitivity and specificity can be further improved. For example, the following parameters achieved a mean sensitivity of 93.2% and a mean specificity of 90.4% with a 1.25 mm tolerance:

parameter_1=4
parameter_2=0 (disabled)
parameter_3=2
parameter_4=80
parameter_5=70

Also, the following parameters achieved a mean sensitivity of 97.1% and a mean specificity of 94.8% with a 2.50 mm tolerance:

parameter_1=4
parameter_2=0 (disabled)
parameter_3=3
parameter_4=80
parameter_5=70

To further optimize the values of sensitivity and specificity achieved by the algorithm, all the 5 parameters can be used. The parameters for which the algorithm reached its maximal sum of sensitivity (93.1%) and specificity (90.6%) with a 1.25 mm tolerance are as follows:

parameter_1=4
parameter_2=25
parameter_3=3
parameter_4=80
parameter_5=70

The parameters for which the algorithm reached its maximal sum of sensitivity (97.0%) and specificity (95.1%) with a 2.50 mm tolerance are as follows:

parameter_1=4
parameter_2=35
parameter_3=3
parameter_4=80
parameter_5=70

Table 1 displays the tested combinations of parameters. Table 2 displays the optimal combinations for all tolerances and for any number of 'enabled' parameters (from one parameter to all five parameters) to: A) maximize the sum of sensitivity and specificity; B) maximize sensitivity provided specificity ≥95%; or C) maximize specificity provided sensitivity ≥95%.

A fifth aspect of the invention refers to an ablation therapeutic method, which is carried out by constructing an electroanatomical map of the heart and performing a driver map as defined in the second aspect of the invention, and selecting ablation sites within the driver regions, and ablating cardiac tissue at the ablation sites.

A sixth aspect of the invention refers to an ablation therapeutic method, which is carried out by detection of cardiac spots with rotational activations in the heart of a subject with cardiac fibrillation as defined in the fourth aspect of the invention, and selecting ablation sites within the cardiac spots with rotational activation, and ablating cardiac tissue at the ablation sites. This selection of ablation sites may be restricted to cardiac spots in which the conditions A or B in the fourth aspect of the invention are met for consecutive or total intervals lasting longer than a specific time or number of cycles.

There is further provided according to a seventh aspect of the invention a medical apparatus, including a probe or catheter, adapted for insertion into a heart, the probe including an elongated body, and one or more mapping electrodes or optical fibers disposed on a distal portion of the body, a memory having programs stored therein, a display, and a processor linked to the display that is coupled to access the memory to execute the programs. The processor is connectable to receive an input provided by the mapping electrodes or optical fibers, wherein the programs cause the processor to perform the steps of obtaining a single or multiple electrical unipolar signals or optical signals from a target in the heart via the mapping electrodes or optical fibers, generating an electroanatomical map based on the assigned electrical or optical data, performing the method of the second or fourth aspect of the invention, and presenting the electroanatomical map on the display in a way in which the 'driver' or 'high-hierarchy' regions and/or cardiac spots with rotational activations in the heart of a subject are identified.

An eighth aspect of the invention refers to a computer program for processing by a computer for identifying 'driver' or 'high-hierarchy' regions and/or cardiac spots with rotational activations in the heart of a subject with cardiac fibrillation, wherein said computer program performs at least one step, preferably all of the steps, of the method of the second and/or fourth aspect of the invention, and preferably presents an electroanatomical map in a way in which the 'driver' or 'high-hierarchy' regions and/or cardiac spots with rotational activations in the heart of a subject are identified.

A computer-readable medium having embodied thereon a computer program according to the eighth aspect of the invention.

The following examples are merely for illustrative purposes and do not limit the present invention.

EXAMPLES

Example 1. Instantaneous Amplitude and Frequency Modulations (iAM/iFM) Detect Rotational Footprints and Steady High Hierarchy Regions in Persistent Atrial Fibrillation without Requiring Simultaneous Panoramic Acquisition

SUMMARY

Rationale: Costly propriety multielectrode simultaneous panoramic acquisition systems (MESPAS) are being increasingly used together with conventional electroanatomical mapping systems (EAMS) to improve outcomes in persistent atrial fibrillation (PersAF) by ablating rotational/focal alleged drivers regardless their instantaneous frequency modulation (iFM).

Objectives: To demonstrate that steady myocardial regions with higher average iFM than their surroundings sustain PersAF and that rotational activity is sensitive but not specific to them. For that purpose, we developed novel single-signal algorithm based on instantaneous frequency and amplitude modulations (iFM-iAM) to detect rotational-footprints and high-hierarchy regions without requiring MESPAS.

Methods and results: iFM-iAM algorithms were tested in 125 optical movies from 5 PersAF sheep. In-vivo high-density electroanatomical atrial maps were generated by registering 8-second unipolar signals and their spatial locations in 16 pigs with PersAF (median [P25$^{th}$-P75$^{th}$]:96[82-108] kg). Myocardial regions of high average iFM were considered drivers. Two combined driver/rotational-footprint maps were generated 2.6[2.4-2.9] hours apart to test spatiotemporal stability and guide ablation in 12 pigs that developed PersAF after 3.7[2.2-9.7] months of atrial tachypacing. In the two maps acquired 4.1[2.8-5.2] months later (4920[4435-5855] signals/map), high-hierarchy regions (2.5 [2.0-4.0] regions/map) were mostly coincidental (95.7%) and their ablation terminated PersAF in 92.3% of procedures (radiofrequency time until termination: 16.9[9.2-35.8] min; until non-sustainability: 20.4[12.8-44.0] min). Rotational-footprints were found at every high-hierarchy region, albeit most (76.8%[70.5%-83.6%]) were located outside. Translation ability of this approach was successfully tested in 3 redo PersAF patients.

Conclusions: PersAF is often maintained by few high-hierarchy regions that are spatiotemporally stable for at least hours. Rotational activation is sensitive but not specific to these regions. Therefore, approaches ablating every region with rotors/foci/spatiotemporal-dispersion regardless its average iFM may have low specificity. Both rotational-footprints and high-hierarchy regions can be located by single-signal iFM-iAM algorithms without MESPAS. These algorithms can be integrated into conventional EAMS to considerably reduce costs in patient-tailored/mechanistic ablation procedures.

Non-Standard Abbreviations and Acronyms

AF: atrial fibrillation
AM: amplitude modulation
CS: coronary sinus
DF: dominant frequency
FM: frequency modulation
HRAP: high rate (20 Hz) atrial pacing
iAM: instantaneous amplitude modulation
iFM: instantaneous frequency modulation
LA: left atrium
LAA: left atrial appendage
MESPAS: multielectrode (64-256) simultaneous panoramic acquisition systems
PersAF: persistent atrial fibrillation
PS: phase singularity
PVI: pulmonary vein isolation
RA: right atrium
RAA: right atrial appendage
RV: right ventricle
VF: ventricular fibrillation Methods All animal procedures were approved by the local Committees on Use and Care of Animals and complied with institutional, NIH, Spanish (RD53/2013, ECC/566/2015) and European (2010/63/EU) guidelines. The Hospital Clínico San Carlos Ethics committee approved the procedures in patients, and subjects gave informed consent.

Ovine and Porcine Experimental Models of Persistent AF

The high rate atrial pacing (HRAP) protocol used to generate sheep with PersAF has been previously reported in detail. The fast atrial pacing protocol used to generate sheep with persistent AF has been previously reported in detail. Briefly, the pacemaker was programmed with an algorithm consisting of 30-second pacing at 20 Hz followed by 10-second sensing. Importantly, to generate a clinically relevant persistent AF model, the pacing algorithm was stopped after 20-24 weeks. Persistent AF was defined based on the criteria used for human AF as those episodes lasting >7 days upon switching off the fast pacing program.

In pigs, pacemakers with episode-recording capabilities were implanted in 18 ~6-month-old animals (weight ~45 kg). Atrial and ventricular leads were inserted into the RAA and RV apex, respectively. After 10 days of recovery, the atrioventricular node was ablated and ventricular pacing started. Unlike sheep, HRAP would result in failing ventricles otherwise. In 16/18 pigs, pacemakers were programmed to induce AF by 30-second burst tachypacing (20 Hz, twice diastolic threshold) followed by 6-second sensing. Upon sinus rhythm detection, pacing was automatically resumed. Atrial electrograms were stored to accurately confirm the occurrence, generate burden curves and follow AF evolution from initial paroxysmal episodes to the establishment of PersAF (episodes lasting >7 days without HRAP). The remaining 2/18 constituted the sham-operated group. Pacemakers were interrogated and an echocardiogram was performed every 3 weeks.

Ex-Vivo Optical Mapping of Sheep Hearts with Persistent AF

As previously reported in more detail, five hearts from sheep (~66 kg) with persistent AF after 5-6 months of continuous tachypacing-induced AF were used for optical mapping. Hearts were Langendorff-perfused with Tyrode's solution. After an atrial trans-septal puncture, all the vein orifices were sealed except the inferior vena cava, which was connected to a digital sensor and to an open-end cannula to control the intra-atrial pressure. The pressure was then increased to a subthreshold AF-inducing level of 5 $cmH_2O$, resembling the diastolic LA pressure and maintained throughout the experiment. Epicardial optical mapping (Di-4-ANEPPS 5-10 mg/mL, Blebbistatin 10 μM, 532 nm laser excitation) of the left atrial appendage (LAA) was performed. The emitted fluorescence (645 nm) was projected onto a CCD camera (80×80 pixels, 600 frames/sec). Spontaneous AF was allowed to continue uninterruptedly for 50 minutes. Optical movies (5 seconds) were acquired at 2-minute intervals (25 movies/sheep, 125 movies total).

Ex-Vivo Optical Signa/Processing

Phase Mapping and Phase Singularity Detection

After low pass spatiotemporal filtering with a conical-shaped kernel, and removal of drift when present (subtraction of the output of a running average filter), phase movies were obtained by means of Hilbert transformation of the optical action potentials. A phase singularity (PS) was defined as the pivoting point where all phases converged during rotational activation. PS detection was implemented as previously described, using custom-made software in Matlab.

Time-Domain iFM and iAM and Rotational-Footprint Detection

The following steps were performed for every signal in the optical movie (80×80=6400 signals): 1) detection of activations at the times when phase 0 slopes are maximal; 2) measurement of phase 0 amplitudes; 3) calculation of iFM from the sequence of activation times (the shorter the interval between consecutive activations, the higher the iFM); 4) calculation of iAM from the sequence of phase 0 amplitudes (the lower the amplitude, the higher the iAM). FIG. 2 shows examples obtained from a movie with highly complex dynamics. The closer the signal is obtained from a spot crossed by rotors, the more iAM increases (thick red intervals). Also, intervals of increasing iFM (Doppler Effect, thick blue intervals) are present as drifting rotors approach a spot. Therefore, single-signal detection of a rotational-footprint was based on: i) a simultaneous increase in iFM and iAM (reaching a certain iAM threshold), which is indicative of drifting rotors approaching a spot (FIG. 2A, rotors 1-2), or ii) simultaneously high iAM and iFM values, which is indicative of quasi-stationary rotors or rotors meandering around a location (FIG. 2A, rotor 3). In-depth descriptions of the single-signal algorithms used are provided:

FIG. 3 describes in detail the algorithm used to calculate instantaneous frequency modulation (iFM), instantaneous amplitude modulation (iAM) and rotational-footprint detection using the optical signal displayed in FIG. 2A as example.

This optical signal (row 1 in FIG. 3) corresponds to a specific pixel of the optical movie (80×80=6400 pixels) previously filtered as described above. Note that the same processing was performed for every pixel in the optical movies. First, the slope (first derivative: dV/dt) of the optical signal was computed. Since activation times in optical action potentials are usually defined at the times of maximum positive slope within the 'phase 0', the intervals in which the slope was negative did not provide useful information regarding activation times and were assigned a zero value. This way, a signal with peaks corresponding only to intervals of positive slope was obtained (absolute positive slope, APS, row 2). This signal can be easily calculated as follows:

$$APS(t) = \frac{1}{2}\left(\left|\frac{d\ OAP(t)}{dt}\right| + \frac{d\ OAP(t)}{dt}\right)$$

Then, the times when peaks in APS(t) met the following criteria were selected as activation times: i) a value above a minimum slope threshold (minimum slope), ii) a prominence above a certain value (minimum prominence), and iii) separated at least a minimum refractory period from the previous and the next peaks.

The minimum slope was set as the fiftieth part (2%) of the $95^{th}$ percentile of the peak amplitude values. Similarly, the minimum prominence was set as the fiftieth part (2%) of the $95^{th}$ percentile of the peak prominence values:

$$APS_{min}=0.02\cdot P_{95th}(APS)\ au/ms$$

The $95^{th}$ percentiles were used as reference instead the maximum value ($100^{th}$ percentile) to prevent excessive thresholds due to artifactually high values in the optical signal slope:

The minimum refractory period was set for each pixel as:

$$RP_{min} = \max\left\{50\ ms,\ \frac{1000}{1.95\cdot \min\{DF_{OAP}, DF_{APS}\}}\ ms\right\}$$

where $DF_{OAP^{AP}}$ is the dominant frequency of the optical action potentials and $DF_{APS}$ the dominant frequency of the APS(t) signal. $DF_{O_{AP}}$ and $DF_{APS}$ were calculated as the frequencies with the highest peak in the power spectral density (PSD) of the OAP(t) and APS(t) signals respectively. PSD was estimated by a conventional periodogram of the signal previously multiplied by a Kaiser window (β=2.5) and zero-padded to the next higher power of 2.

Both dominant frequencies are used as a rough surrogate of the reciprocal of the average interval between activations. The 1000 factor is used to convert that time into ms. Since activation intervals shorten and lengthen dynamically during fibrillation, the 1/1.95 factor is used to allow for intervals up to 1.95 times shorter than the surrogate average one [(1/DF) *1000 ms]. Such a value usually provides a reasonable lower limit for the local refractory period. Nevertheless, if that value was lower than 50 ms, the latter was used as the minimum refractory period for the algorithm. The resulting activation times are displayed as blue dots in row 3 of FIG. 3. However, although such a lower limit for the refractory period can account for physiological dynamic shortening of the local activation intervals, it sometimes may result in too short, artificial intervals. Therefore, an iterative adaptive algorithm was used to refine activations by allowing only physiological changes in atrial activation cycles. In this specific signal, no changes in activation times were performed by the adaptive iterative algorithm (FIG. 3, row 4).

In addition, the amplitude of the 'phase 0' of the action potentials was calculated as the fluorescence excursion (arbitrary units) between the times at which the slope goes below the 4% of the slope at the activation time. The fluorescence values at the activation times and their corresponding lower and upper amplitude limits for the 'phase 0' are displayed as blue and red points respectively in row 5 of FIG. 3. By interpolating such excursion amplitudes, we obtained the "optical envelope" signal (FIG. 3, OE(f), row 6). Since these amplitudes dynamically change as well (i.e. are modulated by several factors), their corresponding instantaneous amplitude modulation (iAM) signal (FIG. 3, row 9, red trace) was calculated as follows:

$$iAM(t) = 100\left(1 - \frac{OE(t)}{\max\{OE(t)\}}\right)(\%)$$

Note that the lower the optical envelope, the higher the iAM. Thus, intervals with low iAM values correspond to times when the optical envelope is unaffected, whereas intervals with high iAM values correspond to times when the optical envelope is highly affected by some factor/s (e.g. a drifting rotor is passing nearby).

Also, a frequency modulated signal (FM(t)) was obtained by adjusting a sinusoidal wave in order to reach its maxima at the previously detected activation times (FIG. 3, row 7). This way, the dense or sparse the distribution of the oscillations in this FM sinusoidal wave is, directly reflects the dynamic changes in the tissue activation rate at that specific location in an intuitive way.

Furthermore, a frequency- and amplitude-modulated (FM|AM) signal was obtained by multiplying the FM signal and the optical envelope signal (FIG. 3, row 8):

$$FM|AM(t)=OE(t)\cdot FM(t)$$

In addition to directly reflect in an intuitive way the dynamic changes in the tissue activation rate at that specific location, this FM|AM signal displays in a clear way the dynamic changes in the amplitude of the 'phase 0'.

Finally, the instantaneous frequency value between 2 consecutive activation times was calculated as the inverse of the interval between these activations in seconds. Analytically, given N consecutive activation times in ms ($t_o$, $t_l$, . . . , $t_N$), the iFM(t) signal is calculated as follows:

$$iFM(t) = \sum_{n=0}^{N-1} \frac{1000}{t_{n+1} - t_n}[u(t - t_n) - u(t - t_{n+1})]$$

where u(t) is the Heaviside unit step function, defined as $$u(t) = \begin{cases} 0, & t < 0 \\ 1, & t \geq 0 \end{cases}$$

Row 9 in FIG. 3 displays the resulting instantaneous frequency modulation (iFM) signal (blue trace).

Single-signal detection of a rotational-footprint was based on compliance with one of the following conditions:

- Condition A: a simultaneous increase in iFM and iAM, which is more specific for drifting rotors approaching a spot (e.g. rotors 1 and 2 in rows 9/10 of FIG. 3). Specifically, the following logical condition must be fulfilled:
- Increasing iFM(t) for at least parameter1 cycles AND [increasing iAM(t) with a minimum excursion of parameter2% for at least parameter3 cycles reaching at least parameter4%) OR iAM(t)≥parameter4%]
- Condition B: simultaneous high iAM and iFM values, which is more sensitive for quasi-stationary rotors or rotors meandering around a location (e.g. rotor 3 in rows 9/10 of FIG. 3) which do not necessarily present Doppler effect since they are not necessarily approaching the location but surrounding it. Specifically, the following logical condition must be fulfilled:
- iFM(t)≥parameter 5 percentile AND iAM(t) over parameter4% for at least 2 cycles In the example shown in FIGS. 2-5 and 15-16 the following parameters were used:

- parameter1=4 (minimum increasing iFM cycles)
- parameter2=25% (minimum iAM excursion)
- parameter3=3 (minimum increasing iAM cycles)
- parameter4=80% (iAM threshold)
- parameter5=$70^{th}$ percentile (minimum iFM percentile without increasing iFM together with iAM≥parameter4)

As reported in the results section, these parameters were the ones for which the algorithm reached its maximal sum of sensitivity and specificity with a 1.25 mm tolerance.

Note that if iAM remains above parameter4%, rotational footprint is still detected after the end of the increasing iFM cycles in condition A. In other words, after simultaneously increasing iAM and iFM intervals, the algorithm considers that the rotor is still around there while iAM keeps over the parameter4 threshold regardless their iFM. That specific detail of the algorithm is warranted by the extremely low amplitude/high frequency of the OAPs during such intervals, which can result in infra-detection of actual complete or partial depolarizations for not fulfilling the algorithm criteria. Examples of this kind of situation are shown in FIG. 4.

FIG. 5 shows the results of the algorithm if the minimum refractory period is fixed to 50 ms regardless the dominant frequencies of the OAP and APS signals. That change achieves that the low amplitude/high frequency partial depolarizations displayed in FIG. 4 due to the proximity of a meandering rotational core are not been ignored. However, despite the fact that this approach might be more sensitive to detect rotors that are stationary or meander around the pixel, introduces the risk of considering other potential causes of signal change (impulsive noise, depolarizations at the contralateral layer of the atria, etc.) as actual partial or complete depolarizations. That is the reason why the algorithm was henceforth applied with the lower limit of the refractory period calculated from the dominant frequencies of the OAP and APS signals (algorithm version shown in FIG. 3). Anyway, the 'rotational-footprint positive' intervals eventually detected by the two versions of the algorithm are practically the same. This was thanks to the algorithm detail described above and marked with an asterisk in FIG. 3 that enables to still detect the presence of a rotor in intervals of very low amplitude after simultaneously increasing iAM and iFM, but without the counterpart of oversensing risks.

Sensitivity and Specificity of the Rotational-Footprint Detection

Locations detected as 'rotational-footprint positive' by the iFM-iAM algorithm were compared with the locations positive for PS (pivoting points of rotational activation in phase movies). Algorithm sensitivity/specificity were calculated for 3 spatial tolerances: 0, 1.25 (ablation catheter radius) and 2.5 mm (ablation catheter diameter). An example with 1.25 mm tolerance is shown in FIG. 2D. Note that unlike phase mapping that requires multiple signals to detect rotations, the iFM-iAM algorithm detects rotational-footprints for each signal independently. More details are provided:

Sensitivity and specificity of the rotational footprint detection algorithm were calculated using the usual definitions:

$$\text{Sensitivity} = \frac{\text{True Positives}}{\text{True Positives} + \text{False Negatives}}$$

$$\text{Specitivity} = \frac{\text{True Negatives}}{\text{True Negatives} + \text{False Positives}}$$

- True positives: pixels actually crossed by a phase singularity (pivoting point of a rotational activation) that were classified as 'rotational-footprint positive' by the single-signal iFM/iAM algorithm.
- True negatives: pixels not crossed by a phase singularity that were classified as 'rotational-footprint negative' by the single-signal iFM/iAM algorithm.
- False positives: pixels not crossed by a phase singularity that were classified as 'rotational-footprint positive' by the single-signal iFM/iAM algorithm.
- False negatives: pixels actually crossed by a phase singularity that were classified as 'rotational-footprint negative' by the single-signal iFM/iAM algorithm.

Those were the definitions used at the pixel level, i.e. when tolerance was fixed to 0 mm. However, in a real scenario, the specific ablation of such tiny pixels would not be feasible.

Indeed, if an ablation catheter were centered at one pixel location positive for phase singularities and radiofrequency energy were delivered there, the created lesion would be much larger than the actual pixel size. Therefore, we also calculated sensitivity and specificity of the iFM/iAM algorithm allowing tolerances of 1.25 mm (radius of a conventional ablation catheter) and 2.5 mm (diameter of a conventional ablation catheter). Note that these tolerances are smaller than the actual lesions created by a conventional ablation catheter. Thus, the definitions were modified as follows when a tolerance of 1.25/2.5 mm was considered:

- True positives: pixels actually crossed by a phase singularity that were classified as 'rotational-footprint positive' or were within a 1.25/2.5 mm distance from those actually classified as 'rotational-footprint positive' by the single-signal iFM/iAM algorithm.
- True negatives: pixels not crossed by a phase singularity and beyond a 1.25/2.5 mm distance from those actually crossed by a phase singularity, that were classified as 'rotational-footprint negative' by the single-signal iFM/iAM algorithm.

False positives: pixels not crossed by a phase singularity and beyond a 1.25/2.5 mm distance from those actually crossed by a phase singularity, that were classified as 'rotational-footprint positive' by the single-signal iFM/iAM algorithm.

False negatives: pixels actually crossed by a phase singularity that were classified as 'rotational-footprint negative' and were beyond a 1.25/2.5 mm distance from. those actually classified as 'rotational-footprint positive' by the single-signal iFM/iAM algorithm.

In-Vivo Electroanatomical Mapping of Pigs with PersAF

Mapping and ablation procedures were guided with NavX Precision (Abbott). A decapolar catheter was advanced into the superior cava vein until reaching a position at which the signal of the distal bipole was negligible. Then, the distal electrode was used as unipolar reference. Maps were acquired in "CFE-mean" mode. Although CFE data were not used, it enabled us to store 8-second unipolar signals at each location. A PentaRay catheter (20 poles, Biosense Webster) was positioned sequentially for 8 seconds at different locations of the endocardium to reconstruct the right atrial (RA) and coronary sinus (CS) anatomy. An ECG lead was simultaneously stored to feed an off-line algorithm that minimized the ventricular far-field in the unipolar recordings. Catheter and electrogram stabilities during the 8-second window were ensured using the tool implemented in NavX Precision for that purpose. Once the RA map was finished, the PentaRay catheter was transeptally advanced and the LA was mapped in the same way. More than one hour later after finishing the first map, the same procedure started again to obtain another highly-detailed biatrial set of data. Spatiotemporal stability of the generated maps was assessed by comparing the maps obtained from the $1^{st}$ and $2^{nd}$ sets of data.

In-Vivo Electrical Signal Processing

Ventricular Far-Field Minimization

An estimation of the ventricular far-field was subtracted from unipolar signals. Estimation was based on Principal Component Analysis. After subtraction, residual little ventricular artifacts sometimes remain. For this reason, a novel second algorithm using ECG, unipolar and bipolar signals, was added in order to discern whether the resulting negative slope unipolar intervals during ventricular activation were ventricular far-field residues or true atrial activations. More details are provided:

An estimation of the ventricular far-field was subtracted from unipolar signals. Estimation was based on Principal Component Analysis (PCA), as described elsewhere. Specifically for this study, the PCA method was applied to a window around the R-peak of the QRS complex (orange intervals in FIG. 6A), which extended from the beginning of the Q-wave (or the spike of the stimuli if ventricular pacing was present: cyan spikes in FIG. 6A) to the end of the S-wave. The same window size was used for all the QRS complexes in a unipolar signal (size of the longest QRS complex in the corresponding simultaneous ECG, FIG. 6A-B). Note that the QRS complexes in the atrial unipolar signal result in spurious peaks in the absolute negative slope (ANS) signal that will be later used to detect activation times. Those peaks are marked with red arrows in FIG. 6C. In the PCA method, the QRS complexes from the unipolar traces are considered as realizations from stochastic processes for which a covariance matrix is derived. Then, the eigenvectors and eigenvalues of the covariance matrix are calculated with the eigenvectors placed in one matrix E and the eigenvalues placed in a diagonal matrix D. From these two matrices, a whitening matrix (a matrix that transforms the original observation matrix X into a matrix of whitened principal components) and a dewhitening matrix (a matrix which undoes the whitening process) are derived:

Whitening Matrix: $W=D^{-1/2}E^T$

Dewhitening Matrix: $W^{-1}=E\ D^{1/2}$

The principal components can then be obtained from the observation matrix and whitening matrix by multiplication:

Principal Components: $P=WX$

These principal components were combined using their associated weights in the dewhitening matrix to create an individualized template for each QRS complex in the unipolar signal. Since the first principal components are assumed to express the ventricular activity because they express most of the variance from the original observations, QRS templates were created by combining the first 1-2 principal components, using their associated mixing variables from the dewhitening matrix $W^{-1}$ (FIG. 6D). These QRS templates were then subtracted from the original unipolar signals (FIG. 6E).

Although the performance of this algorithm is quite good, residual ventricular artifacts and their corresponding spurious activity in the ANS signal sometimes remain (red intervals in FIG. 6F). For this reason, a novel second algorithm using ECG, unipolar and bipolar signals was added in order to discern whether the negative slope intervals during ventricular activation were ventricular far-field residues or true atrial activations. To do so, significant bipolar activity as a consequence of an atrial activation was detected in the bipolar signal. Intervals within the QRS windows previously used for the PCA algorithm (grey rectangles) that did not present significant bipolar activity were detected (green rectangles in FIG. 6G). The ANS signal was then blanked during those green intervals since the negative slope activity present inside them was not considered as a true atrial activation but as a residual ventricular activity (red intervals in FIG. 6F). Then, activation times were detected on the 'blanked' ANS signal (FIG. 6H) and translated into the corresponding unipolar signal after the QRS subtraction (FIG. 6I). More details about the detection of activation times are presented below.

Note that although bipolar signals are by definition less prone to ventricular far-field, they are inferior to unipolar signals to mark accurate activation times, their amplitudes are not directly proportional to those in the underlying action potentials, and are more prone to fractionation. That is the reason why they have been only used in this study to reinforce the ventricular far-field subtraction and to refine unipolar activation times when needed through an iterative algorithm.

Computation of Time-Domain iFM and iAM: Generation of 'Driver' Maps and Rotational-Footprint Detection Activations were detected at the times when the slopes of the unipolar negative deflections were maximal (cyan points in FIGS. 7A and 8A-B). From these activation times, the instantaneous frequency modulation (iFM) signal was generated. Then, the average (median) iFM values were calculated for each signal in the electroanatomical map and displayed over the atrial anatomy (FIGS. 7D and 8C). 'Islands' with iFM median values clearly higher than their surroundings were considered as 'high-hierarchy' regions potentially driving PersAF. Points in driving areas were visually inspected to ensure that automatic estimations were reliable. Importantly, should isolated points presented outlier but reliable values of high $iFM_{median}$, they were tagged with purple circles since spatial interpolation algorithms used to generate 3D maps may mask them. 3D-interpolation methodology is described below.

In addition to iFM, iAM is also needed to detect 'rotational-footprint positive' locations. Unipolar negative deflection amplitudes (surrogates of the optical phases 0 amplitudes) were calculated around each activation time (red points in FIG. 7A) to compute the iAM signal (the lower the amplitude excursion, the higher the iAM). Then, a frequency and amplitude modulated (FM|AM) signal that incorporates both iFM and iAM dynamic changes and that is similar to an optical signal, was generated (third row in FIG. 7A). Single-signal detection of a rotational-footprint was based on the same criteria presented above for optical signals. The algorithm classified the signal in FIG. 7A as 'rotational-footprint positive' which could be confirmed by phase mapping of interpolated electrical data from the 20 PentaRay electrodes that were fully deployed in the RAA (FIG. 7B) and by analyzing their activation sequence (FIG. 7C). Finally, the information of iFM median maps ('driver' maps) and 'rotational-footprint positive' locations was presented together to easily visualize their spatial correlation (FIG. 7D). More details are provided:

FIG. 8 shows examples of instantaneous frequency modulation (iFM) calculation from 2 unipolar signals (same pig presented in FIG. 7). The signal displayed in panel A is from a region with rotational activation but with low hierarchy (median iFM: 5.3 Hz, $70^{th}$ percentile). The signal displayed in panel B is from a region with high hierarchy (median iFM: 7.3 Hz, maximum value). Ablation of that area terminated PersAF and rendered it non-inducible. FIG. 9 describes in detail the algorithm used to calculate the instantaneous frequency modulation (iFM), instantaneous amplitude modulation (iAM) and rotational-footprint detection using as an example the unipolar signal displayed in FIG. 8A (row 1 in FIG. 9). The slope (first derivative: dV/dt) of the unipolar signal was computed. Although intervals with positive slopes can provide useful information about the orientation of the electrical wavefront with respect of the recording unipolar electrode, activation times in unipolar action potentials are usually defined at the times of maximum negative slope within intrinsicoid deflections. Therefore, intervals in which the slope was positive were assigned a zero value in the first derivative. This way, a signal with peaks corresponding only to intervals of negative slope was obtained (absolute negative slope, ANS, measured in mV/ms, row 2 in FIG. 9). This signal can be easily calculated as follows:

$$ANS(t) = \frac{1}{2}\left(\left|\frac{d\ \text{Unipolar}(t)}{dt}\right| - \frac{d\ \text{Unipolar}(t)}{dt}\right)$$

Then, the times when peaks in ANS(t) met the following criteria were selected as activation times: i) an amplitude above a minimum threshold (minimum slope), ii) a prominence above a certain value (minimum prominence), iii) an amplitude over the noise threshold, and iv) separated at least a minimum refractory period from the previous and the next ones.

The minimum slope (amplitude and prominence) was set as:

$$ANS_{min} = \max\{0.03\ \text{mV/ms}, 0.05 \cdot P_{95^{th}}(\text{ANS})\ \text{mV/ms}\}$$

where the noise threshold for the ANS signal was set to 0.03 mV/ms. The $95^{th}$ percentiles were used as reference instead the maximum value ($100^{th}$ percentile) to prevent excessive thresholds due to artifactually high values in the unipolar signal slope.

The minimum refractory period was set as follows:

$$RP_{min} = \max\left\{50\ \text{ms}, \frac{1000}{1.95 \cdot \min\{DF_{UNI}, DF_{ANS}, DF_{BIP}\}}\ \text{ms}\right\}$$

where $DF_{UNI}$, $DF_{ANS}$ and $DF_{BIP}$ are the dominant frequencies of the unipolar, ANS and bipolar signals respectively. $DF_{UNI}$, $DF_{ANS}$ and DF BIP were calculated as the frequencies with the highest peak in the power spectral density (PSD) of the Unipolar(t), ANS (t) and Bipolar(t) signals respectively. PSD was estimated by a conventional periodogram of the signal previously multiplied by a Kaiser window (β=2.5) and zero-padded to the next higher power of 2. All these dominant frequencies can be used as a rough surrogate of the reciprocal of the average interval between activations. The 1000 factor is used to convert that time into ms. Since activation intervals shorten and lengthen dynamically during fibrillation, the 1/1.95 factor is used to allow for intervals up to 1.95 times shorter than the surrogate average one (1/DF)*1000 ms. Such a value usually provided a reasonable lower limit for the local refractory period. Nevertheless, if that value was lower than 50 ms, the latter was used as the minimum refractory period for the algorithm. The resulting activation times are displayed as blue dots in row 4 of FIG. 9. In some specific subjects in which min {$DF_{UNI}$, $DF_{ANS}$, $DF_{BIP}$} was artifactually low, the median value of the dominant frequencies was used instead:

$$RP_{min} = \max\left\{50\ \text{ms}, \frac{1000}{1.95 \cdot \text{median}\{DF_{UNI}, DF_{ANS}, DF_{BIP}\}}\ \text{ms}\right\}$$

However, although such a lower limit for the refractory period can account for physiological dynamic changes in the local activation intervals, it sometimes may result in too short, artificial intervals. Therefore, an iterative adaptive algorithm was used to refine activations allowing physiological changes in atrial activation lengths. In this specific signal no changes in activation times were performed by the adaptive iterative algorithm (FIG. 9, row 5).

In some few cases, very low amplitude/slope activations are often present and the criteria are not fulfilled for too long, not physiological intervals. In such cases, the noise threshold for the ANS signal was iteratively lowered in 0.005 mV/s steps and the iterative adaptive algorithm run again until those too long intervals were not present.

In addition, the amplitude of the intrinsicoid negative deflections in unipolar signals (surrogate of the 'phase 0' in optical action potentials) was calculated as the unipolar voltage excursion (mV) between the times at which the slope goes below the 4% of the slope at the corresponding activation time. The unipolar values at the activation times and their corresponding lower and upper amplitude limits for the intrinsicoid negative deflection are displayed as blue and red points respectively in row 6 of FIG. 9. By interpolating such excursion amplitudes, we obtained the 'unipolar envelope' signal (UE (t), FIG. 9, row 7) as a surrogate of the optical envelope signal in FIG. 3. Importantly, amplitudes in intervals of ventricular activation are interpolated from the neighbouring ones as they could be affected by ventricular far-field even after the applied QRS minimization strategies. Since these amplitudes dynamically change as well (i.e. are modulated by several factors), their corresponding instantaneous amplitude modulation (iAM) signal (FIG. 9, row 10, red trace) is calculated as follows:

$$iAM(t) = 100\left(1 - \frac{UE(t)}{\max\{UE(t)\}}\right)(\%)$$

Note that the lower the unipolar envelope, the higher the iAM is. Thus, intervals with low values of the iAM signal correspond to times when the unipolar envelope is unaffected, whereas intervals with high values of the iAM index correspond to times when the unipolar envelope is highly affected by some factor/s (e.g. a drifting rotor is passing nearby or the recording electrode is far from the endocardium).

Also, a frequency modulated signal (FM(t)) was obtained by adjusting a sinusoidal wave in order to reach its maxima at the previously detected activation times (FIG. 9, row 8). This way, the dense or sparse the distribution of the oscillations in this FM sinusoidal wave is directly reflects the dynamic changes in the tissue activation rate at that specific location in an intuitive way.

Also, a frequency- and amplitude-modulated (FMIAM) signal was obtained by multiplying the FM signal and the unipolar envelope signal (FIG. 9, row 9):

$$FMIAM(t)=UE(t)\cdot FM(t)$$

Note that this FM IAM signal presents a similar morphology to optical signals. In addition to directly reflect the dynamic changes in the tissue activation rate at that specific location in an intuitive way, this FMIAM signal clearly displays the dynamic changes in the amplitude of the unipolar intrinsicoid negative deflections.

Finally, the instantaneous frequency value between 2 consecutive activation times was calculated as the inverse of the interval between these activations in seconds. Analytically, given N consecutive activation times in ms ($t_0$, $t_1$, . . . , $t_N$), the iFM(t) signal is calculated as follows:

$$iFM(t) = \sum_{n=0}^{N-1} \frac{1000}{t_{n+1} - t_n}[u(t - t_n) - u(t - t_{n+1})]$$

where u(t) is the Heaviside unit step function, defined as $$u(t) = \begin{cases} 0 & t < 0 \\ 1, & t \geq 0 \end{cases}$$

Row 10 in FIG. 9 displays the resulting instantaneous frequency modulation (iFM) signal (blue trace).

Single-signal detection of a rotational-footprint in electrical unipolar signals was performed in an identical way as it was performed for optical signals. In the examples shown in FIGS. 7-9, 18-19 and 20-22 the following parameters were used:

parameter1=4 (minimum increasing iFM cycles)
parameter2=25% (minimum iAM excursion)
parameter3=3 (minimum increasing iAM cycles)
parameter4=85% (iAM threshold)
parameter 5=70 percentile (minimum iFM percentile without increasing iFM together with iAM≥parameter 4 to consider a quasi-stationary/meandering in the surroundings rotor footprint)

As reported in the results section, these parameters were the ones for which the algorithm reached its maximal sensitivity provided that specificity was at least 97.5% considering a 2.5 mm tolerance. Again, note that this tolerance is considerably smaller than the actual lesions created by a conventional ablation catheter. Also, note that this algorithm enables in-vivo individual detection of the locations with a rotational footprint without the need of performing phase or activation mapping of multiple electrograms simultaneously acquired by costly panoramic acquisition techniques (basket catheters/electrode vests) or fully deployed multispline catheters.

Data Interpolation on 3D Maps

Similarly to what is done in conventional electroanatomical mapping systems, we used a modified inverse distance weighting algorithm to interpolate data values in points of the 3D surface mesh from the known values at scattered non-regularly distributed spatial locations (the ones where catheter electrodes were actually located during acquisition).

The assigned values for a function $f$ in an unknown point (x, y, z) in the 3D mesh were calculated as a weighted average of the values available at the N truly acquired points ($x_i$, $y_i$, $z_i$) within a distance D from (x, y, z):

$$f(x, y, z) = \begin{cases} \dfrac{\sum_{i=1}^{N} w_i(x, y, z)\cdot f(x_i, y_i z_i)}{\sum_{i=1}^{N} w_i(x, y, z)} & \text{if } \forall i \in \{1, \ldots, N\} | d\{(x, y, z), (x_i, y_i, z_i)\} \neq 0 \\ f(x_i, y_i, z_i), & \text{if } \exists\, i \in \{1, \ldots, N\} \,|\, d\{(x, y, z), (x_i, y_i, z_i)\} = 0 \end{cases}$$

The weighting value $w_i$(x, y, z) was proportional to the inverse of the distance to each known point raised to a p power:

$$w_i(x, y, z) = \frac{1}{(d\{(x, y, z), (x_i, y_i, z_i)\})^p},\quad i \in \{1, \ldots, N\}$$

where d{(x, y, z), ($x_i$, $y_i$, $z_i$)} is the distance between the point at which we are obtaining the $f$ function interpolated value and (x, y, z) the point at which the function $f$ has a known value. For 3D median/mean iFM maps, bipolar voltage maps and dominant frequency maps, the following parameters were used: D=7 mm, p=2. For 3D phase movies (see next section) p=1 was used instead.

Since 'rotational-footprint' is a binary function (positive=1/negative=0), nearest neighbour interpolation was used within a 2.5 mm distance (the tolerance of the iFM/iAM algorithm) from the truly acquired points ($x_i$, $y_i$, $z_i$). An example is shown in FIG. 10 (left column).

Phase Mapping of In-Vivo Electrical Data

We obtained phase movies using the electrical data provided by the PentaRay catheter.

Note that the detection of rotational activation using phase mapping of electrical data requires multiple electrodes and is completely dependent on their location and separation. Also, depending on the signal processing performed, phase mapping of electrical signals can be little specific for rotor detection. Therefore, one could only expect reliable enough phase movies when the PentaRay catheter is well deployed and it has good contact with the tissue. However, this scenario is not achievable in important areas of the atria. Even so, some difficultly predictable issues can arise due to interpolation of sparse electrode data. Note that all these major drawbacks are not present in phase movies obtained from optical mapping due to the huge number of signals acquired (6400 in our optical movies) and the tiny separation between their locations (0.43-0.62 mm in our optical movies). For these reasons, unlike phase mapping of optical data, phase mapping of electrical data cannot be considered as a 'gold-standard'. Therefore, we only used these phase movies of electrical data to qualitatively assess the correlation between the rotational cores in these phase movies obtained from electrical data and the 'rotational-footprint positive' locations detected by the iFM/iAM algorithm in areas where the PentaRay catheter was fully deployed (see FIG. 7B).

To obtain phases we performed Hilbert transformation (HT) of the frequency modulated (FM) signals from the 20 electrodes ($FM_i(t)$, i=1, . . . , 20). Since they are sinusoids that reflect the changes in AF intervals and not raw unipolar potentials, their morphology is more convenient for phase transformations. Thus, $$\varphi_n(t)=HT\{FM_n(t)\}, n=1, \ldots, 20$$

Once the phase signal of the 20 electrodes was calculated, complex vectors $e^{j\varphi_n(t)}$ whose scalar phases were on (t) were computed. We used these complex vectors to obtain by interpolation the corresponding complex vectors in all the spatial locations of the 3D surface mesh covered by the deployed PentaRay. Of note, we did not directly interpolate the scalar phases $\varphi_n(t)$ (between $-\pi$ and $+\pi$), but their associated complex vectors $e^{j\varphi_i(t)}$, because the first approach would result in phase maps without clear activation fronts. Finally, the scalar phases (between $-\pi$ and $+\pi$) for every point in the 3D surface mesh were retrieved from the interpolated complex vectors. Phase movies display the changes in the scalar phases at each location of the surface mesh for every time point.

QRST Complex Removal and Dominant Frequency Calculation of Surface ECG

If ablation did not achieve AF termination, the atrial frequency content of 12-lead surface ECG was compared before and after ablation to discern whether ablation effectively modified AF substrate. To do so, ventricular components (QRST complexes) were removed from the surface ECG before calculating DF. To estimate the ventricular subtracting signals, the same PCA method described above was used. See FIGS. 11-12 for a schematic representation of the processing performed.

Ablation of 'High-Hierarchy' Regions, AF Acute Termination and Reinduction Protocol Radiofrequency was delivered on 'high-hierarchy' islands (FlexAbility, Abbott; 30-35 W, saline irrigation: 17 ml/min). These regions were targeted until the following endpoints were reached: 1) ablation of all 'islands' in descending order of $iFM_{median}$ or conversion to sinus rhythm; and 2) non-sustainability of AF after ablation. Radiofrequency was delivered until local potentials were completely abated through creation of coin-like sets of lesions. When a region in the coronary sinus (CS) had to be ablated, radiofrequency was first delivered from the corresponding adjacent area of the LA. If AF persisted, radiofrequency was also delivered from the endothelial wall of the CS itself. In case of sinus rhythm conversion during the ablation protocol, ≥3 attempts to reinduce AF with HRAP (20 Hz) were performed from locations far from ablation lesions. AF was considered inducible if it persisted for >10 minutes. In such cases, ablation protocol was resumed until AF was rendered non-inducible. Radiofrequency time to first AF termination and total radiofrequency time for nonsustainability were obtained from automatic annotations of the EP recording system (ClearSign, Boston Scientific). If ablation did not achieve AF termination, the atrial frequency content of 12-lead surface ECG (see FIGS. 11-12) was compared before and after ablation to discern whether ablation effectively modified AF substrate.

Comparison of Median/Mean iFM Maps and Bipolar DF Maps

Some could argue that median iFM maps are similar to the dominant frequency (DF) maps used in previous mechanistic approaches to treat PersAF that offered suboptimal results. However, even though both DF and median iFM approaches try to summarize the frequency content of a signal in one number, important conceptual differences are present. For example, DF is a spectral measurement (obtained from the frequency-domain) and is a very good surrogate of activation rate in optical mapping or for good-quality and quite regular in amplitude and frequency electrical signals, but otherwise, the presence of multiple spectral peaks of similar height makes it not very reliable. On the contrary, median iFM is derived from time-domain measurements that, in ours an others' experience, are more robust than spectral measurements for a wider range of electrical signals when properly designed algorithms are used. Also, the use of iFM instead DF has additional advantages. For example, it would potentially enable to automatically detect regions with transient bursts of triggered activity that could contribute to (re) initiate or maintain AF by comparing values of $50^{th}$ (median) and $90^{th}$ percentiles of iFM. These regions would be difficultly detectable by DF analysis.

We aimed to compare our proposed hierarchy maps (median iFM) with the ones obtained by previous approaches. To do so, we obtained Dominant Frequency (DF) maps from the acquired 8-second bipolar signals at each location. It is important to note that while our iFM maps are displayed in combination with the location of rotational footprints, the latter information cannot be obtained by the simpler DF analysis. Nevertheless, we specifically wanted to qualitatively compare the ability of our approach to detect driver regions while mapping in-vivo with the one approach previously reported that could a priori be considered similar: DF mapping of bipolar signals.

We implemented the same spectral analysis that was reported in those studies. Briefly, power spectral density was obtained via Welch's periodogram (Hanning window) using Matlab (Mathworks Inc., Natwick, USA). A dominant frequency (DF) corresponding to the highest peak in the power spectral density in the range of 3 to 20 Hz was determined for the bipolar signal acquired at each spatial location. The power spectrum was also used to quantify the aperiodic complexity of the signals using the regularity index (RI) which varies between 0 (completely aperiodic) and 1 (completely periodic). RI is defined as the ratio of the power at the DF and adjacent frequencies (~0.75 Hz band) to the sum of the power in the whole analysed frequency range. This index is based on the fact that the most pure signal in the frequency domain is a sinusoidal with infinite duration, which should have a single spectral line (Dirac delta, no spectral width) and therefore its RI should be 1. Since the analyzed signals do not have an infinite duration, even the spectrum calculated from a sinusoid will have some width due to the "temporal windowing" produced by their limited length. This is why a certain frequency margin around the DF is considered when RI is calculated.

Note that although by definition the DF should be the frequency corresponding to the highest peak in the power spectral density, this may return DF values as high as 20 Hz, which is not a physiologically feasible value in this scenario. For this reason, we established 16 Hz as the upper limit for DF, since 16 Hz is the highest activation rate we have ever seen in vivo during persistent AF (see FIG. 18B). However, the existence of harmonic peaks (at double, triple, etc. frequencies of the fundamental one) makes this approach little reliable since the second harmonic is many times selected as DF because is the highest peak in the analyzed band. Therefore, we also tested how the bipolar DF map would be by setting an upper limit of only 8 Hz. Finally, since disorganized signals can display artifactual DF values, we also calculated the bipolar DF map after discarding signals with RI<0.2, as previously reported. While this measure can theoretically help to 'clean' the bipolar DF map by removing low quality or very irregular signals (although is not clear that irregular signals deserve to be ignored), it also eliminates very good signals that display a RI<0.2 due to their markedly harmonic spectrum. This problem could have been mitigated by using the organization index (O1) that takes into account the harmonic structure of the spectrum instead the RI. However, that was not the way it was performed in the referred studies.

FIG. 13 shows a comparison of the following maps: 1) Median iFM, 2) Mean iFM, 3) Bipolar DF (upper limit for DF: 16 Hz), 4) Bipolar DF (upper limit for DF: 8 Hz) and 5) Bipolar DF (upper limit for DF: 8 Hz, only points with RI>0.2). Maps 1 and 2 (median and mean iFM) are virtually identical. Indeed, the correlation between median and mean iFM values at the acquired locations was extremely high ($R^2$=0.94, p<0.0001, n=3204 points) which is a criterion for converge in some iterative algorithms.

The bipolar DF map when the upper limit for DF was set at 16 Hz did not show any global correlation with the median iFM map ($R^2$=0). Although a local good/acceptable correlation is achieved for some points (see FIG. 14 *a-c*), the correlation plot shows how most DF values obtained are much higher that their corresponding median iFM values. Many of these wrong values are due to the selection of the second harmonic as DF (points around the red line in the correlation plots) or simply because of the existence of too many high peaks in the spectrum. Examples of wrongly selected bipolar DF values are shown in FIG. 14 *d-i*.

When the upper limit for DF is set at 8 Hz, the obtained map is slightly more similar to the median iFM map. However, the global correlation is still practically zero ($R^2$=0.01). Note that the driver area in purple in the median iFM map presents high bipolar DF values as well. However, there are many more areas with similar DF values (LIPV, RIPV, RSPV, ICV, SCV, free wall of the RA) which makes this map utterly unspecific. Note that by limiting the upper threshold for DF to 8 Hz, signals d-i presented more physiological DF values, but even so several of them did not show a good correlation with median iFM.

In an attempt to increase the specificity of the DF map, points with RI<0.2 were removed as previously done. This considerably increased the correlation between bipolar DF values and median iFM ($R^2$=0.597, p<0.0001, n=147 points) but >95% of points were removed and only 147 out of 3204 points remained. That resulted in a not very useful map. Note that only 2 signals out of the 9 shown in FIG. 14 presented a RI>0.2 (a and c). Indeed, signal b, whose DF value was very similar to the median iFM value, was removed because its RI was 0.18. This was clearly because harmonic peaks increase the value of denominator but not numerator in the RI ratio, resulting in low RI values even when the signal is very regular. As a consequence of removal of >95% points, large areas of the atrial maps were left empty (dark grey). These areas are not even larger because of the interpolation methods used in 3D maps. In fact, although points b and d-i were removed, they are located inside coloured regions that are the result of interpolation from neighbouring points that remained in the map.

Electroanatomical Mapping and Ablation Protocol in Patients

Electroanatomical mapping was performed in patients in an identical manner as in pigs with PsAF, except for two details: 1) the unipolar reference was taken from the distal electrode in a decapolar catheter advanced into the suprahepatic vein; 2) only one biatrial map was acquired not to lengthen the procedure. Given the extraordinary temporal stability of driver maps in pigs, we consider that a second map was not necessary in order not to increase procedural time, which could unnecessarily increase the risks for the patient. After checking that pulmonary veins remained isolated from the prior procedure, ablation endpoints were the same ones described above. However, the performing physician could stop the ablation procedure if considered that driver regions were too large to be targeted with radiofrequency. Atrial tachycardias/flutters occurring after AF termination were mapped and ablated. If AF persisted after stopping ablation, the AF was cardioverted and the procedure terminated.

Statistical Analysis

Data are generally presented as Median [Interquartile Range]. Non-parametric tests were used: Wilcoxon's test for paired measurements, and Mann-Whitney's or Kruskal-Wallis' tests for comparisons between 2 or more groups of non-paired data, respectively. Mean (Standard Deviation) is provided for data with a high n value and normal distribution according to Saphiro-Wilk's test.

Results

The iFM-iAM Algorithm Successfully Detected Rotational-Footprints in Single Optical Signals with High Sensitivity and Specificity Examples of 'rotor-footprint positive' and 'phase singularity positive' (used as 'gold standard') maps from the 5 sheep are shown in FIG. 15A-C, 16A-B. They show that the algorithm classified as 'rotational-footprint positive' the locations near the cores of drifting rotors and figure-of-eight re-entries, as well as breakthrough activations that eventually turned into a figure-of-eight reentries. However, the algorithm did not detect 'rotational-footprint positive' pixels when true focal or planar wavefront activations were present. Almost 700,000 optical signals from 117 high-quality optical movies from 5 sheep with PersAF were analyzed (8 movies were excluded due to suboptimal quality). Sensitivity and specificity of the iFM/iAM algorithm were tested for 8820 different combinations of 5 parameters for 3 levels of spatial tolerance (0/1.25/2.5 mm) and requiring that all criteria were met for a number of consecutive cycles between 2 and 5. That resulted in a total of 15,479,100 data registers (Table 1). Optimal combinations for any number of parameters (1-5) are presented in Table 2. In the aforementioned Figures/Movies, the parameter combination that maximized the sum of sensitivity and specificity for a tolerance of 1.25 mm was used [sensitivity: 93.1(3.9) %; specificity: 90.6(4.9) %]. To further increase specificity for the in-vivo experiments reported in the next sections, we used the combination that maximized sensitivity provided that specificity was ≥97.5% with 2.5 mm tolerance. That combination provided 92.6 (4.3) % sensitivity and 97.5(2.3) % specificity. FIG. 15D shows a summary of the optimal combinations of parameters.

Pigs Effectively Developed Long-Standing PersAF

Pigs developed PersAF after 4.4[2.5-9.9] months of HRAP (N=16. FIG. 17A). In-vivo mapping procedures were performed after 4.1 [2.7-5.4] months of PersAF (time in 100% AF burden: 7.0[5.0-8.1] months; total time since the beginning of the HRAP protocol: 9.4[7.0-13.1] months; weight: 96[82-108] kg). As AF developed, echocardiography showed an overt dilation of the atrial cavities (normalized per kg). On the contrary, LV ejection fractions remained normal. Histological analyses of LA and RA free walls in PersAF pigs found higher levels of fibrosis than in the sham-operated pigs.

$iFM_{median}$ Maps Effectively Located 'High-Hierarchy Driver Regions to Terminate PersAF Using Radiofrequency Delivery In the 12 pigs with PersAF that constituted the ablation group, 14 in-vivo high-density mapping procedures (2 pigs were mapped months apart) with 2 biatrial maps per procedure, and 13 ablation procedures were performed (one pig was submitted to ablation twice). FIG. 17B displays the overall results of mapping and ablation procedures. A total of 4920 [4435-5855] points were acquired per biatrial map, which took 92[82-98] minutes. First and second maps were finished 2.6[2.4-2.9] hours apart. Sixty-nine driver regions were found in the maps obtained with the $1^{st}$ and $2^{nd}$ sets of data, where 66/69 colocalized (95.7%). A total of 2.5[2.0-4.0] high-hierarchy' regions were found per biatrial map. Maximum/mean values of $iFM_{median}$ inside driver regions were 7.9[7.0-9.3] Hz and 7.3[6.5-8.1] Hz, respectively. The corresponding gradients with their 'low-hierarchy' surroundings were 2.7[2.2-3.3] Hz and 1.4[0.8-1.8] Hz, respectively. See FIG. 17C for regional distributions.

In 12 out of the 13 ablation procedures performed (92.3%), ablation of the 'high-hierarchy' regions resulted in PersAF termination after 16.9[9.2-35.8] minutes of radiofrequency delivery whereupon the first reinduced AF episodes lasted 7.8[0.3-11.9] minutes (FIG. 17D). Should a reinduced episode lasted ≥10 minutes, ablation of 'high-hierarchy' regions was resumed. Non-sustainability was achieved after a total radiofrequency delivery of 20.4[12.8-44.0] minutes. Reinduced AF episodes after the $2^{nd}$ and $3^{rd}$ reinduction attempts lasted only 5.0[0.5-8.5] and 0.3[0.1-2.8] minutes, respectively.

FIG. 18A displays an example of the medium-term stability of iFM maps and PersAF termination after the ablation of 'high-hierarchy' regions. FIG. 18B shows the only procedure in which ablation did not terminate PersAF. However, 12-lead ECG maximum and mean atrial DF values showed that ablation had successfully modified the AF substrate. FIGS. 19A and 20 show an example of a pig that was not sacrificed after a first successful ablation procedure. Our aim was to quantify how long it would take it to develop PersAF again. Importantly, after ablating 'high-hierarchy' regions, AF burden dramatically dropped to 0. Then, the HRAP protocol was resumed and it took >3 weeks to reach 100% AF burden again. This fact confirmed that ablation of regions with high $FM_{median}$ values successfully modified the substrate underlying PersAF maintenance. In addition, one pig underwent 2 mapping procedures 78 days apart to test the stability of driver maps in the long-term. FIGS. 19B and 21 show how the same areas were seemingly driving PersAF in both procedures. The driving role of these areas was demonstrated in the second procedure that included their ablation whereupon PersAF terminated and was not longer inducible.

IFM/iAM Rotational-Footprints were Present in Every 'High-Hierarchy' Region but Mostly Outside them Rotational-footprints were detected by the iFM/iAM algorithm in 24.9% [23.1%-27.6%] of atrial signals. Of note, these rotational-footprints were found inside or at the border of 69/69 'high-hierarchy' regions. However, they only constituted around a quarter of total 'rotational-footprint positive' signals, since 76.8%[70.5%-83.6%] were found outside 'high-hierarchy' regions. In an attempt to be more specific, the same analysis was repeated after requiring that the criteria for rotational-footprint detection were fulfilled for ≥5 consecutive cycles. Rotational-footprints were then found only in 4.6%[4.2%-5.4%] of atrial signals. They were found inside or at the border of 67/69 'high-hierarchy' regions (97.1%). Again, most of ≥5 consecutive cycle rotational-footprints were found outside them (FIG. 17E). This suggests that regardless the temporal stability required for rotational activations, only a minority of them (those with the highest average iFM values) seem to contribute to PersAF maintenance.

IFM Median Maps Effectively Located 'High-Hierarch' Driver Regions in Recurrent Cases of PersAF in Patients with Prior PVI We tested the translation ability of the iFM/iAM approach to patients in 3 complex PersAF cases with ≥1 previous ablation procedures. FIG. 22 shows some examples. Similarly to pigs, too large and fast 'high-hierarchy' regions precluded success of limited ablation to acutely terminate PersAF, which suggested that radiofrequency ablation may not be the best strategy to manage some patients. However, when localized high-hierarchy myocardial regions were identified, limited ablation (~10 min) achieved PersAF termination. Nine months after ablation, 2 out of 3 remain in sinus rhythm without antiarrhythmic drugs.

TABLE 1

| iFM/iAM Algorithm to detect Rotational Footprints: tested combinations | | | | | | | |
|---|---|---|---|---|---|---|---|
| Persistent AF optical movies | 117 | | | | | | |
| Signals per movie† | 5970 ± 150 | | | | | | |
| Total signals | 698,456 | | | | | | |
| **Parameters** | | | | | | | |
| Min. Incr. iFM cycles (parameter_1) | 0 (disabled) | 2 | 3 | 4 | 5 | 6 | 7 |
| iAM Threshold (%) (parameter_4) | 0 (disabled) | 75 | 80 | 85 | 90 | 95 | |

TABLE 1-continued

| | | | | | | | |
|---|---|---|---|---|---|---|---|
| Min. Incr. iAM cycles (parameter_3) | 0 (disabled) | 1 | 2 | 3 | 4 | | |
| Min. iFM percentiles[µ] (parameter_5) | 70 | 75 | 80 | 85 | 90 | 95 | 100 (disabled) |
| Min. iAM excursion (%) (parameter_2) | 0 (disabled) | 5 | 15 | 25 | 35 | 45 | |
| Tested parameter combinations per movie: 8820 | | | | | | | |
| All criteria met for ≥ | 1 cycle | 2 cycles | 3 cycles | 4 cycles | 5 cycles | | |
| Tolerances (mm) | 0 | 1.25 | 2.5 | | | | |
| Total data registers per movie | 132,300 | | | | | | |
| Total data registers | 15,479,100 | | | | | | |

iAM: instantaneous Amplitude Modulation, iFM: instantaneous Frequency Modulation †Camera resolution = 80 × 80 = 6400 pixels but some corner areas were masked due to poor lighting or absence of atrial tissue µMin iFM percentile without increasing iFM together with iAM ≥ iAM Threshold to consider a quasi-stationary/meandering rotor footprint

TABLE 2 iFM/iAM Algorithm to detect Rotational Footprints: optimal parameters

| | Tolerance | # Parameters | iAM Threshold (%) (parameter_4) | Min. Incr. iFM cycles (parameter_1) | Min. Incr. iAM cycles (parameter_3) | Min. iFM percentile[µ] (parameter_5) | Min. iAM excursion (%) (parameter_2) | Sensitivity (%)ʃ | Specificity (%) | Sum (%)ʃ |
|---|---|---|---|---|---|---|---|---|---|---|
| Maximization of the sum of Sensitivity + Specificity | 0 mm | 1[3] | 85 | | | | | 85.5 (12.1) | 61.6 (11.6) | 147.0 (10.4) |
| | | 1 | | 4 | | | | 87.7 (7.3) | 33.1 (11.2) | 121.4 (6.9) |
| | | 2 | 80 | 3 | | | | 71.1 (12.1) | 69.1 (9.1) | 140.3 (7.8) |
| | | 3 | 80 | 3 | 2 | | | 70.3 (10.0) | 72.0 (10.2) | 141.8 (6.8) |
| | | 4 | 80 | 3 | 2 | 70 | | 77.1 (9.4) | 69.8 (10.7) | 146.4 (6.9) |
| | | 5 | 80 | 3 | 2 | 70 | 15 | 77.0 (9.4) | 70.0 (10.6) | 146.4 (6.8) |
| | 1.25 mm* | 1[3] | 90 | | | | | 94.5 (5.5) | 82.9 (12.1) | 177.8 (12.7) |
| | | 1 | | 5 | | | | 93.0 (5.8) | 70.9 (12.5) | 164.3 (12.8) |
| | | 2 | 85 | 3 | | | | 92.2 (6.4) | 87.7 (10.6) | 180.3 (12.4) |
| | | 3 | 85 | 3 | 2 | | | 91.8 (5.5) | 90.6 (6.2) | 182.2 (6.6) |
| | | 4 | 80 | 4 | 2 | 70 | | 93.2 (3.9) | 90.4 (5.0) | 183.4 (4.6) |
| | | 5 | 80 | 4 | 3 | 70 | 25 | 93.1 (3.9) | 90.6 (4.9) | 183.5 (4.5) |
| | 2.50 mm‡ | 1[3] | 90 | | | | | 98.2 (2.4) | 85.5 (13.2) | 184.1 (12.5) |
| | | 1 | | 5 | | | | 98.5 (2.1) | 72.1 (13.4) | 171.0 (12.9) |
| | | 2 | 80 | 4 | | | | 95.4 (4.1) | 93.3 (7.0) | 189.1 (6.3) |
| | | 3 | 85 | 3 | 2 | | | 97.2 (3.0) | 93.3 (6.2) | 190.4 (6.4) |
| | | 4 | 80 | 4 | 3 | 70 | | 97.1 (2.4) | 94.8 (3.5) | 191.9 (4.0) |
| | | 5 | 80 | 4 | 3 | 70 | 35 | 97.0 (2.6) | 95.1 (3.4) | 192.0 (4.0) |
| Maximization of Sensitivity with Specificity ≥ 95% | 0 mm | 1[3] | N/A | | | | | N/A | N/A | N/A |
| | | 1 | | N/A | | | | N/A | N/A | N/A |
| | | 2 | N/A | N/A | | | | N/A | N/A | N/A |
| | | 3 | N/A | N/A | N/A | | | N/A | N/A | N/A |
| | | 4 | 90 | 4 | 3 | 70 | | 21.3 (7.0) | 95.0 (2.8) | 116.3 (5.6) |
| | | 5 | 90 | 4 | 3 | 70 | 15 | 21.3 (7.0) | 95.0 (2.8) | 116.2 (5.6) |
| | 1.25 mm* | 1[3] | N/A | | | | | N/A | N/A | N/A |
| | | 1 | | 7 | | | | 23.4 (14.4) | 97.2 (3.5) | 120.6 (12.2) |
| | | 2 | 90 | 4 | | | | 63.0 (11.0) | 95.8 (6.5) | 159.3 (10.25) |
| | | 3 | 85 | 4 | 2 | | | 76.7 (8.6) | 95.4 (3.6) | 172.0 (8.2) |
| | | 4 | 80 | 5 | 3 | 80 | | 82.6 (7.6) | 95.5 (2.7) | 177.9 (6.9) |
| | | 5 | 80 | 5 | 2 | 80 | 35 | 83.9 (7.3) | 95.1 (2.8) | 178.9 (6.7) |
| | 2.50 mm‡ | 1[3] | N/A | | | | | N/A | N/A | N/A |
| | | 1 | | 7 | | | | 39.6 (18.1) | 97.3 (3.8) | 137.0 (16.2) |
| | | 2 | 85 | 4 | | | | 91.5 (5.9) | 95.5 (7.0) | 187.5 (7.0) |
| | | 3 | 85 | 3 | 3 | | | 94.2 (4.1) | 95.7 (4.1) | 189.8 (5.3) |
| | | 4 | 80 | 4 | 3 | 80 | | 96.8 (2.6) | 95.1 (3.3) | 191.9 (4.0) |
| | | 5 | 80 | 4 | 3 | 70 | 35 | 97.0 (2.6) | 95.1 (3.3) | 192.0 (4.0) |
| Maximization of Specificity with Sensitivity ≥ 95% | 0 mm | 1[3] | N/A | | | | | N/A | N/A | N/A |
| | | 1 | | N/A | | | | N/A | N/A | N/A |
| | | 2 | N/A | N/A | | | | N/A | N/A | N/A |
| | | 3 | N/A | N/A | N/A | | | N/A | N/A | N/A |
| | | 4 | N/A | N/A | N/A | N/A | | N/A | N/A | N/A |
| | | 5 | N/A | N/A | N/A | N/A | N/A | N/A | N/A | N/A |
| | 1.25 mm* | 1[3] | 85 | | | | | 97.6 (3.1) | 76.1 (12.4) | 173.9 (11.6) |
| | | 1 | | 4 | | | | 99.9 (0.2) | 43.3 (12.1) | 144.0 (11.2) |
| | | 2 | 80 | 3 | | | | 96.4 (3.9) | 81.4 (11.0) | 178.1 (9.1) |
| | | 3 | 80 | 3 | 2 | | | 95.9 (3.5) | 84.5 (7.5) | 180.1 (6.7) |
| | | 4 | 75 | 4 | 3 | 70 | | 95.6 (3.1) | 86.3 (6.1) | 181.7 (5.5) |
| | | 5 | 75 | 4 | 3 | 70 | 45 | 95.1 (3.3) | 87.1 (6.0) | 182.0 (5.3) |

TABLE 2-continued iFM/iAM Algorithm to detect Rotational Footprints: optimal parameters

| Tolerance | # Parameters | iAM Threshold (%) (parameter_4) | Min. Incr. iFM cycles (parameter_1) | Min. Incr. iAM cycles (parameter_3) | Min. iFM percentile[µ] (parameter_5) | Min. iAM excursion (%) (parameter_2) | Sensitivity (%)ʃ | Specificity (%) | Sum (%)ʃ |
|---|---|---|---|---|---|---|---|---|---|
| 2.50 | 1[3] | 90 | | | | | 98.2 (2.4) | 85.5 (13.2) | 184.1 (12.5) |
| mm‡ | 1 | | 5 | | | | 98.5 (2.1) | 72.1 (13.4) | 171.0 (13.0) |
| | 2 | 80 | 4 | | | | 95.4 (4.1) | 93.3 (7.0) | 189.1 (6.3) |
| | 3 | 85 | 3 | 2 | | | 97.2 (3.0) | 93.3 (6.2) | 190.4 (6.4) |
| | 4 | 80 | 5 | 2 | 70 | | 95.4 (4.1) | 96.4 (2.6) | 191.7 (4.4) |
| | 5 | 80 | 5 | 2 | 70 | 35 | 95.2 (4.1) | 96.6 (2.6) | 191.7 (4.5) |

Data are expressed as Mean (SD)

iAM: instantaneous Amplitude Modulation, iFM: instantaneous Frequency Modulation

[3]Note that this parameter standalone would not be specific enough used with electrical signals acquired in vivo due to the amplitude modulation produced by the changes in electrode-tissue contact due to catheter or respiratory displacement, ventricular contraction, etc.

*Radius of a conventional ablation catheter

‡Diameter of a conventional ablation catheter

µMin iFM percentile without increasing iFM together with iAM ≥ iAM Threshold to consider a quasi-stationary/meandering rotor footprint ʃTwo movies without true positives were not included for these descriptive statistics since sensitivity could not be calculated

The invention claimed is:

1. A medical apparatus, comprising at least a probe or catheter configured to insert into a heart of a subject with cardiac fibrillation, wherein the probe comprises an elongated body, and one or more mapping electrodes or optical fibers disposed on a distal portion of the body, a memory having one or more programs stored therein, a display, and a processor linked to the display and coupled to access the memory to execute the programs, wherein the processor is connectable to receive an input provided by the mapping electrodes or optical fibers, wherein the one or more programs, when executed by the processor, cause the processor to perform the steps of obtaining a single or multiple electrical unipolar signals or optical signals from a single target or multiple sequential targets in the heart via the mapping electrodes or optical fibers, generating an electroanatomical map based on the assigned electrical or optical data at a single or multiple cardiac spots, and wherein the one or more programs, when executed by the processor, cause the processor to perform the following steps:

a. detecting activations over i) the electrical unipolar signals or ii) the optical signals;

b. obtaining an instantaneous frequency modulation (iFM) signal from the activations of step a) for each i) unipolar electrical signal or ii) optical signal, by calculating a reciprocal of one or more intervals between consecutive activations, and obtaining an instantaneous amplitude modulation (iAM) signal from sequence of amplitude excursions of i) the negative deflections that contain activations in each unipolar electrical signal or ii) the optical phases O that contain activations in each optical signal: wherein the lower an amplitude excursion, the higher its corresponding value in the iAM signal and vice versa;

c. detecting intervals that display the footprint of rotational activity wherein A) simultaneous increase in iFM and iAM is indicative of drifting rotors approaching a cardiac spot or B) simultaneously high iAM and iFM values is indicative of stationary rotors or rotors meandering around a cardiac spot;

d. calculating the mean, median or a specific percentile value of each iFM signal obtained in step b), and obtaining a map by interpolating such values at each of the points used to generate the map, and using such a map to detect cardiac spots wherein such mean, median or specific percentile values are higher than those in their surroundings, such cardiac spots being considered to be the regions potentially driving cardiac fibrillation; and e. presenting the electroanatomical map to guide ablation of at least one area of tissue of the subject on the display in any way in which the regions potentially driving cardiac fibrillation detected in step d) and the cardiac spots displaying the footprint of rotational activity detected in step c) can be identified in the heart of the subject.

2. The medical apparatus of claim 1, wherein the step of detecting intervals that display the footprint of rotational activity comprises selecting intervals upon compliance with at least one of the conditions A or B specified below;

Condition A: a simultaneous increase in iFM and iAM, which is indicative of drifting rotors approaching a cardiac spot, wherein the following logical condition is fulfilled, Increasing iFM(t) for at least parameter_1 cycles AND [(increasing iAM(t) with a minimum excursion of parameter_2% for at least parameter_3 cycles reaching at least parameter 4%) OR iAM(t) ≥parameter_4%]; or Condition B: simultaneous high iAM and iFM values, which is indicative of stationary rotors or rotors meandering around a cardiac spot, wherein the following logical condition is fulfilled: iFM(t)≥parameter_5 percentile AND iAM(t)≥parameter_4% for at least 2 cycles.

3. The medical apparatus according to claim 1, wherein the activations of step a) are detected by first calculating i) an absolute negative slope (ANS) signal/s that is/are obtained as the absolute value of a time derivative of a single or multiple electrical unipolar signal/s obtained via a single or multiple mapping electrode/s, in the intervals with negative slopes and assigning a O value in the intervals with positive slopes; or by first calculating ii) an absolute positive slope (APS) signal/s that is/are obtained as the absolute value of the time derivative of a single or multiple optical signal/s obtained via a single or multiple optical fiber/s, in the intervals with positive slopes and assigning a O value in the intervals with negative slopes.

4. The medical apparatus according to claim 1, wherein the cardiac fibrillation is atrial fibrillation, and wherein the intervals between consecutive atrial activations during atrial fibrillation to provide the iFM signal are calculated by first detecting and excluding false atrial negative deflections due to ventricular electrical far-field in an electrical unipolar signal acquired from an atrium of a heart of a subject during atrial fibrillation, wherein such exclusion of the false atrial negative deflections comprises the following steps:

a. obtaining a bipolar electrical signal from 2 atrial unipolar electrical signals acquired from two atrial locations in the heart of the subject during atrial fibrillation via at least two electrodes, and obtaining a simultaneous surface ECG signal or a simultaneous ventricular signal acquired in the same heart via at least one electrode; and
b. detecting intervals containing false unipolar atrial negative deflections as intervals when simultaneously: i) the unipolar electrical signals from the atria acquired in step a) present negative slope; ii) the simultaneous surface ECG signal or the simultaneous ventricular signal acquired in step a) display ventricular activation; and iii) the bipolar electrical signal indicated in step a) contains negligible voltages;

wherein the instantaneous frequency modulation (iFM) signal is then calculated as the reciprocal of the intervals between consecutive atrial activations during atrial fibrillation after discarding activations contained in the false unipolar atrial negative deflections detected in step b).

5. The medical apparatus according to claim 1, wherein the cardiac fibrillation is atrial fibrillation, and wherein atrial activations in unipolar electrical signals acquired from the atria of a subject with atrial fibrillation to provide the iFM signals are detected by a method which comprises the following steps:

a. obtaining a bipolar electrical signal from 2 atrial unipolar electrical signals acquired from two atrial locations in the heart of the subject during atrial fibrillation via at least two electrodes, and obtaining a simultaneous surface ECG signal or a simultaneous ventricular signal acquired in the same heart via at least one electrode;
b. applying a ventricular far-field subtraction method to the atrial unipolar signal acquired in step a);
c. calculating the absolute negative slope (ANS) signal from the signal obtained after performing step b), wherein the ANS signal/s is/are obtained as the absolute value of the time derivative of a single or multiple electrical unipolar signal/s obtained via a single or multiple mapping electrode/s, in the intervals with negative slopes and assigning a O value in the intervals with positive slopes;
d. detecting local maxima in the ANS signal; wherein the times at which the local maxima are detected are considered potential atrial activations;
e. rejecting the false atrial activations contained in the residual false atrial negative unipolar deflections detected as by first detecting and excluding the false atrial negative deflections due to ventricular electrical far-field in an electrical unipolar signal acquired from an atrium of a heart of a subject during atrial fibrillation, wherein such exclusion of the false atrial negative deflections comprises the following steps:
   i) obtaining a bipolar electrical signal from 2 atrial unipolar electrical signals acquired from two atrial locations in the heart of the subject during atrial fibrillation via at least two electrodes, and obtaining a simultaneous surface ECG signal or a simultaneous ventricular signal acquired in the same heart via at least one electrode; and
   ii) detecting intervals containing false unipolar atrial negative deflections as intervals when simultaneously: i) the unipolar electrical signals from the atria acquired in step a) present negative slope: ii) the simultaneous surface ECG signal or the simultaneous ventricular signal acquired in step a) display ventricular activation; and iii) the bipolar electrical signal indicated in step a) contains negligible voltages;

wherein the instantaneous frequency modulation (FM) signal is then calculated as the reciprocal of the intervals between consecutive atrial activations during atrial fibrillation after discarding activations contained in the false unipolar atrial negative deflections detected in step b); and f) identifying the activations used to calculate the iFM signal.

6. The medical apparatus according to claim 5 wherein said local maxima according to step d) are selected upon compliance with both condition A, a minimum height and prominence, and condition B, a minimum separation from the previous and next detected local maxima:

$$\text{Minimum height and prominence} = \max\{\text{parameter\_1}, \text{parameter\_2}\cdot P_{95th}(\text{ANS})\} \quad \text{Condition A:}$$

wherein $95^{th}$ percentile of ANS signal values is used as reference instead of the maximum value, and parameter_1 is used as noise level threshold, and wherein parameter_1=0.03 and parameter_2=0.05;

Condition B:

$$\text{Min. separation between activitions} == \max\left\{\text{parameter\_3 ms}, \frac{1000}{\text{parameter\_4}\cdot \text{median}\{DF_{UNI}, DF_{ANS}, DF_{BIP}\}}\text{ ms}\right\}$$

or alternatively, condition B:

$$\text{Min. separation between activitions} == \max\left\{\text{parameter\_3 ms}, \frac{1000}{\text{parameter\_4}\cdot \min\{DF_{UNI}, DF_{ANS}, DF_{BIP}\}}\text{ ms}\right\}$$

wherein $DF_{UNI}$ is the dominant frequency of the unipolar electrical signal, $DF_{ANS}$ the dominant frequency of the ANS signal and $DF_{BIP}$ the dominant frequency of the bipolar electrical signal, and wherein parameter_3=50 and parameter_4=1.95, $DF_{UNI}$, $DF_{ANS}$, and $DF_{BIP}$ are calculated as the frequencies with the highest peak in the Fourier transform or the power spectral density (PSD) of the unipolar, ANS and bipolar signals, respectively, wherein PSD is calculated by any known method.

7. The medical apparatus according to claim 1, wherein the cardiac fibrillation is atrial or ventricular fibrillation, wherein cardiac activations are detected in optical signals acquired from the heart of a subject with cardiac fibrillation, to provide the iFM signals, using the following steps:

a. Calculating the APS signal/s as described in claim 3 from one or more optical signal/s from the heart, or from a portion of the heart such as one atrium, both atria, one ventricle or both ventricles, of the subject obtained via a device with one or more optical fiber/s embedded; and b. Detecting local maxima in the APS signal/s, wherein the times at which the local maxima are detected are considered potential cardiac activations, wherein the absolute positive slope (APS) signal/sis/are obtained as the absolute value of the time derivative of a single or multiple optical signal/s obtained via a single or multiple optical fiber/s, in the intervals with positive slopes and assigning a 0 value in the intervals with negative slopes.

8. The medical apparatus according to claim 7, wherein said local maxima according to step b) are selected upon compliance with both condition A, a minimum height and prominence, and condition B, a minimum separation from the previous and next detected local maxima:

Minimum height and prominence=parameter_$1 \cdot P_{95th_}$(APS) Condition A:

wherein $95^{th}$ percentile of APS signal values is used as reference instead of the maximum value, and wherein parameter_1=0.02;

Condition B:

Min. separation between activitions ==

$$\max\left\{\text{parameter\_2 ms}, \frac{1000}{\text{parameter\_3} \cdot \min\{DF_{Optical}, DF_{APS}\}}\text{ ms}\right\}$$

wherein $DF_{Optical}$ is the dominant frequency of the optical signal and $D_{FAPs}$ the dominant frequency of the APS signal, and wherein parameter_2=50 and parameter_3=1.95, $DF_{Optical}$ and $DF_{APS}$ are calculated as the frequencies with the highest peak in the Fourier transform or the power spectral density (PSD) of the optical signal and APS signal respectively and PSD is calculated by any known method.

9. A non-transitory computer-readable medium storing one or more programs comprising instructions that, when executed by at least one processor of a computing device, cause the at least one processor to perform operations comprising: obtaining a single or multiple electrical unipolar signals or optical signals from a single target or multiple sequential targets in the heart via the mapping electrodes or optical fibers, generating an electroanatomical map based on the assigned electrical or optical data at a single or multiple cardiac spots, and wherein the programs, when executed by the processor, cause the processor to perform the following steps:

a. detecting activations over i) the electrical unipolar signals or ii) the optical signals;

b. obtaining an instantaneous frequency modulation (iFM) signal from the activations of step a) for each i) unipolar electrical signal or ii) optical signal, by calculating a reciprocal of one or more intervals between consecutive activations, and obtaining an instantaneous amplitude modulation (iAM) signal from a sequence of amplitude excursions of i) the negative deflections that contain activations in each unipolar electrical signal or ii) the optical phases 0 that contain activations in each optical signal: wherein the lower an amplitude excursion, the higher its corresponding value in the iAM signal and vice versa;

c. detecting intervals that display the footprint of rotational activity wherein A) simultaneous increase in iFM and iAM is indicative of drifting rotors approaching a cardiac spot or B) simultaneously high iAM and iFM values is indicative of stationary rotors or rotors meandering around a cardiac spot;

d. calculating the mean, median or a specific percentile value of each iFM signal obtained in step b), and obtaining a map by interpolating such values at each of the points used to generate the map, and using such a map to detect cardiac spots wherein such mean, median or specific percentile values are higher than those in their surroundings, such cardiac spots being considered to be the regions potentially driving cardiac fibrillation;

e. presenting the electroanatomical map to guide ablation of at least one area of tissue of the subject on a display in any way in which the regions potentially driving cardiac fibrillation detected in step d) and the cardiac spots displaying the footprint of rotational activity detected in step c) can be identified in the heart of the subject.

10. The medical apparatus of claim 1, wherein the cardiac fibrillation is atrial fibrillation.

11. The medical apparatus of claim 1, wherein the cardiac fibrillation is persistent atrial fibrillation.

12. The medical apparatus of claim 1, wherein the intervals between consecutive activations is in seconds.

13. The medical apparatus of claim 1, wherein the percentile value is $90^{th}$ percentile.

14. The medical apparatus of claim 5, wherein applying a ventricular far-field subtraction method to the atrial unipolar signal comprises using principal component analysis to estimate the ventricular far-field signal.

15. The medical apparatus of claim 6, wherein the PSD is calculated by Welch's periodogram.

16. The medical apparatus of claim 7, wherein the cardiac fibrillation is atrial fibrillation.

17. The medical apparatus of claim 7, wherein the cardiac fibrillation is persistent atrial fibrillation.

* * * * *